US006429261B1

(12) United States Patent
Lang et al.

(10) Patent No.: US 6,429,261 B1
(45) Date of Patent: Aug. 6, 2002

(54) ION-SENSITIVE, WATER-DISPERSIBLE POLYMERS, A METHOD OF MAKING SAME AND ITEMS USING SAME

(75) Inventors: Frederick J. Lang, Neenah; Kelly D. Branham, Winneconne, both of WI (US); Yihua Chang, Portland, OR (US); Franklin M. Chen, Appleton, WI (US); Eric D. Johnson, Larsen, WI (US); Jeffrey D. Lindsay, Appleton, WI (US); Pavneet S. Mumick, Belle Mead, NJ (US); William S. Pomplun, West End, NC (US); Kim G. Schick, Menasha; Walter T. Schultz, Appleton, both of WI (US); Dave A. Soerens, Roswell, GA (US); Tong Sun, Neenah, WI (US); Kenneth Y. Wang, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/564,213

(22) Filed: May 4, 2000

(51) Int. Cl.$^7$ .......................... C08F 20/04; D04H 1/60; D04H 1/64
(52) U.S. Cl. ....................... 525/191; 525/217; 525/221; 525/222
(58) Field of Search ................................ 525/191, 217, 525/221, 222

(56) References Cited

U.S. PATENT DOCUMENTS

| | | |
|---|---|---|
| 2,185,789 A | 1/1940 | Jacque |
| 2,306,451 A | 12/1942 | Lilienfeld |
| 2,831,852 A | 4/1958 | Savage |
| 3,097,991 A | 7/1963 | Miller et al. |
| 3,340,327 A | 9/1967 | Spellberg |
| 3,388,082 A | 6/1968 | Rodgers |
| 3,406,688 A | 10/1968 | Cubitt |
| 3,453,261 A | 7/1969 | Scherff |
| 3,461,193 A | 8/1969 | Gilardi |
| 3,480,016 A | 11/1969 | Costanza et al. |
| 3,546,755 A | 12/1970 | Lynch, Jr. |
| 3,561,447 A | 2/1971 | Alexander |
| 3,564,677 A | 2/1971 | Kalwaites |
| 3,582,519 A | 6/1971 | Gomsi |
| 3,595,454 A | 7/1971 | Kalwaites |
| 3,616,797 A | 11/1971 | Champaigne, Jr. et al. |
| 3,639,199 A | 2/1972 | Brandts et al. |
| 3,656,672 A | 4/1972 | Kalwaites |
| 3,663,348 A | 5/1972 | Liloi et al. |
| 3,665,923 A | 5/1972 | Champaigne, Jr. |
| 3,670,069 A | 6/1972 | Mitchell et al. |
| 3,683,919 A | 8/1972 | Ells |
| 3,702,610 A | 11/1972 | Sheppard et al. |
| 3,709,876 A | 1/1973 | Glomski |
| 3,712,847 A | 1/1973 | Rasmussen |
| 3,719,540 A | 3/1973 | Hall |
| 3,753,826 A | 8/1973 | Plummer |
| 3,800,797 A | 4/1974 | Tunc |
| 3,804,092 A | 4/1974 | Tunc |
| 3,838,695 A | 10/1974 | Comerford et al. |
| 3,839,319 A | 10/1974 | Greminger |

(List continued on next page.)

FOREIGN PATENT DOCUMENTS

| | | |
|---|---|---|
| BE | 748453 | 3/1970 |
| CA | 631395 | 11/1991 |
| CA | 2057692 | 10/1992 |
| DE | 1719395 | 12/1970 |
| DE | 2513251 | 9/1976 |

(List continued on next page.)

OTHER PUBLICATIONS

Patent Abstract Japan, JP 06–207324 (Unitka Ltd.), Jul. 26, 1994.
D 5034–11, "Standard Test Method for Breaking Force and Elongation of Textile Fabrics (Grab Test),", 1994 Ann. Book of ASTM Standards, vol. 7.02, pp. 708–709 (1994).
Abstract Derwent WPI, JP 5–179548 (Lion Corp), Jul. 20, 1993).
Abstract Derwent WPI, Jp 5179548 (Lion Corp), Oct. 25, 1991.
Abstract Derwent WPI and JAPIO, JP 03–239709 (Lion Corp) Oct. 25, 1991.
Carlsson et al., "Thermal Gelation of Nonionic Cellulose Ethers and Ionic Surfactants in Water", *Colloids and Surfaces*, vol. 47, pp. 147–165 (1990).
Abstract Derwent WPI, J: 1–306661 (Lion Corp) Dec. 11, 1989.
Chowdhury et al., "Direct Observation of the Gelatin of Rodlike Polymers", *Poly. Mat. Sci. and Eng.*, vol. 59, pp. 1045–1052 (9/88).
Abstract Derwent WPI and JAPIO, JP 63/139906 (Lion Corp.) Jun. 11, 1988.
Nagura et al., "Temperature–Viscosity Relationships of Aqueous Solutions of Cellulose Ethers", Kobunshi Ronbunshu, vol. 38 (3), pp. 133–137 (8/80).
Stafford et al., "Temperature Dependence of the Disintegration times of compressed tablets containing hydroxypropylcellulose as binder", *J. Pharm. Pharmac.*, vol. 30, pp. 1–5 (8/77).
Govindan, T.S., "Process of Making Smooth Vapro–Permeable Microporous Sheet Material", *Defensive Publication*, vol. T901 (007),(8/72).

*Primary Examiner*—Nathan M. Nutter
(74) *Attorney, Agent, or Firm*—Kilpatrick Stockton LLP

(57) ABSTRACT

The present invention is directed to ion-sensitive, water-dispersible polymers. The present invention is also directed to a method of making ion-sensitive, water-dispersible polymers and their applicability as binder compositions. The present invention is further directed to fiber-containing fabrics and webs comprising ion-sensitive, water-dispersible binder compositions and their applicability in water-dispersible personal care products.

24 Claims, 3 Drawing Sheets

U.S. PATENT DOCUMENTS

| | | |
|---|---|---|
| 3,865,918 A | 2/1975 | Mitchell et al. |
| 3,867,324 A | 2/1975 | Clendinning |
| 3,867,549 A | 2/1975 | Costello et al. |
| 3,869,310 A | 3/1975 | Fukushima et al. |
| 3,881,210 A | 5/1975 | Drach et al. |
| 3,881,487 A | 5/1975 | Schrading |
| 3,882,869 A | 5/1975 | Hanke |
| 3,897,782 A | 8/1975 | Tunc |
| 3,913,579 A | 10/1975 | Srinivasan et al. |
| 3,926,951 A | 11/1975 | Lindenfors et al. |
| 3,923,592 A | 12/1975 | George et al. |
| 3,939,836 A | 2/1976 | Tunc |
| 3,950,578 A | 4/1976 | Laumann |
| 3,952,745 A | 4/1976 | Duncan |
| 3,976,734 A | 8/1976 | Dunning et al. |
| 3,978,257 A | 8/1976 | Ring |
| RE28,957 E | 9/1976 | Drelich et al. |
| 4,005,251 A | 1/1977 | Tunc |
| 4,009,313 A | 2/1977 | Crawford et al. |
| 4,011,871 A | 3/1977 | Taft |
| 4,032,993 A | 7/1977 | Coquard et al. |
| 4,035,540 A | 7/1977 | Gander |
| 4,073,777 A | 2/1978 | O'Neill et al. |
| 4,082,886 A | 4/1978 | Butterworth et al. |
| 4,084,591 A | 4/1978 | Takebe et al. |
| 4,092,454 A | 5/1978 | Domoto et al. |
| 4,099,976 A | 7/1978 | Kraskin et al. |
| 4,112,167 A | 9/1978 | Dake et al. |
| 4,117,187 A | 9/1978 | Adams et al. |
| 4,136,798 A | 1/1979 | Oberstein |
| 4,154,883 A | 5/1979 | Elias |
| 4,171,713 A | 10/1979 | Ammannati et al. |
| 4,201,216 A | 5/1980 | Mattei |
| 4,220,244 A | 9/1980 | Elmore |
| 4,226,753 A | 10/1980 | Lewis et al. |
| 4,245,744 A | 1/1981 | Daniels et al. |
| 4,258,849 A | 3/1981 | Miller |
| 4,301,203 A | 11/1981 | Keuchel |
| 4,306,998 A | 12/1981 | Wenzel et al. |
| 4,332,319 A | 6/1982 | Hurwood |
| 4,343,134 A | 8/1982 | Davidowich et al. |
| 4,343,403 A | 8/1982 | Daniels |
| 4,344,804 A | 8/1982 | Bijen et al. |
| 4,372,447 A | 2/1983 | Miller |
| 4,377,544 A | 3/1983 | Rasmussen |
| 4,377,645 A | 3/1983 | Guthrie et al. |
| 4,385,019 A | 5/1983 | Bernstein et al. |
| 4,419,403 A | 12/1983 | Varona |
| 4,440,105 A | 4/1984 | Jeltema |
| 4,496,618 A | 1/1985 | Okamoto |
| 4,511,687 A | 4/1985 | Nakanishi |
| 4,512,279 A | 4/1985 | Damrau et al. |
| 4,528,360 A | 7/1985 | Fujita et al. |
| 4,575,891 A | 3/1986 | Valente |
| 4,585,835 A | 4/1986 | Saegusa |
| 4,588,400 A | 5/1986 | Ring et al. |
| 4,594,389 A | 6/1986 | Lal |
| 4,600,404 A | 7/1986 | Sheldon et al. |
| 4,617,235 A | 10/1986 | Shinonome et al. |
| 4,627,950 A | 12/1986 | Matsui et al. |
| 4,702,947 A | 10/1987 | Pall et al. |
| 4,725,489 A | 2/1988 | Jones et al. |
| 4,732,797 A | 3/1988 | Johnson et al. |
| 4,737,405 A | 4/1988 | Bouchette |
| 4,738,992 A | 4/1988 | Larson et al. |
| 4,740,398 A | 4/1988 | Bouchette |
| 4,753,844 A | 6/1988 | Jones et al. |
| 4,755,421 A | 7/1988 | Manning et al. |
| 4,772,492 A | 9/1988 | Bouchette |
| 4,772,501 A | 9/1988 | Johnson et al. |
| 4,781,974 A | 11/1988 | Bouchette et al. |
| 4,792,326 A | 12/1988 | Tews |
| 4,795,668 A | 1/1989 | Krueger et al. |
| 4,814,131 A | 3/1989 | Atlas |
| 4,837,078 A | 6/1989 | Harrington |
| 4,855,132 A | 8/1989 | Heller et al. |
| 4,894,118 A | 1/1990 | Edwards et al. |
| 4,930,942 A | 6/1990 | Keyes et al. |
| 4,998,984 A | 3/1991 | McClendon |
| 5,009,652 A | 4/1991 | Morgan et al. |
| 5,033,172 A | 7/1991 | Harrington |
| 5,045,387 A | 9/1991 | Schmalz |
| 5,049,440 A | 9/1991 | Bornhoeft, III et al. |
| 5,053,482 A | 10/1991 | Tietz |
| 5,057,361 A | 10/1991 | Sayovitz et al. |
| 5,084,136 A | 1/1992 | Haines et al. |
| 5,096,640 A | 3/1992 | Brody et al. |
| 5,097,004 A | 3/1992 | Gallagher et al. |
| 5,097,005 A | 3/1992 | Tietz |
| 5,102,601 A | 4/1992 | Farris et al. |
| 5,104,367 A | 4/1992 | Hill |
| 5,104,923 A | 4/1992 | Steinwand et al. |
| 5,120,598 A | 6/1992 | Robeson et al. |
| 5,145,727 A | 9/1992 | Potts et al. |
| 5,149,335 A | 9/1992 | Kellenberger et al. |
| 5,171,308 A | 12/1992 | Gallagher et al. |
| 5,171,309 A | 12/1992 | Gallagher et al. |
| 5,171,402 A | 12/1992 | Haines et al. |
| 5,173,526 A | 12/1992 | Vijayendram et al. |
| 5,178,646 A | 1/1993 | Barber, Jr. et al. |
| 5,178,812 A | 1/1993 | Sanford et al. |
| 5,181,966 A | 1/1993 | Honeycutt et al. |
| 5,181,967 A | 1/1993 | Honeycutt |
| 5,196,470 A | 3/1993 | Anderson et al. |
| 5,205,968 A | 4/1993 | Damrow et al. |
| 5,206,064 A | 4/1993 | Scholz |
| 5,207,662 A | 5/1993 | James |
| 5,207,837 A | 5/1993 | Honeycutt |
| 5,208,098 A | 5/1993 | Stover |
| 5,216,050 A | 6/1993 | Sinclair |
| 5,217,495 A | 6/1993 | Kaplan et al. |
| 5,217,798 A | 6/1993 | Brady et al. |
| 5,227,101 A | 7/1993 | Mahoney et al. |
| 5,246,647 A | 9/1993 | Beck et al. |
| 5,248,461 A | 9/1993 | Pluyter et al. |
| 5,256,417 A | 10/1993 | Koltisko |
| 5,257,982 A | 11/1993 | Cohen et al. |
| 5,264,269 A | 11/1993 | Kakiuchi et al. |
| 5,264,491 A | 11/1993 | Quirk |
| 5,270,358 A | 12/1993 | Asmus |
| 5,275,699 A | 1/1994 | Allan et al. |
| 5,281,306 A | 1/1994 | Kakiuchi et al. |
| 5,286,538 A | 2/1994 | Pearlstein et al. |
| 5,295,985 A | 3/1994 | Romesser et al. |
| 5,300,192 A | 4/1994 | Hansen et al. |
| 5,304,420 A | 4/1994 | Hirakawa et al. |
| 5,312,883 A | 5/1994 | Komatsu et al. |
| 5,317,063 A | 5/1994 | Komatsu et al. |
| 5,330,827 A | 7/1994 | Hansen |
| 5,330,832 A | 7/1994 | Liu |
| 5,334,176 A | 8/1994 | Buenger et al. |
| 5,346,541 A | 9/1994 | Goldman et al. |
| 5,360,826 A | 11/1994 | Egolf et al. |
| 5,366,804 A | 11/1994 | Dugan |
| 5,369,155 A | 11/1994 | Asmus |
| 5,384,189 A | 1/1995 | Kuroda et al. |
| 5,393,602 A | 2/1995 | Urry |
| 5,405,342 A | 4/1995 | Roessler et al. |
| 5,407,442 A | 4/1995 | Karapasha |
| 5,409,747 A | 4/1995 | Pearlstein et al. |
| 5,415,813 A | 5/1995 | Misselyn et al. |

| | | |
|---|---|---|
| 5,427,899 A | 6/1995 | Avison et al. |
| 5,437,908 A | 8/1995 | Demura et al. |
| 5,442,016 A | 8/1995 | Jarrett |
| 5,458,591 A | 10/1995 | Roessler et al. |
| 5,466,410 A | 11/1995 | Hills |
| 5,466,518 A | 11/1995 | Issac et al. |
| 5,470,640 A | 11/1995 | Modrak |
| 5,470,941 A | 11/1995 | Kim et al. |
| 5,473,789 A | 12/1995 | Oster |
| 5,476,909 A | 12/1995 | Kim |
| 5,486,307 A | 1/1996 | Misselyn et al. |
| 5,500,068 A | 3/1996 | Srinivasan et al. |
| 5,500,281 A | 3/1996 | Srinivasan et al. |
| 5,514,380 A | 5/1996 | Song |
| 5,519,085 A | 5/1996 | Ma |
| 5,522,841 A | 6/1996 | Roby |
| 5,530,074 A | 6/1996 | Jarrett |
| 5,532,300 A | 7/1996 | Koubek et al. |
| 5,532,306 A | 7/1996 | Kauffman et al. |
| 5,534,178 A | 7/1996 | Bailly et al. |
| 5,542,566 A | 8/1996 | Glaug et al. |
| 5,545,472 A | 8/1996 | Koubek et al. |
| 5,569,230 A | 10/1996 | Fisher et al. |
| 5,578,344 A | 11/1996 | Ahr et al. |
| 5,589,545 A | 12/1996 | Ramachandran |
| 5,604,195 A | 2/1997 | Misselyn et al. |
| 5,612,404 A | 3/1997 | Das et al. |
| 5,613,959 A | 3/1997 | Roessler et al. |
| 5,616,201 A | 4/1997 | Finch et al. |
| 5,618,911 A | 4/1997 | Kirmua |
| 5,620,788 A | 4/1997 | Garavaglia et al. |
| 5,629,081 A | 5/1997 | Richards et al. |
| 5,631,317 A | 5/1997 | Komatsu et al. |
| 5,647,862 A | 7/1997 | Osborn, III et al. |
| 5,647,863 A | 7/1997 | Hammons et al. |
| 5,649,336 A | 7/1997 | Finch et al. |
| 5,670,110 A | 9/1997 | Dirk et al. |
| 5,684,075 A | 11/1997 | Patel et al. |
| 5,693,698 A | 12/1997 | Patel et al. |
| 5,695,551 A | 12/1997 | Buckingham et al. |
| 5,698,322 A | 12/1997 | Tsai et al. |
| 5,714,157 A | 2/1998 | Sandell et al. |
| 5,725,789 A | 3/1998 | Huber et al. |
| 5,725,821 A | 3/1998 | Gannon et al. |
| 5,753,246 A | 5/1998 | Peters |
| 5,763,044 A | 6/1998 | Ahr et al. |
| 5,763,332 A | 6/1998 | Gordon et al. |
| 5,765,717 A | 6/1998 | Gottselig |
| 5,766,758 A | 6/1998 | Hirakawa et al. |
| 5,770,528 A | 6/1998 | Mumick et al. |
| 5,786,065 A | 7/1998 | Annis et al. |
| 5,795,921 A | 8/1998 | Dyer et al. |
| 5,800,417 A | 9/1998 | Goerg-Wood et al. |
| 5,837,627 A | 11/1998 | Halabisky et al. |
| 5,846,230 A | 12/1998 | Osborn, III et al. |
| 5,849,805 A | 12/1998 | Dyer |
| 5,866,675 A | 2/1999 | Ahmed et al. |
| 5,869,596 A | 2/1999 | Ahmed et al. |
| 5,871,763 A | 2/1999 | Luu et al. |
| 5,899,893 A | 5/1999 | Dyer et al. |
| 5,905,046 A | 5/1999 | Takeda et al. |
| 5,916,678 A | 6/1999 | Jackson et al. |
| 5,935,384 A | 8/1999 | Taniguchi |
| 5,935,880 A | 8/1999 | Wang et al. |
| 5,948,710 A | 9/1999 | Pomplun et al. |
| 5,952,077 A | 9/1999 | Booth et al. |
| 5,958,187 A | 9/1999 | Bhat et al. |
| 5,958,555 A | 9/1999 | Takeuchi et al. |
| 5,969,052 A | 10/1999 | Mumick et al. |
| 5,971,138 A | 10/1999 | Soughan |
| 5,972,805 A | 10/1999 | Pomplun et al. |
| 5,980,673 A | 11/1999 | Takeuchi et al. |
| 5,986,004 A | 11/1999 | Pomplun et al. |
| 6,005,045 A | 12/1999 | Klanica |
| 6,010,972 A | 1/2000 | Zacharias et al. |
| 6,017,832 A | 1/2000 | Yahiaoui et al. |
| 6,028,016 A | 2/2000 | Yahiaoui et al. |
| 6,031,045 A | 2/2000 | Wei et al. |
| 6,042,769 A | 3/2000 | Gannon et al. |
| 6,043,317 A | 3/2000 | Mumick et al. |
| 6,053,235 A | 5/2000 | Brozinsky |
| 6,059,882 A | 5/2000 | Steinhardt et al. |
| 6,059,928 A | 5/2000 | Van Luu et al. |
| 6,083,854 A | 7/2000 | Bogdanski et al. |
| 6,098,836 A | 8/2000 | Gottselig |
| 6,103,858 A | 8/2000 | Yamamoto et al. |
| 6,121,170 A | 9/2000 | Tsai et al. |
| 6,123,811 A | 9/2000 | Komarnycky et al. |
| 6,127,593 A | 10/2000 | Bjorkquist et al. |
| 6,132,557 A | 10/2000 | Takeuchi et al. |
| 6,187,141 B1 | 2/2001 | Takeuchi et al. |
| 6,190,502 B1 | 2/2001 | Takeuchi et al. |
| 6,194,517 B1 | 2/2001 | Pomplun et al. |

FOREIGN PATENT DOCUMENTS

| | | |
|---|---|---|
| EP | 0 597 978 B1 | 3/1966 |
| EP | 0 206 489 A2 | 12/1986 |
| EP | 0 303 528 | 2/1989 |
| EP | 0 355 254 | 2/1990 |
| EP | 0 525 671 A1 | 3/1993 |
| EP | 0 358 313 B1 | 8/1993 |
| EP | 0 241 127 B1 | 10/1993 |
| EP | 372 388 B1 | 2/1994 |
| EP | 0 601 518 | 6/1994 |
| EP | 0 608 460 | 8/1994 |
| EP | 0 613 675 A1 | 9/1994 |
| EP | 0 619 074 A1 | 10/1994 |
| EP | 0 620 256 A3 | 10/1994 |
| EP | 0 421 163 B1 | 11/1994 |
| EP | 0 572 569 B1 | 12/1994 |
| EP | 0 639 381 A1 | 2/1995 |
| EP | 0 507 878 B1 | 4/1995 |
| EP | 0 648 871 | 4/1995 |
| EP | 0 552 762 B1 | 8/1995 |
| EP | 0 672 787 A2 | 9/1995 |
| EP | 0 445 655 B1 | 11/1995 |
| EP | 0 689 817 A2 | 1/1996 |
| EP | 0 726 068 | 8/1996 |
| EP | 0 580 764 B1 | 1/1997 |
| EP | 0 791 795 | 3/1997 |
| EP | 0 765 649 A2 | 4/1997 |
| EP | 0 768 425 A2 | 4/1997 |
| EP | 0 225 800 B1 | 5/1997 |
| EP | 0 443 627 B1 | 6/1997 |
| EP | 0 779 387 A2 | 6/1997 |
| EP | 0 781 538 | 7/1997 |
| EP | 0 801 157 A2 | 10/1997 |
| EP | 0 807 704 | 11/1997 |
| EP | 0 598 204 B1 | 12/1997 |
| EP | 0 531 112 B1 | 3/1998 |
| EP | 0 549 988 B1 | 6/1998 |
| EP | 0 637 950 B1 | 7/1998 |
| EP | 0 766 756 B1 | 9/1998 |
| EP | 0 864 418 A2 | 9/1998 |
| EP | 0 873 100 B1 | 10/1998 |
| EP | 0 875 233 A1 | 11/1998 |
| EP | 0 792 144 B1 | 12/1998 |
| EP | 0 706 361 B1 | 3/1999 |
| EP | 0 905 313 A2 | 3/1999 |
| EP | 0 580 811 B1 | 8/1999 |
| EP | 0 937 453 | 8/1999 |
| EP | 0 693 915 B1 | 9/1999 |

| | | | | | | |
|---|---|---|---|---|---|---|
| EP | 0 699 727 A1 | 9/1999 | | WO | WO 96/30576 | 10/1996 |
| EP | 0 699 727 B1 | 9/1999 | | WO | WO 97/02375 | 1/1997 |
| EP | 0 945 536 A2 | 9/1999 | | WO | WO 97/02376 | 1/1997 |
| EP | 0 766 755 B1 | 12/1999 | | WO | WO 97/16597 | 5/1997 |
| EP | 0 793 743 B1 | 3/2000 | | WO | WO 97/18784 | 5/1997 |
| EP | 1 024 255 A1 | 8/2000 | | WO | WO 97/47227 | 12/1997 |
| EP | 1 046 747 A1 | 10/2000 | | WO | WO 98/29501 | 7/1998 |
| FR | 2672788 | 8/1992 | | WO | WO 98/36117 | 8/1998 |
| JP | 4943114 | 11/1974 | | WO | WO 98/41577 | 9/1998 |
| JP | 5125123 | 5/1993 | | WO | WO 98/44181 | 10/1998 |
| JP | 6172453 | 6/1994 | | WO | WO 98/48684 | 11/1998 |
| JP | 06220793 A | 8/1994 | | WO | WO 98/53006 A1 | 11/1998 |
| JP | 8239428 | 9/1996 | | WO | WO 99/01106 A1 | 1/1999 |
| RU | 705013 | 12/1979 | | WO | WO 99/06523 | 2/1999 |
| WO | WO 99/25318 A1 | 5/1979 | | WO | WO 99/07273 A1 | 2/1999 |
| WO | WO 90/03156 | 4/1990 | | WO | WO 00/00026 A1 | 1/2000 |
| WO | WO 93/07199 | 4/1993 | | WO | WO 00/38751 A1 | 7/2000 |
| WO | WO 94/25189 | 11/1994 | | WO | WO 00/39378 A2 | 7/2000 |
| WO | WO 95/18191 | 7/1995 | | WO | WO 01/13880 A1 | 3/2001 |
| WO | WO 96/12615 | 5/1996 | | | | |

Figure 1: CDWT (in 1.5% and 4.0% NaCl) and soaked CD tensiles (1 and 3 hour soak in hard water) for NaAMPS-SSB/Dur-O-Set RB-based basesheets

ION-SENSITIVE, WATER-DISPERSIBLE POLYMERS, A METHOD OF MAKING SAME AND ITEMS USING SAME

FIELD OF THE INVENTION

The present invention is directed to ion-sensitive, water-dispersible polymer formulations. The present invention is also directed to a method of making ion-sensitive, water-dispersible polymer formulations and their applicability as binder compositions for disposable items. The present invention is further directed to disposable items, such as wet-wipes comprising ion-sensitive, water-dispersible binder compositions.

BACKGROUND OF THE INVENTION

For many years, the problem of disposability has plagued industries which provide disposable items, such as, diapers, wet wipes, incontinent garments and feminine care products. While much headway has been made in addressing this problem, one of the weak links has been the inability to create an economical coherent fibrous web, which will readily dissolve or disintegrate in water, but still have sufficient in-use strength. See, for example, U.K. patent disclosure 2,241,373 and U.S. Pat. No. 4,186,233. Without such a product, the ability of the user to dispose of the product by flushing it down the toilet is greatly reduced, if not eliminated. Furthermore, the ability of the product to disintegrate in a landfill is quite limited because a large portion of the product components, which may well be biodegradable or photodegradable, are encapsulated in or bound together by plastic which degrades over a long period of time, if at all. Accordingly, if the plastic disintegrated in the presence of water, the internal components could degrade as a result of the rupture of the plastic encapsulation or binding.

Disposable products, such as diapers, feminine care products and adult incontinent care products may be made to be disposed by flushing down toilets. Usually such products comprise a body side liner which must rapidly pass fluids, such as urine or menses, so that the fluid may be absorbed by an absorbent core of the product. Typically, the body side liner may be a coherent fibrous web, which desirably possesses a number of characteristics, such as softness and flexibility. The fibrous web of the body side liner material may be typically formed by wet or dry (air) laying a generally random plurality of fibers and joining them together to form a coherent web with a binder compositions. Past binder compositions have preformed this function well. However, fibrous webs comprising these compositions tended to be non-dispersible and present problems in typical household sanitation systems.

Recent binder compositions have been developed which can be more dispersible and are more environmentally responsible than past binder compositions. One class of binder compositions includes polymeric materials having inverse solubility in water. These binder compositions are insoluble in warm water, but are soluble in cold water, such as found in a toilet. It is well known that a number of polymers exhibit cloud points or inverse solubility properties in aqueous media. These polymers have been cited in several publications for various applications, including (1) as evaporation retarders (JP 6207162); (2) as temperature sensitive compositions, which are useful as temperature indicators due to a sharp color change associated with a corresponding temperature change (JP 6192527); (3) as heat sensitive materials that are opaque at a specific temperature and become transparent when cooled to below the specific temperature (JP 51003248 and JP 81035703); (4) as wound dressings with good absorbing characteristics and easy removal (JP 6233809); and (5) as materials in flushable personal care products (U.S. Pat. No. 5,509,913, issued to Richard S. Yeo on Apr. 23, 1996 and assigned to Kimberly-Clark Corporation).

Other recent binders of interest include a class of binders, which are ion-sensitive. Several U.S. and European patents assigned to Lion Corporation of Tokyo, Japan, disclose ion-sensitive polymers comprising acrylic acid and alkyl or aryl acrylates. See U.S. Pat. Nos. 5,312,883, 5,317,063 and 5,384,189, the disclosures of which are incorporated herein by reference, as well as, European Pat. No. 608460A1. In U.S. Pat. No. 5,312,883, terpolymers are disclosed as suitable binders for flushable nonwoven webs. The disclosed acrylic acid-based terpolymers, which comprise partially neutralized acrylic acid, butyl acrylate and 2-ethylhexyl acrylate, are suitable binders for use in flushable nonwoven webs in some parts of the world. However, because of the presence of a small amount of sodium acrylate in the partially neutralized terpolymer, these binders fail to disperse in water containing more than about 15 ppm $Ca^{2+}$ and/or $Mg^{2+}$. When placed in water containing more than about 15 ppm $Ca^{2+}$ and/or $Mg^{2+}$ ions, nonwoven webs using the above-described binders maintain a tensile strength greater than 30 g/in, which negatively affects the "dispersibility" of the web. The proposed mechanism for the failure is that each calcium ion binds with two carboxylate groups either intramolecularly or intermolecularly. Intramolecular association causes the polymer chain to coil up, which eventually leads to polymer precipitation. Intermolecular association yields crosslinking. Whether intramolecular or intermolecular associations are taking place, the terpolymer is not soluble in water containing more than about 15 ppm $Ca^{2+}$ and/or $Mg^{2+}$. Due to the strong interaction between calcium ions and the carboxylate groups of the terpolymer, dissociation of the complex is highly unlikely because this association is irreversible. Therefore, the above-described polymer that has been exposed to a high $Ca^{2+}$ and/or $Mg^{2+}$ concentration solution will not disperse in water even if the calcium concentration decreases. This limits the application of the polymer as a flushable binder material because most areas across the U.S. have hard water, which contains more than 15 ppm $Ca^{2+}$ and/or $Mg^{2+}$.

In a co-pending application assigned to Kimberly Clark; i.e., U.S. patent application Ser. No. 09/223,999, filed Dec. 31, 1998, the disclosure of which is incorporated herein by reference, there is disclosed a modification of the acrylic acid terpolymers of the above-referenced patents to Lion Corporation. Specifically, U.S. patent application Ser. No. 09/223,999 discloses a sulfonate anion modified acrylic acid terpolymers which has improved dispersibility in relatively hard water; e.g., up to 200 ppm $Ca^{2+}$ and/or $Mg^{2+}$, compared to the unmodified Lion polymers. However, the Lion Corporation ion-sensitive polymers of the above-referenced patents and the sulfonate anion modified acrylic acid terpolymers of the co-pending application, when used as binders for personal care products, such as wet wipes, typically have reduced sheet wettability, increased sheet stiffness, increased sheet stickiness, reduced binder sprayability and relatively high product cost.

Another approach to dispersible personal care products is disclosed in U.S. Pat. No. 5,281,306 to Kao Corporation of Tokyo, Japan. This patent discloses a water-disintegratable cleansing sheet; i.e., wet wipe, comprising water-dispersible fibers treated with a water-soluble binder having a carboxyl group. The cleansing sheet is treated with a cleansing agent containing 5%–95% of a water-compatible organic solvent and 95%–5% water. A preferred organic solvent is propylene glycol. The cleansing sheet retains wet strength and does not disperse in the organic solvent-based cleansing agent, but disperses in water.

Although many patents disclose various ion and temperature sensitive compositions for water-dispersible or flushable materials, there exists a need for dispersible products possessing softness, flexibility, three dimensionality, and resiliency; wicking and structural integrity in the presence of body fluids (including feces) at body temperature; and true fiber dispersion after toilet flushing so that fibers do not become entangled with tree roots or at bends in sewer pipes. In addition, the known ion-sensitive polymers, such as those of Lion Corporation and the co-pending application of Kimberly Clark, have relatively high viscosities at high shear rates that make application by spraying impossible or impractical. Moreover, there is a need in the art for flushable products having water-dispersibility in all areas of the world, including soft and hard water areas. Furthermore, there is a need for water-dispersible binders that do not reduce wettability of product with which they are used and are sprayable for easy and uniform application to and penetration into products. Finally, there is a need for water-dispersible, flushable wet wipes that are stable during storage and retain a desired level of wet strength during use and are wetted with a wetting composition that is relatively free, or is substantially free, of organic solvents. Such a product is needed at a reasonable cost without compromising product safety and environmental concerns, something that past products have failed to do.

SUMMARY OF THE INVENTION

The present invention is directed to ion-sensitive polymer formulations, which have been developed to address the above-described problems associated with currently available, ion-sensitive polymers and other polymers described in literature. The ion-sensitive polymer formulations of the present invention have a "trigger property," such that the polymers are insoluble in a wetting composition comprising ions of a particular type and concentration, such as monovalent salt solutions at a concentration from about 0.3% to 10%, but can be soluble when diluted with water, including divalent salt solutions such as hard water with up to 200 ppm (parts per million) calcium and magnesium ions. Unlike some ion-sensitive polymer formulations, which lose dispersibility in hard water because of ion cross-linking by calcium ions, the polymer formulations of the present invention are relatively insensitive to calcium and/or magnesium ions. Consequently, flushable products containing the polymer formulations of the present invention maintain dispersibility in hard water. Furthermore, the ion-sensitive polymer formulations of the present invention can have improved properties of sprayability or reduced high-shear viscosity, improved product wettability or decreased properties of product stiffness and stickiness.

The polymer formulations of the present invention are useful as binders and structural components for air-laid and wet-laid nonwoven fabrics for applications such as body-side liners, fluid distribution materials, fluid in-take materials (surge) or cover stock in various personal care products. The polymer formulations of the present invention are particularly useful as a binder material for flushable personal care products, particularly wet wipes for personal use such as cleaning or treating skin, make-up removal, nail polish removal, medical care, and also wipes for use in hard surface cleaning, automotive care, including wipes comprising cleaning agents, disinfectants, and the like. The flushable products maintain integrity or wet strength during storage and use, and break apart or disperse after disposal in the toilet when the salt concentration falls below a critical level. Suitable substrates for treatment include tissue, such as creped or uncreped tissue, coform products, hydroentangled webs, airlaid mats, fluff pulp, nonwoven webs, and composites thereof. Methods for producing uncreped tissues and molded three-dimensional tissue webs of use in the present invention can be found in commonly owned U.S. patent application, Ser. No. 08/912,906, "Wet Resilient Webs and Disposable Articles Made Therewith," by F.-J. Chen et al., filed Aug. 15, 1997; U.S. Pat. No. 5,429,686, issued to Chiu et al. on Jul. 4, 1995; U.S. Pat. No. 5,399,412, issued to S. J. Sudall and S. A. Engel on Mar. 21, 1995; U.S. Pat. No. 5,672,248, issued to Wendt et al. on Sep. 30, 1997; and U.S. Pat. No. 5,607,551, issued to Farrington et al. on Mar. 4, 1997; all of which are herein incorporated in their entirety by reference. The molded tissue structures of the above patents can be especially helpful in providing good cleaning in a wet wipe. Good cleaning can also be promoted by providing a degree of texture in other substrates as well by embossing, molding, wetting and through-air drying on a textured fabric, and the like.

Airlaid material can be formed by metering an airflow containing the fibers and other optional materials, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. U.S. Pat. No. 31,775; U.S. Pat. No. 4,278,113 (Persson), issued Jul. 14, 1981; U.S. Pat. No. 4,264,289 (Day), issued Apr. 28, 1981; U.S. Pat. No. 4,352,649 (Jacobsen et al.), issued Oct. 5, 1982; U.S. Pat. No. 4,353,687 (Hosler, et al.), issued Oct. 12, 1982; U.S. Pat. No. 4,494,278 (Kroyer, et al.), issued Jan. 22, 1985; U.S. Pat. No. 4,627,806 (Johnson), issued Dec. 9, 1986; U.S. Pat. No. 4,650,409 (Nistri, et al.), issued Mar. 17, 1987; and U.S. Pat. No. 4,724,980 (Farley), issued Feb. 16, 1988; and U.S. Pat. No. 4,640,810 (Laursen et al.), issued Feb. 3, 1987.

The present invention also discloses how to make water-dispersible nonwovens, including cover stock (liner), intake (surge) materials and wet wipes, which are stable in fluids having a first ionic composition, such as monovalent ions at a particular concentration substantially greater than is found in typical hard water, using the above-described unique polymer formulations as binder compositions. The resultant nonwovens are flushable and water-dispersible due to the tailored ion sensitivity, which can be triggered regardless of the hardness of water found in toilets throughout the United States and the world. Dispersible products in accordance with the present invention also can have improved properties of softness and flexibility. Such products also have reduced stickiness. In some embodiments, the polymer formulations with which such articles are treated can have improved properties of sprayability, which improves polymer distribution on the product and penetration into the product, in addition to ease of application, which translates into cost savings.

The present invention further discloses an improved wetting composition for wet wipes. Wet wipes employing the polymer formulations of the present invention are stable during storage and retain a desired level of wet strength during use and are wetted with a wetting composition or cleaning agent that can be relatively free, or is substantially free, of organic solvents.

These features and advantages of the present invention will become apparent after a review of the following detailed description of the disclosed embodiments and the appended drawing and claims.

DETAILED DESCRIPTION OF THE DISCLOSED EMBODIMENTS

Figure 1:
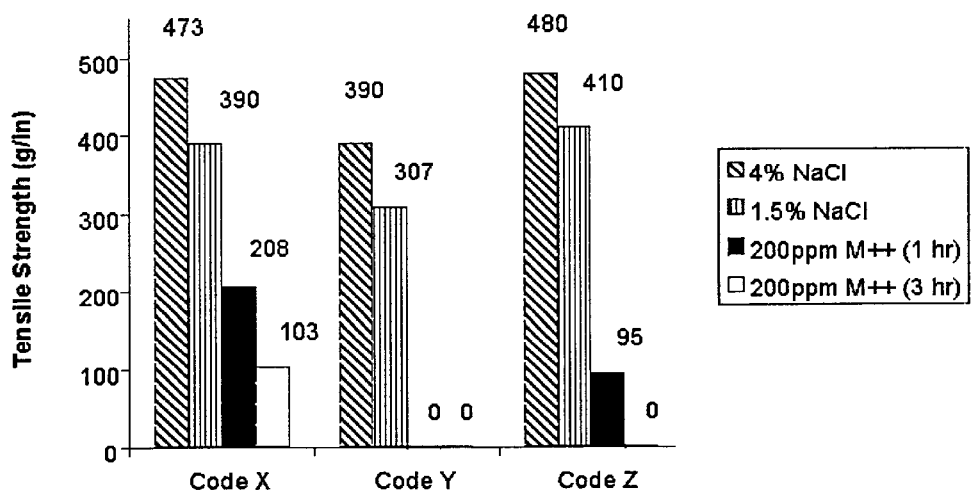
FIG. 1 is a graph that depicts wet strength data for three binder formulations as a function of ionic environment and soak time.

In order to be an effective ion-sensitive formulations suitable for use in flushable or water-dispersible personal care products, the formulations should desirably be (1) functional; i.e., maintain wet strength under controlled conditions and dissolve or disperse rapidly in soft or hard water such as found in toilets and sinks around the world; (2) safe (not toxic); and (3) relatively economical. In addition to the foregoing factors, the ion-sensitive formulations when used as a binder composition for a non-woven substrate, such as a wet wipe, desirably should be (4) processable on a commercial basis; i.e., may be applied relatively quickly on a large scale basis, such as by spraying, which thereby requires that the binder composition have a relatively low viscosity at high shear; (5) provide acceptable levels of sheet or substrate wettability; and (6) provide improved product feel, such as improved product flexibility and reduced stickiness. The wetting composition with which the wet wipes of the present invention are treated can provide some of the foregoing advantages, and, in addition, can provide one or more of (7) improved skin care, such as reduced skin irritation or other benefits, (8) improved tactile properties, and (9) promote good cleaning by providing a balance in use between friction and lubricity on the skin (skin glide). The ion-sensitive polymer formulations of the present invention and articles made therewith, especially wet wipes comprising particular wetting compositions set forth below, can meet many or all of the above criteria. Of course, it is not necessary for all of the advantages of the preferred embodiments of the present invention to be met to fall within the scope of the present invention.

The polymer formulations of the present invention may be formed from a single triggerable polymer, such as an ion-sensitive polymer, or from a combination of two or more different polymers, such as a triggerable polymer and a co-binder. Desirably, at least one polymer of the polymer formulations of the present invention is an ion-sensitive polymer. Ion-sensitive polymers are known in the art and include any polymer whose water solubility varies depending on the type and amount of ions present in water. Ion-sensitive polymers useful in the present invention include, but are not limited to the Lion polymers discussed above, such as the Lion acrylic acid terpolymer, the sulfonate anion modified acrylic acid terpolymer of the co-pending application Ser. No. 09/223,999 assigned to Kimberly Clark Worldwide, Inc.; the acrylic acid free polymers of the co-pending U.S. patent application Ser. No. 09/565,623, filed on May 4, 2000 and entitled "Ion-Sensitive Hard Water Dispersible Polymers and Applications Therefor" (identified as KC No. 15851; J&A No. 11302-0481; Express Mail Label No. EL498682165US), also assigned to Kimberly Clark Worldwide, Inc.; as well as, other ion- and chemical-sensitive polymers, including the polymers of U.S. Pat. No. 6,043,317, issued Mar. 28, 2000 to Mumick et al., and also assigned to Kimberly Clark Worldwide, Inc.; the disclosures of which are herein incorporated by reference in their entirety.

Other known triggerable polymers include temperature-sensitive and heat-sensitive polymers, as well as, polymers which become dispersible in the presence of a dispersion aid added to the water of a toilet bowl or other water source, as discussed in U.S. Pat. No. 5,948,710, issued Sep. 7, 1999 to Pomplun et al. and assigned to Kimberly Clark Worldwide, Inc., who note that another means for rendering a polymer degradable in water is through the use of temperature change. Certain polymers exhibit a cloud point temperature. As a result, these polymers will precipitate out of a solution at a particular temperature, which is the cloud point. These polymers can be used to form fibers, which are insoluble in water above a certain temperature, but which become soluble and thus degradable in water at a lower temperature. As a result, it is possible to select or blend a polymer, which will not degrade in body fluids, such as urine, at or near body temperature (37° C.) but which will degrade when placed in water at temperatures below body temperature, for example, at room temperature (23° C.). An example of such a polymer is polyvinylmethylether, which has a cloud point of 34° C. When this polymer is exposed to body fluids such as urine at 37° C., it will not degrade as this temperature is above its cloud point (34° C.). However, if the polymer is placed in water at room temperature (23° C.), the polymer will, with time, go back into solution as it is now exposed to water at a temperature below its cloud point. Consequently, the polymer will begin to degrade. Blends of polyvinylmethylether and copolymers may be considered as well. Other cold water soluble polymers include poly(vinyl alcohol) graft copolymers supplied by the Nippon Synthetic Chemical Company, Ltd. of Osaka, Japan, which are coded Ecomaty AX2000, AX10000 and AX300G.

Ion-Sensitive Polymers

The ion-sensitive Lion polymers and the ion-sensitive polymers of the above-referenced co-pending applications and U.S. patents of Kimberly-Clark Worldwide, Inc. are useful in the present invention. The sulfonate anion modified acrylic acid terpolymer of co-pending patent application Ser. No. 09/223,999, assigned to Kimberly-Clark Worldwide, Inc., are desired because, unlike the Lion Corp. polymers and other polymers cited in technical literature, the polymers of the co-pending application Ser. No. 09/223,999 are soluble in water having from less than about 10 ppm $Ca^{2+}$ and/or $Mg^{2+}$ up to about 200 ppm $Ca^{2+}$ and/or $Mg^{2+}$. The polymers of the co-pending application are formulated to minimize the potentially strong interaction between the anions of the polymers and the cations in the water. This strong interaction can be explained via the hard-soft acid-base theory proposed by R. G. Pearson in the *Journal of the American Chemical Society*, vol. 85, pg. 3533 (1963); or N. S. Isaacs in the textbook, *Physical Organic Chemistry*, published by Longman Scientific and Technical with John Wiley & Sons, Inc., New York (1987). Hard anions and hard cations interact strongly with one another. Soft anions and soft cations also interact strongly with one another. However, soft anions and hard cations, and vice-versa, interact weakly with one another. In the Lion polymers, the carboxylate anion of the sodium acrylate is a hard anion, which interacts strongly with the hard cations, $Ca^{2+}$ and/or $Mg^{2+}$, present in moderately hard and hard water. By replacing the carboxylate anions with a softer anion, such as a sulfonate anion, the interaction between the anions of an ion-triggerable polymer and the hard cations, $Ca^{2+}$ and/or $Mg^{2+}$, present in moderately hard and hard water, is reduced.

As used herein, the term "soft water" refers to water having a divalent ion content of less than about 10 ppm. As used herein, the term "moderately hard water" refers to water having a divalent ion content of from about 10 to about 50 ppm. As used herein, the term "hard water" refers to water having a divalent ion content of more than about 50 ppm up to about 200 ppm. By controlling the hydrophobic/hydrophilic balance and the composition of the polymers as well as the combination of polymers forming the formulation, the ion-sensitive polymer formulations having desired in-use binding strength and water-dispersibility in water are produced. The ion-sensitive polymer can be a copolymer, such as a terpolymer.

Ion-sensitive acrylic acid copolymers of the present invention may comprise any combination of acrylic acid monomers and acrylic ester (alkyl acrylate) monomers capable of free radical polymerization into a copolymer and, specifically, a terpolymer. Suitable acrylic acid monomers include, but are not limited to, acrylic acid and methacrylic acid. Suitable acrylic monomers include, but are not limited to, acrylic esters and methacrylic esters having an alkyl group of 1 to 18 carbon atoms or a cycloalkyl group of 3 to 18 carbon atoms and it is preferred that acrylic esters and/or methacrylic esters having a alkyl group of 1 to 12 carbon atoms or a cycloalkyl group of 3 to 12 carbon atoms be used singly or in combination. Other suitable monomers include, but are not limited to, acrylamide and methacrylamide based monomers, such as acrylamide, N,N-dimethyl acrylamide, N-ethyl acrylamide, N-isopropyl acrylamide, and hydroxymethyl acrylamide; N-vinylpyrrolidinone; N-vinylforamide; hydroxyalkyl acrylates and hydroxyalkyl methacrylates, such as hydroxyethyl methacrylate and hydroxyethyl acrylate. Other suitable acrylic acid monomers and acrylic ester monomers are disclosed in U.S. Pat. No. 5,317,063, assigned to Lion Corporation, Tokyo, Japan, the disclosure of which is incorporated herein by reference in its entirety. A particularly preferred acrylic acid terpolymer is LION SSB-3b, available from Lion Corporation. (In alternative embodiments, the ion-sensitive polymer is formed from monomers other than acrylic acid or its derivatives, or is relatively free of acrylic acid, methacrylic acid, and salts thereof.)

The relative amounts of the monomers in the acrylic acid copolymer of the present invention may vary depending on the desired properties in the resulting polymer. The mole percent of acrylic acid monomer in the copolymer is up to about 70 mole percent. More specifically, the mole percent of acrylic acid monomer in the copolymer is from about 15 to about 50 mole percent. Most specifically, the mole percent of acrylic acid monomer in the copolymer is from about 25 to about 40 mole percent.

More specifically, examples of the acrylic acid copolymers useful in the present invention include copolymers of 10 weight percent to 90 weight percent, desirably 20 weight percent to 70 weight percent of acrylic acid and/or methacrylic acid and 90 weight percent to 10 weight percent, desirably 80 weight percent to 30 weight percent of acrylic esters and/or methacrylic esters having an alkyl group of 1 to 18 carbon atoms or a cycloalkyl group of 3 to 18 carbon atoms in which 1 to 60 mole percent, desirably 5 to 50 mole percent of acrylic acid and/or methacrylic acid is neutralized to form a salt; or copolymers of 30 weight percent to 75 weight percent, desirably 40 weight percent to 65 weight percent of acrylic acid, 5 weight percent to 30 weight percent, desirably 10 weight percent to 25 weight percent of acrylic esters and/or methacrylic esters having an alkyl group of 8 to 12 carbon atoms and 20 weight percent to 40 weight percent; desirably 25 weight percent to 35 weight percent of acrylic esters and/or methacrylic esters having an alkyl group of 2 to 4 carbon atoms in which 1 to 50 mole percent, desirably 2 to 40 mole percent of acrylic acid is neutralized to form a salt.

The acrylic acid copolymers of the present invention may have an average molecular weight, which varies depending on the ultimate use of the polymer. The acrylic acid copolymers of the present invention have a weight average molecular weight ranging from about 10,000 to about 5,000,000. More specifically, the acrylic acid copolymers of the present invention have a weight average molecular weight ranging from about 25,000 to about 2,000,000, or, more specifically still, from about 200,000 to about 1,000,000.

The acrylic acid copolymers of the present invention may be prepared according to a variety of polymerization methods, desirably a solution polymerization method. Suitable solvents for the polymerization method include, but are not limited to, lower alcohols such as methanol, ethanol and propanol; a mixed solvent of water and one or more lower alcohols mentioned above; and a mixed solvent of water and one or more lower ketones such as acetone or methyl ethyl ketone.

In the polymerization methods of the present invention, any polymerization initiator may be used. Selection of a particular initiator may depend on a number of factors including, but not limited to, the polymerization temperature, the solvent, and the monomers used. Suitable polymerization initiators for use in the present invention include, but are not limited to, 2,2'-azobisisobutyronitrile, 2,2'-azobis(2-methylbutyronitrile), 2,2'-azobis(2,4-dimethylvaleronitrile), 2,2'-azobis(2-amidinopropane) dihydrochloride, 2,2'-azobis(N,N'-dimethyleneisobutylamidine), potassium persulfate, ammonium persulfate, and aqueous hydrogen peroxide. The amount of polymerization initiator may desirably range from about 0.01 to 5 weight percent based on the total weight of monomer present.

The polymerization temperature may vary depending on the polymerization solvent, monomers, and initiator used, but in general, ranges from about 20° C. to about 90° C. Polymerization time generally ranges from about 2 to about 8 hours.

The sulfonate anion modified acrylic acid copolymers in accordance with the present invention include hydrophilic monomers, such as acrylic acid or methacrylic acid, incorporated into the acrylic acid copolymers of the present invention along with one or more sulfonate-containing monomers. The sulfonate anions of these monomers are softer than carboxylate anions since the negative charge of the sulfonate anion is delocalized over three oxygen atoms and a larger sulfur atom, as opposed to only two oxygen atoms and a smaller carbon atom in the carboxylate anion. These monomers, containing the softer sulfonate anion, are less interactive with multivalent ions present in hard water, particularly $Ca^{2+}$ and $Mg^{2+}$ ions. Suitable sulfonate-containing monomers include, but are not limited to, 2-acrylamido-2-methyl-1-propanesulfonic acid (AMPS) and organic or inorganic salts of 2-acrylamido-2-methyl-1- propanesulfonic acid, such as alkali earth metal and organic amine salts of 2-acrylamido-2-methyl-1-propanesulfonic acid, particularly the sodium salt of 2-acrylamido-2-methyl-1-propanesulfonic acid (NaAMPS). Additional suitable sulfonate-containing monomers include, but are not limited to, 2-methyl-2-propene sulfonic acid, vinyl sulfonic acid, styrene sulfonic acid, 2-sulfopropyl methacrylate and 3-sulfopropyl acrylate, and organic or inorganic salts thereof, such as alkali earth metals and organic amine salts, such as alkyl ammonium hydroxide wherein the alkyl groups are $C_1$–$C_{18}$. To maintain the hydrophobic/hydrophilic balance of the ion-sensitive polymer, one or more hydrophobic monomers are added to the polymer.

The ion-sensitive sulfonate anion modified acrylic acid copolymers of the present invention may be produced from monomers including the following monomers: acrylic acid, methacrylic acid, or a combination thereof; 2-acrylamido-2-methyl-1-propanesulfonic acid (AMPS) and organic or inorganic salts thereof, such as the sodium salt thereof (NaAMPS); butyl acrylate; and 2-ethylhexyl acrylate. Desirably, the ion-sensitive sulfonate anion modified acrylic acid copolymers of the present invention are produced from: acrylic acid; AMPS, NaAMPS or a combination thereof; butyl acrylate; and 2-ethylhexyl acrylate. Desirably, the monomers are present in the sulfonate anion modified acrylic acid copolymer at the following mole percents: acrylic acid, about 35 to less than 80 mole percent; AMPS or NaAMPS, greater than 0 to about 20 mole percent; butyl acrylate, from greater than 0 to about 65 mole percent; and 2-ethylhexyl acrylate, from greater than 0 to about 45 mole percent. More specifically, the monomers are present in the sulfonate anion modified acrylic acid copolymer at the following mole percents: acrylic acid, about 50 to about 67 mole percent; AMPS or NaAMPS, from greater than 0 to about 10 mole percent; butyl acrylate, from about 15 to about 28 mole percent; and 2-ethylhexyl acrylate, from about 7 to about 15 mole percent. Most specifically, the monomers are present in the sulfonate anion modified acrylic acid copolymer at the following mole percents: acrylic acid, about 57 to about 66 mole percent; AMPS or NaAMPS, from about 1 to about 6 mole percent; butyl acrylate, from about 15 to about 28 mole percent; and 2-ethylhexyl acrylate, from about 7 to about 13 mole percent; especially, about 60 mole percent acrylic acid, about 5 mole percent AMPS or NaAMPS, about 24.5 mole percent butyl acrylate and about 10.5 mole percent 2-ethylhexyl acrylate.

If AMPS is used as one of the monomers, it is desired to neutralize at least a portion of the acid component. Any inorganic base or organic base may be used as a neutralizing agent to neutralize the acid component. Examples of neutralizing agents include, but are not limited to, inorganic bases, such as sodium hydroxide, potassium hydroxide, lithium hydroxide and sodium carbonate, and amines, such as monoethanolamine, diethanolamine, diethylaminoethanol, ammonia, trimethylamine, triethylamine, tripropylamine, morpholine. Preferred neutralizing agents include sodium hydroxide, potassium hydroxide, or a combination thereof.

A sulfonate modified copolymer having salt-sensitivity may also be produced by sulfonation of an existing polymer, such as a copolymer or acrylic acid-derived terpolymer. Methods of sulfonating polymers are well known in the art. Methods for the production of sulfonated or sulfated polymers are disclosed in U.S. Pat. No. 3,624,069, issued November 1971 to Schwelger; U.S. Pat. No. 4,419,403, issued Dec. 6, 1983 to Varona; U.S. Pat. No. 5,522,967, issued Jun. 4, 1996 to Shet; U.S. Pat. No. 4,220,739, issued Sep. 2, 1980 to Walles, U.S. Pat. No. 5,783,200, issued Jul. 21, 1998 to Motley et al., as well as the following patents: U.S. Pat. Nos. 2,400,720; 2,937,066; 2,786,780; 2,832,696; 3,613,957, and 3,740,258, all of which are herein incorporated by reference. Principles for sulfation and sulfonation (e.g., via sulfamic acid treatment, reaction with thionyl chloride or chlorosulfonic acid, or exposure to sulfur trioxide) are among the pathways disclosed by Samuel Shore and D. R. Berger in "Alcohol and Ether Alcohol Sulfates," in *Anionic Surfactants*, Part 1, ed. Warner M. Linfield, New York: Marcel Dekker, Inc., 1976, pp. 135–149; and by Ben E. Edwards, "The Mechanisms of Sulfonation and Sulfation," in *Anionic Surfactants*, Part 1, ed. Warner M. Linfield, New York: Marcel Dekker, Inc., 1976, pp. 111–134, both of which are herein incorporated by reference.

In a further embodiment of the present invention, the above-described ion-sensitive polymer formulations are used as binder materials for flushable and/or non-flushable products. In order to be effective as a binder material in flushable products throughout the United States, the ion-sensitive polymer formulations of the present invention remain stable and maintain their integrity while dry or in relatively low concentrations of monovalent ions, but become soluble in water containing up to about 200 ppm divalent ions, especially calcium and magnesium ions. Desirably, the ion-sensitive polymer formulations of the present invention including acrylic acid copolymers are insoluble in a salt solution containing at least about 0.3 weight percent of one or more inorganic and/or organic salts containing monovalent ions. More desirably, the ion-sensitive polymer formulations of the present invention including acrylic acid copolymers are insoluble in a salt solution containing from about 0.3 weight percent to about 5.0 weight percent of one or more inorganic and/or organic salts containing monovalent ions. Even more desirably, the ion-sensitive polymer formulations of the present invention including acrylic acid copolymers are insoluble in salt solutions containing from about 1 weight percent to about 3.0 weight percent of one or more inorganic and/or organic salts containing monovalent ions. Suitable monovalent ions include, but are not limited to, $Na^+$ ions, $K^+$ ions, $Li^+$ ions, $NH_4^+$ ions, low molecular weight quaternary ammonium compounds (e.g., those having fewer than 5 carbons on any side group), and a combination thereof.

In an alternate embodiment, the ion-sensitive polymer formulations of the present invention including sulfonate anion modified acrylic acid copolymers are insoluble in a salt solution containing at least about 1 weight percent of one or more inorganic and/or organic salts containing monovalent ions. More desirably, the ion-sensitive polymer formulations of the present invention including sulfonate anion modified acrylic acid terpolymers are insoluble in a salt solution containing from about 1 weight percent to about 5.0 weight percent of one or more inorganic and/or organic salts containing monovalent ions. Even more desirably, the ion-sensitive polymer formulations of the present invention including sulfonate anion modified acrylic acid terpolymers are insoluble in salt solutions containing from about 1 weight percent to about 3.0 weight percent of one or more inorganic and/or organic salts containing monovalent ions. Suitable monovalent ions include, but are not limited to, $Na^+$ ions, $K^+$ ions, $Li^+$ ions, $NH_4^+$ ions, low molecular weight quaternary ammonium compounds (e.g., those having fewer than 5 carbons on any side group), and a combination thereof Based on a recent study conducted by the American Chemical Society, water hardness across the United States varies greatly, with $CaCO_3$ concentration ranging from near zero for soft water to about 500 ppm $CaCO_3$ (about 200 ppm $Ca^{2+}$ ion) for very hard water. To ensure polymer formulation dispersibility across the country (and throughout the whole world), the ion-sensitive polymer formulations of the present invention are desirably soluble in water containing up to about 50 ppm $Ca^{2+}$ and/or $Mg^{2+}$ ions. More desirably, the ion-sensitive polymer formulations of the present invention are soluble in water containing up to about 100 ppm $Ca^{2+}$ and/or $Mg^{2+}$ ions. Even more desirably, the ion-sensitive polymer formulations of the present invention are soluble in water containing up to about 150 ppm $Ca^{2+}$ and/or $Mg^{2+}$ ions. Even more desirably, the ion-sensitive polymer formulations of the present invention are soluble in water containing up to about 200 ppm $Ca^{2+}$ and/or $Mg^{2+}$ ions.

A wide variety of polymer/surfactant systems may be used to provide the same functionality as the ion-sensitive Lion polymers and the ion-sensitive sulfonate anion modified acrylic acid terpolymers of co-pending patent application Ser. No. 09/223,999, without the need to be limited to sulfonic or carboxylic moieties. Such other systems are described below.

Phosphorylated polymers containing phosphonic groups, thiophsulphonic groups, or other organophosphorous groups as the "soft" anion capable of establishing a mismatch with $Ca^{++}$ may be used as the ion-sensitive polymer in the present invention. This can include modified cellulose or cellulose derivatives and related gums, made insoluble by the presence of monovalent salts or other electrolytes. In one embodiment, soluble cellulose derivatives, such as CMC, are phosphorylated and rendered insoluble and can be effective as ion-sensitive polymer formulations when in a solution of high ionic strength or of appropriate pH, but are dispersible in tap water. In another embodiment, aminophosphinic groups which can be anionic or amphoteric, are added to a polymer. Aminophosphinic groups can be added via condensation of a hypophosphite salt with a primary amine. Reaction of chloromethylphosphinic acid with amines can also yield useful anionic groups, as described by Guenther W. Wasow in "Phosphorous-Containing Anionic Surfactants," *Anionic Surfactants: Organic Chemistry*, ed. Helmut W. Stache, New York: Marcel Dekker, 1996, pp. 589–590. The entire chapter by Wasow, comprising pages 551–629 of the aforementioned book, offers additional teachings relevant to creating polymers with useful phosphorous groups, and is herein incorporated by reference.

Other methods of preparing phosphorylated cellulose fibers are well known. These methods may be adapted to CMC, which may then serve as a binder agent. Exemplary methods are disclosed in U.S. Pat. No. 3,739,782, issued Jun. 19, 1973 to Bemardin. Cellulose and synthetic or natural polymers modified to have other "soft" anionic groups can be useful as the ion-sensitive polymer of the present invention.

Natural polymers that are already provided with useful anionic groups also can be useful in the present invention. Such polymers include agar and carageenan, which have multiple ester sulfate groups. These may be further modified, if necessary, to have additional anionic groups (e.g., sulfonation, phosphorylation, and the like).

Polymers having two or more differing soft anionic groups, such as both sulfonic and phosphonic groups, wherein the relative amounts of the differing anions can be adjusted to optimize the strength, the ionic sensitivity, and the dispersibility of the polymer, are also useful in the present invention. This also includes zwitterionic and amphoteric compounds. Polyampholytes in particular can be readily soluble above or below the isoelectric point, but insoluble at the isoelectric point, offering the potential for a triggering mechanism based on electrolyte concentration and pH. Examples of polyampholytes include, but are not limited to, copolymers of methacrylic acid and allylamine, copolymers of methacrylic acid and 2-vinylpyridine, polysiloxane ionomers with pendant amphoteric groups, and polymers formed directly from zwitterionic monomeric salts, such as the ion-pair of co-monomers (IPC) of Salamone et al., all as disclosed by Irja Piirma in *Polymeric Surfactants*, New York: Marcel Dekker, Inc., 1992, at pp. 251–254, incorporated herein by reference.

Proteins capable of being salted out, optionally modified to have additional soft ionic groups, can be useful as the ion-sensitive polymer of the present invention.

Systems such as those comprising algin derivatives or natural sulfonated polymers in which calcium ion in high concentrations (much higher than the levels of 250 ppm or less that may be encountered in hard water) insolubilize the binder, but allow even hard water to sufficiently dilute the calcium ion to render the binder dispersible are useful in the present invention. Thus, while it is desired that the ion-sensitive binders of the present invention be insoluble in solutions comprising a monovalent metal ion above a critical concentration, in some embodiments useful ion-sensitive binders are insoluble in solutions comprising a divalent metal ion above a critical concentration, but become soluble when the divalent metal ion concentration falls to about 200 ppm or more specifically to about 100 ppm, such that a fibrous substrate with the ion-sensitive polymer as a binder maintains good wet strength in a solution comprising an elevated concentration of the divalent metal ion, yet becomes water dispersible in hard water or medium hard water. Thus, the triggering mechanism, which results in a pre-moistened wipe losing wet strength and becoming flushable even in hard water, can be due to the dilution of a monovalent or divalent metal ion, and particularly an alkali metal ion, with monovalent ions, such as sodium being preferred. Natural polymers and gums, which may be adapted for use as ion-sensitive binders, are described by R. L. Whistler and J. N. BeMiller in *Industrial Gums*, New York: Academic Press, Inc., 1973, incorporated herein by reference. Natural polymers, which become firm or form a gel in the presence of calcium ions, are described below.

Algin (which may need to be in the form of sodium alginate and calcium alginate for good dispersibility, based on reported behavior in use a binder for medicinal tablets—see p. 62 of Whistler and BeMiller), which is insoluble as alginic acid, calcium alginate, or in general as a salt of most polyvalent metals, but soluble as sodium alginate or as a salt with low-molecular-weight amines or quaternary ammonium compounds (p. 67) may be useful in the present invention. This material may be used, especially when zinc is an insolubilizing metal ion.

Other useful polymers include Carageenan and Iridophycan, both seaweed derivatives comprising ester sulfates.

Both natural polymers, including cellulose, and synthetic polymers can be provided with anionic groups, such as sulfonic groups, phosphonic groups, and carboxyl groups, capable of forming bridges to other molecules in the presence of ions of a suitable type and concentration. When the ionic concentration is substantially changed, such as by placing a cleansing article of the present invention in a toilet bowl, the article may become weak and disintegrate.

Ion-sensitive polymers include those which are dispersible in aqueous environment under prescribed conditions, yet are not dispersible in all aqueous environments. Examples include materials that are alkaline dispersible or saline insoluble. The Eastman AQ copolyesters (Eastman Chemical Company, Kingsport, Tenn.), for example, can be dispersible in deionized water yet insoluble in saline solutions. They have been proposed for use in articles such as diapers intended to absorb body fluids. Further information on those polymers is provided in European Patent Application 773,315-A1, "Nonwoven Web Comprising Water Soluble Polyamides and Articles Constructed Therefrom," published May 14, 1997 by S. U. Ahmed.

Useful polyampholytes include polyacrylamide-based copolymers which are highly sensitive to sodium chloride concentration.

U.S. Pat. No. 3,939,836, the disclosure of which is incorporated herein by reference, describes an alkali salt of a sulfated cellulose ester resin which gives good dry tensile strength to fabrics, which strength is retained in significant part when such fabrics are contacted with a salt solution typical of body fluids such as blood, menstrual fluid or urine and yet are readily dispersible in water. The resins have a degree of sulfate substitution of from 0.10 to 0.45. In U.S. Pat. No. 4,419,403, the disclosure of which is incorporated herein by reference, colloidal sulfate esters of cellulose are used for effective water-dispersible binders, wherein the binders have a much higher degree of sulfate substitution than the '836 patent. The binders of the '403 patent form gels in the presence of potassium ions. Other patents related to dispersible polymers and wet wipes include U.S. Pat. Nos. 4,117,187; 5,417,977; 4,309,469; 5,317,063; 5,312,883; 5,384,189; 5,543,488; 5,571,876; 5,709,940; 5,718,790, the disclosures of which are incorporated herein by reference.

Co-binder Polymers

As stated above, the polymer formulations of the present invention are formed from a single ion-sensitive polymer or a combination of two or more different polymers, wherein at least one polymer is an ion-sensitive polymer. The second polymer may be a co-binder polymer. A co-binder polymer is of a type and in an amount such that when combined with the ion-sensitive polymer, the co-binder polymer desirably is largely dispersed in the ion-sensitive polymer; i.e., the ion-sensitive polymer is desirably the continuous phase and the co-binder polymer is desirably the discontinuous phase. Desirably, the co-binder polymer can also meet several additional criteria. For example, the co-binder polymer can have a glass transition temperature; i.e., $T_g$, that is lower than the glass transition temperature of the ion-sensitive polymer. Furthermore or alternatively, the co-binder polymer can be insoluble in water, or can reduce the shear viscosity of the ion-sensitive polymer. The co-binder can be present at a level relative to the solids mass of the triggerable polymer of about 45% or less, specifically about 30% or less, more specifically about 20% or less, more specifically still about 15% or less, and most specifically about 10% or less, with exemplary ranges of from about 1% to about 45% or from about 25% to about 35%, as well as from about 1% to about 20% or from about 5% to about 25%. The amount of co-binder present should be low enough, for co-binders with the potential to form water insoluble bonds or films, that the co-binder remains a discontinuous phase unable to create enough crosslinked, or insoluble bonds, to jeopardize the dispersibility of the treated substrate. In one embodiment, the ion-sensitive polymer formulation of the present invention can comprise about 75 weight percent acrylic acid terpolymer and about 25 weight percent poly(ethylene-vinyl acetate) co-binder.

Desirably, but not necessarily, the co-binder polymer when combined with the ion-sensitive polymer will reduce the shear viscosity of the ion-sensitive polymer to such an extent that the combination of the ion-sensitive polymer and the co-binder polymer is sprayable. By sprayable is mean that the polymer can be applied to a nonwoven fibrous substrate by spraying and the distribution of the polymer across the substrate and the penetration of the polymer into the substrate are such that the polymer formulation is uniformly applied to the substrate.

The co-binder polymer can be in the form of an emulsion latex. The surfactant system used in such a latex emulsion should be such that it does not substantially interfere with the dispersibility of the ion-sensitive polymer.

In some embodiments, the combination of the ion-sensitive polymer and the co-binder polymer reduces the stiffness of the article to which it is applied compared to the article with just the ion-sensitive polymer. It has been found that when the ion-sensitive polymer, such as a sulfonate anion modified acrylic acid terpolymer, is applied to a nonwoven substrate, such as an air laid layer of wood pulp, for the purpose of forming a wet wipe, the nonwoven sheet can have an undesirable amount of stiffness that is detrimental to the dry product feel or to the handling of the dry web during processing, when the brittleness of the dry substrate can harm runnability. By combining the ion-sensitive polymer and the co-binder polymer, the stiffness of such articles can be reduced.

The co-binder polymer of the present invention can have an average molecular weight, which varies depending on the ultimate use of the polymer. Desirably, the co-binder polymer has a weight average molecular weight ranging from about 500,000 to about 200,000,000. More desirably, the co-binder polymer has a weight average molecular weight ranging from about 500,000 to about 100,000,000.

Co-binder polymers that can meet many or all of the foregoing criteria include, but are not limited to, poly(ethylene-vinyl acetate), poly(styrene-butadiene), poly(styrene-acrylic), a vinyl acrylic terpolymer, neoprene, a polyester latex, an acrylic emulsion latex, poly vinyl chloride, ethylene-vinyl chloride copolymer, a carboxylated vinyl acetate latex, and the like, all of which can be non-crosslinking (e.g., devoid of N-methylol acrylamide or other crosslinkers), crosslinking, or potentially crosslinking (i.e., prepared with a crosslinker present) but not substantially crosslinked in the final product.

A particularly preferred non-crosslinking poly(ethylene-vinyl acetate) is Dur-O-Set® RB available from National Starch and Chemical Co., Bridgewater, N.J. A particularly preferred non-crosslinking poly(styrene-butadiene) is Rovene® 4817 available from Mallard Creek Polymers, Charlotte, N.C. A particularly preferred non-crosslinking poly(styrene-acrylic) is Rhoplex® NM 1715K available from Rohm and Haas, Philadelphia, Pa.

When a latex co-binder, or any potentially crosslinkable co-binder is used, the latex should be prevented from forming substantial water-insoluble bonds that bind the fibrous substrate together and interfere with the dispersibility of the article. Thus, the latex can be free of crosslinking agents, such as NMA, or free of catalyst for the crosslinker, or both. Alternatively, an inhibitor can be added that interferes with the crosslinker or with the catalyst such that crosslinking is impaired even when the article is heated to normal crosslinking temperatures. Such inhibitors can include free radical scavengers, methyl hydroquinone, t-butylcatechol, pH control agents such as potassium hydroxide, and the like. For some latex crosslinkers, such as N-methylol-acrylamide (NMA), for example, elevated pH such as a pH of 8 or higher can interfere with crosslinking at normal crosslinking temperatures (e.g., about 130° C. or higher). Also alternatively, an article comprising a latex co-binder can be maintained at temperatures below the temperature range at which crosslinking takes place, such that the presence of a crosslinker does not lead to crosslinking, or such that the degree of crosslinking remains sufficiently low that the dispersibility of the article is not jeopardized. Also alternatively, the amount of crosslinkable latex can be kept below a threshold level such that even with crosslinking, the article remains dispersible. For example, a small quantity of crosslinkable latex dispersed as discrete particles in an ion-sensitive binder can permit dispersibility even when fully crosslinked. For the later embodiment, the amount of latex can be below about 20 weight percent, and, more specifically, below about 15 weight percent relative to the ion-sensitive binder.

Latex compounds, whether crosslinkable or not, need not be the co-binder. SEM micrography of successful ion-sensitive binder films with useful non-crosslinking latex emulsions dispersed therein has shown that the latex co-binder particles can remain as discrete entities in the ion-sensitive binder, possibly serving in part as filler material. It is believed that other materials could serve a similar role, including a dispersed mineral or particulate filler in the ion-sensitive binder, optionally comprising added surfactants/dispersants. For example, in one envisioned embodiment, freeflowing Ganzpearl PS-8F particles from Presperse, Inc. (Piscataway, N.J.), a styrene/divinylbenzene copolymer with about 0.4 micron particles, can be dispersed in an ion-sensitive binder at a level of about 2 to 10 weight percent to modify the mechanical, tactile, and optical properties of the ion-sensitive binder. Other filler-like approaches could include microparticles, microspheres, or microbeads of metal, glass, carbon, mineral, quartz, and/or plastic, such as acrylic or phenolic, and hollow particles having inert gaseous atmospheres sealed within their interiors. Examples include EXPANCEL phenolic microspheres from Expancel of Sweden, which expand substantially when heated, or the acrylic microspheres known as PM 6545 available from PQ Corporation of Pennsylvania. Foaming agents, including $CO_2$ dissolved in the ion-sensitive binder, could also provide helpful discontinuities as gas bubbles in the matrix of an ion-sensitive binder, allowing the dispersed gas phase in the ion-sensitive binder to serve as the co-binder. In general, any compatible material that is not miscible with the binder, especially one with adhesive or binding properties of its own, can be used as the co-binder, if it is not provided in a state that imparts substantial covalent bonds joining fibers in a way that interferes with the water-dispersibility of the product. However, those materials that also provide additional benefits, such as reduced spray viscosity, can be especially preferred. Adhesive co-binders, such as latex that do not contain crosslinkers or contain reduced amounts of crosslinkers, have been found to be especially helpful in providing good results over a wide range of processing conditions, including drying at elevated temperatures.

As stated above, the $T_g$ of the co-binder polymer can be lower than the $T_g$ of the ion-sensitive polymer, which is believed to improve the flexibility of the treated substrate, especially in the dry state. In Table 1 shown below is a comparison of the glass transition temperature of some of the preferred polymers useful in the present invention.

TABLE 1

Glass Transition Temperatures For Select Polymers

| Polymer | Glass Transition Temperature - Tg |
|---|---|
| Sulfonate anion modified acrylic acid terpolymer (dry) | 55° C. |
| Sulfonate anion modified acrylic acid terpolymer (wet) | −22° C. |
| Rhoplex NW 1715K (dry) | −6° C. |
| Rovene 4817 (dry) | −4° C. |
| Elite 33 (dry) | 10° C. |
| Elite 22 (dry) | −15° C. |

In an alternate embodiment, the ion-sensitive polymer formulation of the present invention comprises about 55 to about 95 weight percent sulfonate anion modified acrylic acid terpolymer and about 5 to about 45 weight percent poly(ethylene-vinyl acetate). More desirably, the ion-sensitive polymer formulation of the present invention comprises about 75 weight percent sulfonate anion modified acrylic acid terpolymer and about 25 weight percent poly(ethylene-vinyl acetate).

As stated above, useful co-binder polymers can include a variety of commercial latex emulsions, including those selected from the Rovene® series (styrene butadiene latices available from Mallard Creek Polymers of Charlotte, N.C.), the Rhoplex® latices of Rohm and Haas Company, and the Elite® latices of National Starch. Polymer emulsions or dispersions generally comprise small polymer particles, such as crosslinkable ethylene vinyl acetate copolymers, typically in spherical form, dispersed in water and stabilized with surface active ingredients such as low molecular weight emulsifiers or high molecular weight protective colloids. These liquid binders can be applied to airlaid webs or other substrates by methods known in the art of binder treatment for nonwoven webs, including spray or foam application, flooded nip impregnation, curtain coating, etc., followed by drying. In general, a wide variety of latex compounds and other resins or emulsions can be considered, including vinyl acetate copolymer latices, such as 76 RES 7800 from Union Oil Chemicals Divisions and Resyn® 25-1103, Resyn® 25-1109, Resyn® 25-1119, and Resyn® 25-1189 from National Starch and Chemical Corporation, ethylene-vinyl acetate copolymer emulsions, such as Airflex® ethylene-vinylacetate from Air Products and Chemicals Inc., acrylic-vinyl acetate copolymer emulsions, such as Rhoplex® AR-74 from Rohm and Haas Company, Synthemul® 97-726 from Reichhold Chemicals Inc., Resyn® 25-1140, 25-1141, 25-1142, and Resyn-6820 from National Starch and Chemical Corporation, vinyl acrylic terpolymer latices, such as 76 RES 3103 from Union Oil Chemical Division, and Resyn® 251110 from National Starch and Chemical Corporation, acrylic emulsion latices, such as Rhoplex® B-15J, Rhoplex® P-376, Rhoplex® TR-407, Rhoplex® E-940, Rhoplex® TR934, Rhoplex® TR-520, Rhoplex® HA-24, and Rhoplex® NW1825 from Rohm and Haas Company, and Hycar® 2600 X 322, Hycar® 2671, Hycar® 2679, Hycar® 26120, and Hycar® 2600 X347 from B. F. Goodrich Chemical Group, styrene-butadiene latices, such as 76 RES 4100 and 76 RES 8100 available from Union Oil Chemicals Division, Tylac® resin emulsion 68-412, Tylac® resin emulsion 68-067, 68-319, 68-413, 68-500, 68-501, available from Reichhold Chemical Inc., and DL6672A, DL6663A, DL6638A, DL6626A, DL6620A, DL615A, DL617A, DL620A, DL640A, DL650A available from Dow Chemical Company; and rubber latices, such as neoprene available from Serva Biochemicals; polyester latices, such as Eastman AQ 29D available from Eastman Chemical Company; vinyl chloride latices, such as Geon® 352 from B. F. Goodrich Chemical Group; ethylene-vinyl chloride copolymer emulsions, such as Airflex® ethylene-vinyl chloride from Air Products and Chemicals; polyvinyl acetate homopolymer emulsions, such as Vinac® from Air Products and Chemicals; carboxylated vinyl acetate emulsion resins, such as Synthemul® synthetic resin emulsions 40-502, 40-503, and 97-664 from Reichhold Chemicals Inc. and Polyco® 2149, 2150, and 2171 from Rohm and Haas Company. Silicone emulsions and binders can also be considered.

The co-binder polymer can comprise surface active compounds that improve the wettability of the substrate after application of the binder mixture.

Wettability of a dry substrate that has been treated with a ion-sensitive polymer formulation can be a problem in some embodiments, because the hydrophobic portions of the ion-sensitive polymer formulation can become selectively oriented toward the air phase during drying, creating a hydrophobic surface that can be difficult to wet when the wetting composition is later applied unless surfactants are added to the wetting composition. Surfactants, or other surface active ingredients, in co-binder polymers can improve the wettability of the dried substrate that has been treated with a ion-sensitive polymer formulation. Surfactants in the co-binder polymer should not significantly interfere with the ion-sensitive polymer formulation. Thus, the binder should maintain good integrity and tactile properties in the pre-moistened wipes with the surfactant present.

In one embodiment, an effective co-binder polymer replaces a portion of the ion-sensitive polymer formulation and permits a given strength level to be achieved in a pre-moistened wipe with at least one of lower stiffness, better tactile properties (e.g., lubricity or smoothness), or reduced cost, relative to an otherwise identical pre-moistened wipe lacking the co-binder polymer and comprising the ion-sensitive polymer formulation at a level sufficient to achieve the given tensile strength.

Other Co-binder Polymers

The Dry Emulsion Powder (DEP) binders of Wacker Polymer Systems (Burghausen, Germany) such as the VIN-NEK® system of binders, can be applied in some embodiments of the present invention. These are redispersible, free flowing binder powders formed from liquid emulsions. Small polymer particles from a dispersion are provided in a protective matrix of water soluble protective colloids in the form of a powder particle. The surface of the powder particle is protected against caking by platelets of mineral crystals. As a result, polymer particles that once were in a liquid dispersion are now available in a free flowing, dry powder form that can be redispersed in water or turned into swollen, tacky particles by the addition of moisture. These particles can be applied in highloft nonwovens by depositing them with the fibers during the airlaid process, and then later adding 10% to 30% moisture to cause the particles to swell and adhere to the fibers. This can be called the "chewing gum effect," meaning that the dry, non-tacky fibers in the web become sticky like chewing gum once moistened. Good adhesion to polar surfaces and other surfaces is obtained. These binders are available as free flowing particles formed from latex emulsions that have been dried and treated with agents to prevent cohesion in the dry state. They can be entrained in air and deposited with fibers during the airlaid process, or can be applied to a substrate by electrostatic means, by direct contact, by gravity feed devices, and other means. They can be applied apart from the binder, either before or after the binder has been dried. Contact with moisture, either as liquid or steam, rehydrates the latex particles and causes them to swell and to adhere to the fibers. Drying and heating to elevated temperatures (e.g., above 160° C.) causes the binder particles to become crosslinked and water resistant, but drying at lower temperatures (e.g., at 110° C. or less) can result in film formation and a degree of fiber binding without seriously impairing the water dispersibility of the pre-moistened wipes. Thus, it is believed that the commercial product can be used without reducing the amount of crosslinker by controlling the curing of the co-binder polymer, such as limiting the time and temperature of drying to provide a degree of bonding without significant crosslinking.

As pointed out by Dr. Klaus Kohlhammer in "New Airlaid Binders," *Nonwovens Report International,* September 1999, issue 342, pp. 20–22, 28–31, dry emulsion binder powders have the advantage that they can easily be incorporated into a nonwoven or airlaid web during formation of the web, as opposed to applying the material to an existing substrate, permitting increased control over placement of the co-binder polymer. Thus, a nonwoven or airlaid web can be prepared already having dry emulsion binders therein, followed by moistening when the ion-sensitive polymer formulation solution is applied, whereupon the dry emulsion powder becomes tacky and contributes to binding of the substrate. Alternatively, the dry emulsion powder can be entrapped in the substrate by a filtration mechanism after the substrate has been treated with ion-sensitive binder and dried, whereupon the dry emulsion powder is rendered tacky upon application of the wetting composition.

In another embodiment, the dry emulsion powder is dispersed into the ion-sensitive polymer formulation solution either by application of the powder as the ion-sensitive polymer formulation solution is being sprayed onto the web or by adding and dispersing the dry emulsion powder particles into the ion-sensitive polymer formulation solution, after which the mixture is applied to a web by spraying, by foam application methods, or by other techniques known in the art.

Binder Formulations and Fabrics Containing the Same

The polymer formulations of the present invention may be used as binders. The binder formulations of the present invention may be applied to any fibrous substrate. The binders are particularly suitable for use in water-dispersible products. Suitable fibrous substrates include, but are not limited to, nonwoven and woven fabrics. In many embodiments, particularly personal care products, preferred substrates are nonwoven fabrics. As used herein, the term "nonwoven fabric" refers to a fabric that has a structure of individual fibers or filaments randomly arranged in a mat-like fashion (including papers). Nonwoven fabrics can be made from a variety of processes including, but not limited to, air-laid processes, wet-laid processes, hydroentangling processes, staple fiber carding and bonding, and solution spinning.

The binder composition may be applied to the fibrous substrate by any known process of application. Suitable processes for applying the binder material include, but are not limited to, printing, spraying, electrostatic spraying, coating, flooded nips, metered press rolls, impregnating or by any other technique. The amount of binder composition may be metered and distributed uniformly within the fibrous substrate or may be non-uniformly distributed within the fibrous substrate. The binder composition may be distributed throughout the entire fibrous substrate or it may be distributed within a multiplicity of small closely spaced areas. In most embodiments, uniform distribution of binder composition is desired.

For ease of application to the fibrous substrate, the binder may be dissolved in water, or in a non-aqueous solvent such as methanol, ethanol, acetone, or the like, with water being the preferred solvent. The amount of binder dissolved in the solvent may vary depending on the polymer used and the fabric application. Desirably, the binder solution contains up to about 25 percent by weight of binder composition solids. More desirably, the binder solution contains from about 10 to 20 percent by weight of binder composition solids, especially about 12 percent by weight binder composition solids. Plasticizers, perfumes, coloring agents, antifoams, bactericides, preservative, surface active agents, thickening agents, fillers, opacifiers, tackifiers, detackifiers, and similar additives can be incorporated into the solution of binder components, if so desired.

Once the binder composition is applied to the substrate, the substrate is dried by any conventional means. Once dry, the coherent fibrous substrate exhibits improved tensile strength when compared to the tensile strength of the untreated wet-laid or dry-laid substrates, and yet has the ability to rapidly "fall apart", or disintegrate when placed in soft or hard water having a relatively high multivalent ionic concentration and agitated. For example, the dry tensile strength of the fibrous substrate may be increased by at least 25 percent as compared to the dry tensile strength of the untreated substrate not containing the binder. More particularly, the dry tensile strength of the fibrous substrate may be increase by at least 100 percent as compared to the dry tensile strength of the untreated substrate not containing the binder. Even more particularly, the dry tensile strength of the fibrous substrate may be increased by at least 500 percent as compared to the dry tensile strength of the untreated substrate not containing the binder.

A desirable feature of the present invention is that the improvement in tensile strength is effected where the amount of binder composition present, "add-on", in the resultant fibrous substrate represents only a small portion by weight of the entire substrate. The amount of "add-on" can vary for a particular application; however, the optimum amount of "add-on" results in a fibrous substrate which has integrity while in use and also quickly disperses when agitated in water. For example, the binder components typically are from about 5 to about 65 percent, by weight, of the total weight of the substrate. More particularly, the binder components may be from about 10 to about 35 percent, by weight, of the total weight of the substrate. Even more particularly, the binder components may be from about 17 to about 22 percent by weight of the total weight of the substrate.

The nonwoven fabrics of the present invention have good in-use tensile strength, as well as, ion triggerability. Desirably, the nonwoven fabrics of the present invention are abrasion resistant and retain significant tensile strength in aqueous solutions containing greater than about 0.3 weight percent NaCl, or a mixture of monovalent ions, for those formulations using the acrylic acid terpolymer, and greater than about 1 weight percent NaCl, or a mixture of monovalent ions, for those formulations using the sulfonate anion modified acrylic acid terpolymer. Yet, the nonwoven fabrics are dispersible in very soft to moderately hard to hard water. Because of this latter property, nonwoven fabrics of the present invention are well suited for disposable products, such as sanitary napkins, diapers, adult incontinence products, and dry and premoistened wipes (wet wipes), which can be thrown in a flush toilet after use in any part of the world.

The fibers forming the fabrics above can be made from a variety of materials including natural fibers, synthetic fibers, and combinations thereof. The choice of fibers depends upon, for example, the intended end use of the finished fabric and fiber cost. For instance, suitable fibrous substrates may include, but are not limited to, natural fibers such as cotton, linen, jute, hemp, wool, wood pulp, etc. Similarly, regenerated cellulosic fibers, such as viscose rayon and cuprammonium rayon, modified cellulosic fibers, such as cellulose acetate, or synthetic fibers, such as those derived from polypropylenes, polyethylenes, polyolefins, polyesters, polyamides, polyacrylics, etc., alone or in combination with one another, may likewise be used. Blends of one or more of the above fibers may also be used, if so desired. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Mercerized, chemically stiffened or crosslinked fibers may also be used.

Synthetic cellulose fiber types include rayon in all its varieties and other fibers derived from viscose or chemically modified cellulose, including regenerated cellulose and solvent-spun cellulose, such as Lyocell. Chemically treated natural cellulosic fibers can be used, such as mercerized pulps, chemically stiffened or crosslinked fibers, or sulfonated fibers. Recycled fibers, as well as virgin fibers, can be used. Cellulose produced by microbes and other cellulosic derivatives can be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. The fiber length is important in producing the fabrics of the present invention. In some embodiments, such as flushable products, fiber length is of more importance. The minimum length of the fibers depends on the method selected for forming the fibrous substrate. For example, where the fibrous substrate is formed by carding, the length of the fiber should usually be at least about 42 mm in order to insure uniformity.

Where the fibrous substrate is formed by air-laid or wet-laid processes, the fiber length may desirably be about 0.2 to 6 mm. Although fibers having a length of greater than 50 mm are within the scope of the present invention, it has been determined that when a substantial quantity of fibers having a length greater than about 15 mm is placed in a flushable fabric, though the fibers will disperse and separate in water, their length tends to form "ropes" of fibers, which are undesirable when flushing in home toilets. Therefore, for these products, it is desired that the fiber length be about 15 mm or less so that the fibers will not have a tendency to "rope" when they are flushed through a toilet. Although fibers of various lengths are applicable in the present invention, desirably fibers are of a length less than about 15 mm so that the fibers disperse easily from one another when in contact with water. The fibers, particularly synthetic fibers, can also be crimped The fabrics of the present invention may be formed from a single layer or multiple layers. In the case of multiple layers, the layers are generally positioned in a juxtaposed or surface-to-surface relationship and all or a portion of the layers may be bound to adjacent layers. Nonwoven webs of the present invention may also be formed from a plurality of separate nonwoven webs wherein the separate nonwoven webs may be formed from single or multiple layers. In those instances where the nonwoven web includes multiple layers, the entire thickness of the nonwoven web may be subjected to a binder application or each individual layer may be separately subjected to a binder application and then combined with other layers in a juxtaposed relationship to form the finished nonwoven web.

In one embodiment, the fabric substrates of the present invention may be incorporated into cleansing and body fluid absorbent products, such as sanitary napkins, diapers, adult incontinence products, surgical dressings, tissues, wet wipes, and the like. These products may include an absorbent core, comprising one or more layers of an absorbent fibrous material. The core may also comprise one or more layers of a fluid-pervious element, such as fibrous tissue, gauze, plastic netting, etc. These are generally useful as wrapping materials to hold the components of the core together. Additionally, the core may comprise a fluid-impervious element or barrier means to preclude the passage of fluid through the core and on the outer surfaces of the product. Desirably, the barrier means also is water-dispersible. A film of a polymer having substantially the same composition as the aforesaid water-dispersible binder is particularly well-suited for this purpose. In accordance with the present invention, the polymer compositions are useful for forming each of the above-mentioned product components including the layers of absorbent core, the fluid-pervious element, the wrapping materials, and the fluid-impervious element or barrier means.

The binder formulations of the present invention are particularly useful for binding fibers of air-laid nonwoven fabrics. These air-laid materials are useful for body-side liners, fluid distribution materials, fluid in-take materials, such as a surge material, absorbent wrap sheet and cover stock for various water-dispersible personal care products. Air-laid materials are particularly useful for use as a pre-moistened wipe (wet wipe). The basis weights for air-laid non-woven fabrics may range from about 20 to about 200 grams per square meter ("gsm") with staple fibers having a denier of about 0.5–10 and a length of about 6–15 millimeters. Surge, or in-take, materials need better resiliency and higher loft so staple fibers having about 6 denier or greater are used to make these products. A desirable final density for the surge, or in-take, materials is between about 0.025 grams per cubic centimeter ("g/cc") to about 0.10 g/cc. Fluid distribution materials may have a higher density, in the desired range of about 0.10 to about 0.20 g/cc using fibers of lower denier, most desirable fibers have a denier of less than about 1.5. Wipes generally can have a fiber density of about 0.025 g/cc to about 0.2 g/cc and a basis weight of about 20 gsm to about 150 gsm; specifically from about 30 to about 90 gsm, and most specifically from about 60 gsm to about 65 gsm.

The nonwoven fabrics of the present invention may also be incorporated into such body fluid absorbing products as sanitary napkins, diapers, surgical dressings, tissues and the like. In one embodiment, the binder is such that it will not dissolve when contacted by body fluids since the concentration of monovalent ions in the body fluids is above the level needed for dissolution; i.e., greater that 0.3% by weight and/or greater than 1% by weight. The nonwoven fabric retains its structure, softness and exhibits a toughness satisfactory for practical use. However, when brought into contact with water having a concentration of multivalent ions, such as $Ca^{2+}$ and $Mg^{2+}$ ions, of up to about 200 ppm, the binder, such as one comprising a sulfonate anion modified acrylic acid terpolymer, disperses. Similarly, when brought into contact with water having a concentration of multivalent ions, such as $Ca^{2+}$ and $Mg^{2+}$ ions, of less than about 10 ppm, the binder comprising the acrylic acid terpolymer disperses. The nonwoven fabric structure is then easily broken and dispersed in the water.

In one embodiment of the present invention, the in-use tensile strength of a nonwoven fabric is enhanced by forming the nonwoven fabric with a binder material comprising an ion-sensitive polymer formulation of the present invention and subsequently applying one or more monovalent and/or multivalent salts to the nonwoven fabric. The salt may be applied to the nonwoven fabric by any method known to those of ordinary skill in the art including, but not limited to, applying a solid powder onto the fabric and spraying a salt solution onto the fabric. The amount of salt may vary depending on a particular application. However, the amount of salt applied to the fabric is typically from about 0.1 weight percent to about 10 weight percent salt solids based on the total weight of the fabric. The salt-containing fabrics of the present invention may be used in a variety of fabric applications including, but not limited to, feminine pads, surgical dressings, and diapers.

Those skilled in the art will readily understand that the binder formulations and fibrous substrates of the present invention may be advantageously employed in the preparation of a wide variety of products, including but not limited to, absorbent personal care products designed to be contacted with body fluids. Such products may only comprise a single layer of the fibrous substrate, or may comprise a combination of elements, as described above. Although the binder formulations and fibrous substrates of the present invention are particularly suited for personal care products, the binder formulations and fibrous substrates may be advantageously employed in a wide variety of consumer products.

The combination of the acrylic acid terpolymer or the sulfonate anion modified acrylic acid terpolymer and the non-crosslinking poly(ethylene-vinyl acetate) of the present invention produces improved results over the use of the terpolymer alone. For example, when the ion-sensitive polymer formulation of the present invention is used for a binder composition for wet wipes, the wet wipes have improved wettability on first insult without losing dispersibility which allows the wipe basesheet to wet out easily with the wet wipe solution at commercial speeds. The ion-sensitive polymer formulation of the present invention also can reduce the stiffness of the dry basesheet, improve the runnability of the dry and otherwise brittle sheet during further conversion of the product, reduce the stickiness of the wipes and/or improve the sprayability of the ion-sensitive binder, thereby improving binder distribution and penetration in the basesheet.

Unlike other binder systems known in the art, the ion-sensitive polymer formulations of the present invention can be activated as binders without the need for elevated temperature. While drying or water removal is useful in achieving a good distribution of the binder in a fibrous web, elevated temperature, per se, is not essential because the binder does not require crosslinking or other chemical reactions with high activation energy to serve as a binder. Rather, the interaction with a soluble activating compound, typically a salt, is sufficient to cause the binder to become active (insoluble) or "salted out." Thus, a drying step can be avoided, if desired, or replaced with low-temperature water removal operations such as room-temperature drying or freeze drying. Elevated temperature is generally helpful for drying, but the drying can be done at temperatures below what is normally needed to drive crosslinking reactions.

Thus, the peak temperature to which the substrate is exposed or to which the substrate is brought can be below any of the following: 180° C., 160° C., 140° C., 120° C., 110° C., 105° C., 100° C., 90° C., 75° C., and 60° C., with an exemplary range for peak web temperature of from about 50° C. to about 110° C., or from about 70° C. to about 140° C. Of course, higher temperatures can be used, but are not necessary in most embodiments. While co-binder polymer systems, such as commercial latex emulsions, may also comprise crosslinkers suited for reaction at temperatures of 1600 C. or higher, maintaining a lower peak temperature can be beneficial in preventing development of excessive strength in the co-binder polymer that might otherwise hinder the water dispersibility of the pre-moistened wipe.

Wet Wipe Wetting Composition and Wet Wipes Containing the Same

One particularly interesting embodiment of the present invention is the production of pre-moistened wipes, or wet wipes, from the above-described ion-sensitive binder compositions and fibrous materials. For wipes, the fibrous material may be in the form of a woven or nonwoven fabric; however, nonwoven fabrics are more desirable. The nonwoven fabric is, desirably, formed from relatively short fibers, such as wood pulp fibers. The minimum length of the fibers depends on the method selected for forming the nonwoven fabric. Where the nonwoven fabric is formed by a wet or dry method, the fiber length is desirably from about 0.1 millimeters to 15 millimeters. Desirably, the nonwoven fabric of the present invention has a relatively low wet cohesive strength when it is not bonded together by an adhesive or binder material. When such nonwoven fabrics are bonded together by a binder composition, which loses its bonding strength in tap water and in sewer water, the fabric will break up readily by the agitation provided by flushing and moving through the sewer pipes.

The finished wipes may be individually packaged, desirably in a folded condition, in a moisture proof envelope or packaged in containers holding any desired number of sheets in a water-tight package with a wetting composition applied to the wipe. The finished wipes may also be packaged as a roll of separable sheets in a moisture-proof container holding any desired number of sheets on the roll with a wetting composition applied to the wipes. The roll can be coreless and either hollow or solid. Coreless rolls, including rolls with a hollow center or without a solid center, can be produced with known coreless roll winders, including those of SRP Industry, Inc. (San Jose, Calif.); Shimizu Manufacturing (Japan), and the devices disclosed in U.S. Pat. No. 4,667,890, issued May 26, 1987 to Gietman. Solid-wound coreless rolls can offer more product for a given volume and can be adapted for a wide variety of dispensers.

Relative to the weight of the dry fabric, the wipe may desirably contain from about 10 percent to about 400 percent of the wetting composition, more desirably from about 100 percent to about 300 percent of the wetting composition, and even more desirably from about 180 percent to about 240 percent of the wetting composition. The wipe maintains its desired characteristics over the time periods involved in warehousing, transportation, retail display and storage by the consumer. Accordingly, shelf life may range from two months to two years.

Various forms of impermeable envelopes and storage means for containing wet-packaged materials such as wipes and towelettes and the like are well known in the art. Any of these may be employed in packaging the pre-moistened wipes of the present invention.

Desirably, the pre-moistened wipes of the present invention are wetted with an aqueous wetting composition, which has one or more of the following properties:

(1) is compatible with the above-described ion-sensitive binder compositions of the present invention;
(2) enables the pre-moistened wipe to maintain its wet strength during converting, storage and usage (including dispensing), as well as, dispersibility in a toilet bowl;
(3) does not cause skin irritation;
(4) reduces tackiness of the wipe, and provides unique tactile properties, such as skin glide and a "lotion-like feel"; and
(5) acts as a vehicle to deliver "moist cleansing" and other skin health benefits.

The wetting composition should not act as a solvent for the binder and generally does not contain solvents other than water, and particularly does not contain organic solvents, though a small quantity (<1%) of a fragrance solubilizer such as polysorbate 20 may be present, depending on the fragrance and the salt concentration of the wetting composition. Desirably, the wetting composition contains less than about 10 weight percent of organic solvents, such as propylene glycol or other glycols, polyhydroxy alcohols, and the like, based on the total weight of the wetting composition. More desirably, the wetting composition contains less than about 4 weight percent of organic solvents. Even more desirably, the wetting composition contains less than about 1 weight percent of organic solvents. The wetting composition can be substantially free of organic solvents.

One aspect of the present invention is a wetting composition, which contains an activating compound that maintains the strength of a water-dispersible binder until the activating compound is diluted with water, whereupon the strength of the water-dispersible binder begins to decay. The water-dispersible binder may be any of the ion-sensitive binder compositions of the present invention or any other ion-sensitive binder composition. The activating compound in the wetting composition can be a salt, such as sodium chloride, or any other compound, which provides in-use and storage strength to the water-dispersible binder composition, and can be diluted in water to permit dispersion of the substrate as the binder polymer triggers to a weaker state. Desirably, the wetting composition contains less than about 10 weight percent of an activating compound based on the total weight of the wetting composition. Specifically, the wetting composition may contain from about 0.3 weight percent to about 5 weight percent of an activating compound. Even more specifically, the wetting composition may contain from about 2 weight percent to about 4 weight percent of an activating compound.

The wetting composition of the present invention may further comprise a variety of additives compatible with the activating compound and the water-dispersible binder, such that the strength and dispersibility functions of the wipe are not jeopardized. Suitable additives in the wetting composition include, but are not limited to, the following additives: skin-care additives; odor control agents; detackifying agents to reduce the tackiness of the binder; particulates; antimicrobial agents; preservatives; wetting agents and cleaning agents such as detergents, surfactants, and some silicones; emollients; surface feel modifiers for improved tactile sensation (e.g., lubricity) on the skin; fragrance; fragrance solubilizers; opacifiers; fluorescent whitening agents; UV absorbers; pharmaceuticals; and pH control agents, such as malic acid or potassium hydroxide.

Skin-Care Additives

As used herein, the term "skin-care additives" represents additives, which provide one or more benefits to the user, such as a reduction in the probability of having diaper rash and/or other skin damage caused by fecal enzymes. These enzymes, particularly trypsin, chymotrypsin and elastase, are proteolytic enzymes produced in the gastrointestinal tract to digest food. In infants, for example, the feces tend to be watery and contain, among other materials, bacteria, and some amounts of undegraded digestive enzymes. These enzymes, if they remain in contact with the skin for any appreciable period of time, have been found to cause an irritation that is uncomfortable in itself and can predispose the skin to infection by microorganisms. As a countermeasure, skin-care additives include, but are not limited to, the enzyme inhibitors and sequestrants set forth hereafter. The wetting composition may contain less than about 5 weight percent of skin-care additives based on the total weight of the wetting composition. More specifically, the wetting composition may contain from about 0.01 weight percent to about 2 weight percent of skin-care additives. Even more specifically, the wetting composition may contain from about 0.01 weight percent to about 0.05 weight percent of skin-care additives.

A variety of skin-care additives may be added to the wetting composition and the pre-moistened wipes of the present invention or included therein. In one embodiment of the present invention, skin-care additives in the form of particles are added to serve as fecal enzyme inhibitors, offering potential benefits in the reduction of diaper rash and skin damage caused by fecal enzymes. U.S. Pat. No. 6,051,749, issued Apr. 18, 2000 to Schulz et al., the entirety of which is herein incorporated by reference, discloses organophilic clays in a woven or nonwoven web, said to be useful for inhibiting fecal enzymes. Such materials may be used in the present invention, including reaction products of a long chain organic quaternary ammonium compound with one or more of the following clays: montmorillonite, bentonite, beidellite, hectorite, saponite, and stevensite.

Other known enzyme inhibitors and sequestrants may be used as skin-care additives in the wetting composition of the present invention, including those that inhibit trypsin and other digestive or fecal enzymes, and inhibitors for urease. For example, enzyme inhibitors and anti-microbial agents may be used to prevent the formation of odors in body fluids. For example, urease inhibitors, which are also said to play a role in odor absorption, are disclosed by T. Trinh in World Patent Application No. 98/26808, "Absorbent Articles with Odor Control System," published Jun. 25, 1998, the entirety of which is herein incorporated by reference. Such inhibitors may be incorporated into the wetting composition and the pre-moistened wipes of the present invention and include transition metal ions and their soluble salts, such as silver, copper, zinc, ferric, and aluminum salts. The anion may also provide urease inhibition, such as borate, phytate, etc. Compounds of potential value include, but are not limited to, silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride.

Other salts that have been disclosed as having urease inhibition properties include ferric and aluminum salts, especially the nitrates, and bismuth salts. Other urease inhibitors are disclosed by Trinh, including hydroxamic acid and its derivatives; thiourea; hydroxylamine; salts of phytice acid; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosphoramidates without substitution on the nitrogen; boric acid and/or its salts, including especially, borax, and/or organic boron acid compounds; the compounds disclosed in European Patent Application 408,199; sodium, copper, manganese, and/or zinc dithiocarbamate; quinones; phenols; thiurams; substituted rhodanine acetic acids; alkylated benzoquinones; formarnidine disulphide; 1:3-diketones maleic anhydride; succinamide; phthalic anhydride; pehenic acid; N,N-dihalo-2-imidazolidinones; N-halo2-oxazolidinones; thio- and/or acylphosphoryltnamide and/or substituted derivatives thereof-, thiopyridine-N-oxides, thiopyridines, and thiopyrimidines; oxidized sulfur derivatives of diarninophosphinyl compounds; cyclotriphosphazatriene derivatives; orthodiaminophosphinyl derivatives of oximes; bromo-nitro compounds; S-aryl and/or alkyl diamidophosphorothiolates; diaminophosphinyl derivatives; mono- and/or polyphosphorodiamide; 5-substituted-benzoxathiol-2-ones; N(diaminophosphinyl)arylcarboxamides; alkoxy-1,2-benzothaizin compounds; etc.

Many other skin-care additives may be incorporated into the wetting composition and pre-moistened wipes of the present invention, including, but not limited to, sun blocking agents and UV absorbers, acne treatments, pharmaceuticals, baking soda (including encapsulated forms thereof), vitamins and their derivatives such as Vitamins A or E, botanicals such as witch hazel extract and aloe vera, allantoin, emollients, disinfectants, hydroxy acids for wrinkle control or anti-aging effects, sunscreens, tanning promoters, skin lighteners, deodorants and antiperspirants, ceramides for skin benefits and other uses, astringents, moisturizers, nail polish removers, insect repellants, antioxidants, antiseptics, anti-inflammatory agents and the like, provided that the additives are compatible with an ion-sensitive binder composition associated therewith, and especially the ion-sensitive binder compositions of the present invention (i.e., they do not cause a substantial loss of strength in the wet state of the pre-moistened wipes, prior to dilution in water, while permitting dispersibility in water).

Useful materials for skin care and other benefits are listed in *McCutcheon's* 1999, Vol. 2: Functional Materials, MC Publishing Company, Glen Rock, N.J. Many useful botanicals for skin care are provided by Active Organics, Lewisville, Tex.

Odor Control Additives

Suitable odor control additives for use in the wetting composition and pre-moistened wipes of the present invention include, but are not limited to, zinc salts; talc powder; encapsulated perfumes (including microcapsules, macrocapsules, and perfume encapsulated in liposomes, vessicles, or microemulsions); chelants, such as ethylenediamine tetra-acetic acid; zeolites; activated silica, activated carbon granules or fibers; activated silica particulates; polycarboxylic acids, such as citric acid; cyclodextrins and cyclodextrin derivatives; chitosan or chitin and derivatives thereof; oxidizing agents; antimicrobial agents, including silver-loaded zeolites (e.g., those of BF Technologies, located in Beverly, Mass., sold under the trademark HEALTHSHIELD™); triclosan; kieselguhr; and mixtures thereof. In addition to controlling odor from the body or body wastes, odor control strategies can also be employed to mask or control any odor of the treated substrate. Desirably, the wetting composition contains less than about 5 weight percent of odor control additives based on the total weight of the wetting composition. More desirably, the wetting composition contains from about 0.01 weight percent to about 2 weight percent of odor control additives. Even more desirably, the wetting composition contains from about 0.03 weight percent to about 1 weight percent of odor control additives.

In one embodiment of the present invention, the wetting composition and/or pre-moistened wipes comprise derivatized cyclodextrins, such as hydroxypropyl beta-cyclodextrin in solution, which remain on the skin after wiping and provide an odor-absorbing layer. In other embodiments, the odor source is removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the product.

Principles for the application of chitosan or chitin derivatives to nonwoven webs and cellulosic fibers are described by S. Lee et al. in "Antimicrobial and Blood Repellent Finishes for Cotton and Nonwoven Fabrics Based on Chitosan and Fluoropolymers," Textile Research Journal, 69(2); 104–112, February 1999.

Detackifying Agents

While elevated salt concentrations may reduce the tack of the ion-sensitive binder, other means of tack reduction are often desirable. Thus, detackifying agents may be used in the wetting composition to reduce the tackiness, if any, of the ion-sensitive binder. Suitable detackifiers include any substance known in the art to reduce tack between two adjacent fibrous sheets treated with an adhesive-like polymer or any substance capable of reducing the tacky feel of an adhesive-like polymer on the skin. Detackifiers may be applied as solid particles in dry form, as a suspension or as a slurry of particles. Deposition may be by spray, coating, electrostatic deposition, impingement, filtration (i.e., a pressure differential drives a particle-laden gas phase through the substrate, depositing particles by a filtration mechanism), and the like, and may be applied uniformly on one or more surfaces of the substrate or may be applied in a pattern (e.g., repeating or random patterns) over a portion of the surface or surfaces of the substrate. The detackifier may be present throughout the thickness of the substrate, but may be concentrated at one or both surfaces, and may be substantially only present on one or both surfaces of the substrate.

Specific detackifiers include, but are not limited to, powders, such as talc powder, calcium carbonate, mica; starches, such as corn starch; lycopodium powder; mineral fillers, such as titanium dioxide; silica powder; alumina; metal oxides in general; baking powder; kieselguhr; and the like. Polymers and other additives having low surface energy may also be used, including a wide variety of fluorinated polymers, silicone additives, polyolefins and thermoplastics, waxes, debonding agents known in the paper industry including compounds having alkyl side chains such as those having 16 or more carbons, and the like. Compounds used as release agents for molds and candle making may also be considered, as well as, dry lubricants and fluorinated release agents.

In one embodiment, the detackifier comprises polytetrafluoroethylene (PTFE), such as PTFE telomer (KRYTOX® DF) compound, used in the PTFE release agent dry lubricant MS-122DF, marketed by Miller-Stephenson (Danbury, Conn.) as a spray product. For example, PTFE particles may be applied by spray to one side of the substrate prior to winding of the pre-moistened wipes. In one embodiment, a detackifying agent is applied to only one surface of the substrate prior to winding into a roll.

The wetting composition desirably contains less than about 25 weight percent of detackifying agents based on the total weight of the wetting composition. More desirably, the wetting composition contains from about 0.01 weight percent to about 10 weight percent of detackifying agents, more specifically about 5% or less. Even more specifically, the wetting composition contains from about 0.05 weight percent to about 2 weight percent of detackifying agents.

In addition to acting as a detackifying agent, starch compounds may also improve the strength properties of the pre-moistened wipes. For example, it has been found that ungelled starch particles, such as hydrophilic tapioca starch, when present at a level of about 1% or higher by weight relative to the weight of the wetting composition, can permit the pre-moistened wipe to maintain the same strength at a lower salt concentration than is possible without the presence of starch. Thus, for example, a given strength can be achieved with 2% salt in the wetting composition in the presence of salt compared to a level of 4% salt being needed without starch. Starch may be applied by adding the starch to a suspension of laponite to improve the dispersion of the starch within the wetting composition.

Microparticulates

The wetting composition of the present invention may be further modified by the addition of solid particulates or microparticulates. Suitable particulates include, but are not limited to, mica, silica, alumina, calcium carbonate, kaolin, talc, and zeolites. The particulates may be treated with stearic acid or other additives to enhance the attraction or bridging of the particulates to the binder system, if desired. Also, two-component microparticulate systems, commonly used as retention aids in the papermaking industry, may also be used. Such two-component microparticulate systems generally comprise a colloidal particle phase, such as silica particles, and a water-soluble cationic polymer for bridging the particles to the fibers of the web to be formed. The presence of particulates in the wetting composition can serve one or more useful functions, such as (1) increasing the opacity of the pre-moistened wipes; (2) modifying the rheology or reducing the tackiness of the pre-moistened wipe; (3) improving the tactile properties of the wipe; or (4) delivering desired agents to the skin via a particulate carrier, such as a porous carrier or a microcapsule. Desirably, the wetting composition contains less than about 25 weight percent of particulate based on the total weight of the wetting composition. More specifically, the wetting composition may contain from about 0.05 weight percent to about 10 weight percent of microparticulate. Even more specifically, the wetting composition may contain from about 0.1 weight percent to about 5 weight percent of microparticulate.

Microcapsules and Other Delivery Vehicles

Microcapsules and other delivery vehicles may also be used in the wetting composition of the present invention to provide skin-care agents; medications; comfort promoting agents, such as eucalyptus; perfumes; skin care agents; odor control additives; vitamins; powders; and other additives to the skin of the user. Specifically, the wetting composition may contain up to about 25 weight percent of microcapsules or other delivery vehicles based on the total weight of the wetting composition. More specifically, the wetting composition may contain from about 0.05 weight percent to about 10 weight percent of microcapsules or other delivery vehicles. Even more specifically, the wetting composition may contain from about 0.2 weight percent to about 5.0 weight percent of microcapsules or other delivery vehicles.

Microcapsules and other delivery vehicles are well known in the art. For example, POLY-PORE® E200 (Chemdal Corp., Arlington Heights, Ill.), is a delivery agent comprising soft, hollow spheres that can contain an additive at over 10 times the weight of the delivery vehicle. Known additives reported to have been used with POLY-PORE® E200 include, but are not limited to, benzoyl peroxide, salicylic acid, retinol, retinyl palmitate, octyl methoxycinnamate, tocopherol, silicone compounds (DC 435), and mineral oil. Another useful delivery vehicle is a sponge-like material marketed as POLY-PORE® L200, which is reported to have been used with silicone (DC 435) and mineral oil. Other known delivery systems include cyclodextrins and their derivatives, liposomes, polymeric sponges, and spray-dried starch.

Additives present in microcapsules are isolated from the environment and the other agents in the wetting composition until the wipe is applied to the skin, whereupon the microcapsules break and deliver their load to the skin or other surfaces.

Preservatives and Anti-Microbial Agents

The wetting composition of the present invention may also contain preservatives and/or anti-microbial agents. Several preservatives and/or anti-microbial agents, such as Mackstat H 66 (available from McIntyre Group, Chicago, Ill.), have been found to give excellent results in preventing bacteria and mold growth. Other suitable preservatives and anti-microbial agents include, but are not limited to DMDM hydantoin (e.g., Glydant Plus™, Lonza, Inc., Fair Lawn, N.J.), iodopropynyl butylcarbamate, Kathon (Rohm and Hass, Philadelphia, Pa.), methylparaben, propylparaben, 2-bromo-2-nitropropane-1,3-diol, benzoic acid, and the like. Desirably, the wetting composition contains less than about 2 weight percent on an active basis of preservatives and/or anti-microbial agents based on the total weight of the wetting composition. More desirably, the wetting composition contains from about 0.01 weight percent to about 1 weight percent of preservatives and/or anti-microbial agents. Even more desirably, the wetting composition contains from about 0.01 weight percent to about 0.5 weight percent of preservatives and/or anti-microbial agents.

Wetting Agents and Cleaning Agents

A variety of wetting agents and/or cleaning agents may be used in the wetting composition of the present invention. Suitable wetting agents and/or cleaning agents include, but are not limited to, detergents and nonionic, amphoteric, and anionic surfactants, especially amino acid-based surfactants. Amino acid-based surfactant systems, such as those derived from amino acids L-glutamic acid and other natural fatty acids, offer pH compatibility to human skin and good cleansing power, while being relatively safe and providing improved tactile and moisturization properties compared to other anionic surfactants. One function of the surfactant is to improve wetting of the dry substrate with the wetting composition. Another function of the surfactant can be to disperse bathroom soils when the pre-moistened wipe contacts a soiled area and to enhance their absorption into the substrate. The surfactant can further assist in make-up removal, general personal cleansing, hard surface cleansing, odor control, and the like.

One commercial example of an amino-acid based surfactant is acylglutamate, marketed under the Amisoft name by Ajinomoto Corp., Tokyo, Japan. Desirably, the wetting composition contains less than about 3 weight percent of wetting agents and/or cleaning agents based on the total weight of the wetting composition. More desirably, the wetting composition contains from about 0.01 weight percent to about 2 weight percent of wetting agents and/or cleaning agents. Even more desirably, the wetting composition contains from about 0.1 weight percent to about 0.5 weight percent of wetting agents and/or cleaning agents.

Although amino-acid based surfactant are particularly useful in the wetting compositions of the present invention, a wide variety of surfactants may be used in the present invention. Suitable non-ionic surfactants include, but are not limited to, the condensation products of ethylene oxide with a hydrophobic (oleophilic) polyoxyalkylene base formed by the condensation of propylene oxide with propylene glycol. The hydrophobic portion of these compounds desirably has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include commercially-available Pluronic surfactants (BASF Wyandotte Corp.), especially those in which the polyoxypropylene ether has a molecular weight of about 1500–3000 and the polyoxyethylene content is about 35–55% of the molecule by weight, i.e. Pluronic L-62.

Other useful nonionic surfactants include, but are not limited to, the condensation products of $C_8$–$C_{22}$ alkyl alcohols with 2–50 moles of ethylene oxide per mole of alcohol. Examples of compounds of this type include the condensation products of $C_{11}$–$C_{15}$ secondary alkyl alcohols with 3–50 moles of ethylene oxide per mole of alcohol, which are commercially-available as the Poly-Tergent SLF series from Olin Chemicals or the TERGITOL® series from Union Carbide, i.e. TERGITOL® 25-L-7, which is formed by condensing about 7 moles of ethylene oxide with a $C_{12}$–$C_{15}$ alkanol.

Other nonionic surfactants, which may be employed in the wetting composition of the present invention, include the ethylene oxide esters of $C_6$–$C_{12}$ alkyl phenols such as (nonylphenoxy)polyoxyethylene ether. Particularly useful are the esters prepared by condensing about 8–12 moles of ethylene oxide with nonylphenol, i.e. the IGEPAL® CO series (GAF Corp.).

Further non-ionic surface active agents include, but are not limited to, alkyl polyglycosides (APG), derived as a condensation product of dextrose (D-glucose) and a straight or branched chain alcohol. The glycoside portion of the surfactant provides a hydrophile having high hydroxyl density, which enhances water solubility. Additionally, the inherent stability of the acetal linkage of the glycoside provides chemical stability in alkaline systems. Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is available from Horizon Chemical under the trade names of APG-300, APG-350, APG-500, and APG-500.

Silicones are another class of wetting agents available in pure form, or as microemulsions, macroemulsions, and the like. One exemplary non-ionic surfactant group is the silicone-glycol copolymers. These surfactants are prepared by adding poly(lower)alkylenoxy chains to the free hydroxyl groups of dimethylpolysiloxanols and are available from the Dow Corning Corp as Dow Corning 190 and 193 surfactants (CTFA name: dimethicone copolyol). These surfactants function, with or without any volatile silicones used as solvents, to control foaming produced by the other surfactants, and also impart a shine to metallic, ceramic, and glass surfaces.

Anionic surfactants may also be used in the wetting compositions of the present invention. Anionic surfactants are useful due to their high detergency include anionic detergent salts having alkyl substituents of 8 to 22 carbon atoms such as the water-soluble higher fatty acid alkali metal soaps, e.g., sodium myristate and sodium palmitate. A preferred class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group, with examples available as the Bio-Soft series, i.e. Bio-Soft D-40 (Stepan Chemical Co.).

Other useful classes of anionic surfactants include, but are not limited to, the alkali metal salts of alkyl naphthalene sulfonic acids (methyl naphthalene sodium sulfonate, Petro AA, Petrochemical Corporation); sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$–$C_{16}$-alphaolefin sulfonates such as the Bio-Terge series (Stepan Chemical Co.); alkali metal salts of sulfated ethyleneoxy fatty alcohols (the sodium or ammonium sulfates of the condensation products of about 3 moles of ethylene oxide with a $C_{12}$–$C_{15}$ n-alkanol, i.e., the Neodol ethoxysulfates, Shell Chemical Co.); alkali metal salts of higher fatty esters of low molecular weight alkylol sulfonic acids, e.g. fatty acid esters of the sodium salt of isothionic acid, the fatty ethanolamide sulfates; the fatty acid amides of amino alkyl sulfonic acids, e.g. lauric acid amide of taurine; as well as numerous other anionic organic surface active agents such as sodium xylene sulfonate, sodium naphthalene sulfonate, sodium toulene sulfonate and mixtures thereof.

A further useful class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surface active agents can be employed in the form of their alkali metal salts, ammonium or alkaline earth metal salts.

Macroemulsions and Microemulsion of Silicone Particles

The wetting composition may further comprise an aqueous microemulsion of silicone particles. For example, U.S. Pat. No. 6,037,407, "Process for the Preparation of Aqueous Emulsions of Silicone Oils and/or Gums and/or Resins" issued Mar. 14, 2000, discloses organopolysiloxanes in an aqueous microemulsion. Desirably, the wetting composition contains less than about 5 weight percent of a microemulsion of silicone particles based on the total weight of the wetting composition. More desirably, the wetting composition contains from about 0.02 weight percent to about 3 weight percent of a microemulsion of silicone particles. Even more desirably, the wetting composition contains from about 0.02 weight percent to about 0.5 weight percent of a microemulsion of silicone particles.

Silicone emulsions in general may be applied to the pre-moistened wipe by any known coating method. For example, the pre-moistened wipe may be moistened with an aqueous composition comprising a water-dispersible or water-miscible, silicone-based component that is compatible with the activating compound in the wetting composition. Further, the wipe can comprise a nonwon web of fibers having a water-dispersible binder, wherein the web is moistened with a lotion comprising a silicone-based sulfosuccinate. The silicone-based sulfosuccinate provides gentle and effective cleansing without a high level of surfactant. Additionally, the silicone-based sulfosuccinate provides a solubilization function, which prevents precipitation of oil-soluble components, such as fragrance components, vitamin extracts, plant extracts, and essential oils.

In one embodiment of the present invention, the wetting composition comprises a silicone copolyol sulfosuccinate, such as disodium dimethicone copolyol sulfosuccinate and diammonium dimethicone copolyolsulfosuccinate. Desirably, the wetting composition comprises less than about 2 percent by weight of the silicone-based sulfosuccinate, and more desirably from about 0.05 percent to about 0.30 percent by weight of the silicone-based sulfosuccinate.

In another example of a product comprising a silicone emulsions, Dow Corning 9506 powder may also be present in the wetting composition. Dow Corning 9506 powder is believed to comprise a dimethicone/vinyldimethicone crosspolymer and is a spherical powder, which is said to be useful in controlling skin oils (see "New Chemical Perspectives," *Soap and Cosmetics,* Vol. 76, No. 3, March 2000, p. 12). Thus, a water-dispersible wipe, which delivers a powder effective in controlling skin oil, is also within the scope of the present invention. Principles for preparing silicone emulsions are disclosed in WO 97/10100, published Mar. 20, 1997.

Emollients

The wetting composition of the present invention may also contain one or more emollients. Suitable emollients include, but are not limited to, PEG 75 lanolin, methyl gluceth 20 benzoate, $C_{12}$–$C_{15}$ alkyl benzoate, ethoxylated cetyl stearyl alcohol, products marketed as Lambent wax WS-L, Lambent WD-F, Cetiol HE (Henkel Corp.), Glucam P20 (Amerchol), Polyox WSR N-10 (Union Carbide), Polyox WSR N-3000 (Union Carbide), Luviquat (BASF), Finsolv SLB 101 (Finetex Corp.), mink oil, allantoin, stearyl alcohol, Estol 1517 (Unichema), and Finsolv SLB 201 (Finetex Corp.).

An emollient can also be applied to a surface of the article prior to or after wetting with the wetting composition. Such an emollient may be insoluble in the wetting composition and can be immobile except when exposed to a force. For example, a petrolatum-based emollient can be applied to one surface in a pattern, after which the other surface is wetted to saturate the wipe. Such a product could provide a cleaning surface and an opposing skin treatment surface.

The emollient composition in such products and other products of the present invention can comprise a plastic or fluid emollient such as one or more liquid hydrocarbons (e.g., petrolatum), mineral oil and the like, vegetable and animal fats (e.g., lanolin, phospholipids and their derivatives) and/or a silicone materials such as one or more alkyl substituted polysiloxane polymers, including the polysiloxane emollients disclosed in U.S. Pat. No. 5,891,126, issued Apr. 6, 1999 to Osborn, III et al. Optionally, a hydrophilic surfactant may be combined with a plastic emollient to improve wettability of the coated surface. In some embodiments of the present invention, it is contemplated that liquid hydrocarbon emollients and/or alkyl substituted polysiloxane polymers may be blended or combined with one or more fatty acid ester emollients derived from fatty acids or fatty alcohols.

In an embodiment of the present invention, the emollient material is in the form of an emollient blend. Desirably, the emollient blend comprises a combination of one or more liquid hydrocarbons (e.g., petrolatum), mineral oil and the like, vegetable and animal fats (e.g., lanolin, phospholipids and their derivatives), with a silicone material such as one or more alkyl substituted polysiloxane polymers. More desirably, the emollient blend comprises a combination of liquid hydrocarbons (e.g., petrolatum) with dimethicone or with dimethicone and other alkyl substituted polysiloxane polymers. In some embodiments of the present invention, it is contemplated that blends of liquid hydrocarbon emollients and/or alkyl substituted polysiloxane polymers may be blended with one or more fatty acid ester emollients derived from fatty acids or fatty alcohols. PEG-7 glyceryl cocoate, available as Standamul HE (Henkel Corp., Hoboken, N.J.), can also be considered.

Water-soluble, self-emulsifying emollient oils, which are useful in the present wetting compositions, include the polyoxyalkoxylated lanolins and the polyoxyalkoxylated fatty alcohols, as disclosed in U.S. Pat. No. 4,690,821, issued Sep. 1, 1987 to Smith et al. The polyoxyalkoxy chains desirably will comprise mixed propylenoxy and ethyleneoxy units. The lanolin derivatives will typically comprise about 20–70 such lower-alkoxy units while the $C_{12}$–$C_{20}$-fatty alcohols will be derivatized with about 8–15 lower-alkyl units. One such useful lanolin derivative is Lanexol AWS (PPG-12-PEG-50, Croda, Inc., New York, N.Y.). A useful poly(15–20)$C_2$–$C_3$-alkoxylate is PPG-5-Ceteth-20, known as Procetyl AWS (Croda, Inc.).

According to one embodiment of the present invention, the emollient material reduces undesirable tactile attributes, if any, of the wetting composition. For example, emollient materials, including dimethicone, can reduce the level of tackiness that may be caused by the ion-sensitive binder or other components in the wetting composition, thus serving as a detackifier.

Desirably, the wetting composition contains less than about 25 weight percent of emollients based on the total weight of the wetting composition. More specifically, the wetting composition may comprise less than about 5 weight percent emollient, and most specifically less than about 2% emollient. More desirably, the wetting composition may contain from about 0.01 weight percent to about 8 weight percent of emollients. Even more desirably, the wetting composition may contain from about 0.2 weight percent to about 2 weight percent of emollients.

In one embodiment, the wetting composition and/or pre-moistened wipes of the present invention comprise an oil-in-water emulsion comprising an oil phase containing at least one emollient oil and at least one emollient wax stabilizer dispersed in an aqueous phase comprising at least one polyhydric alcohol emollient and at least one organic water-soluble detergent, as disclosed in U.S. Pat. No. 4,559,157, issued Dec. 17, 1985 to Smith et al., the entirety of which is herein incorporated by reference.

Surface Feel Modifiers

Surface feel modifiers are used to improve the tactile sensation (e.g., lubricity) of the skin during use of the product. Suitable surface feel modifiers include, but are not limited to, commercial debonders; and softeners, such as the softeners used in the art of tissue making including quaternary ammonium compounds with fatty acid side groups, silicones, waxes, and the like. Exemplary quaternary ammonium compounds with utility as softeners are disclosed in U.S. Pat. No. 3,554,862, issued to Hervey et al. on Jan. 12, 1971; U.S. Pat. No. 4,144,122, issued to Emanuelsson et al., Mar. 13, 1979, U.S. Pat. No. 5,573,637, issued to Ampulski et al. Nov. 12, 1996; and U.S. Pat. No. 4,476,323, issued to Hellsten et al., Oct. 9, 1984, the entirety of all of which is herein incorporated by reference. Desirably, the wetting composition contains less than about 2 weight percent of surface feel modifiers based on the total weight of the wetting composition. More desirably, the wetting composition contains from about 0.01 weight percent to about 1 weight percent of surface feel modifiers. Even more desirably, the wetting composition contains from about 0.01 weight percent to about 0.05 weight percent of surface feel modifiers.

Fragrances

A variety of fragrances may be used in the wetting composition of the present invention. Desirably, the wetting composition contains less than about 2 weight percent of fragrances based on the total weight of the wetting composition. More desirably, the wetting composition contains from about 0.01 weight percent to about 1 weight percent of fragrances. Even more desirably, the wetting composition contains from about 0.01 weight percent to about 0.05 weight percent of fragrances.

Fragrance Solubilizers

Further, a variety of fragrance solubilizers may be used in the wetting composition of the present invention. Suitable fragrance solubilizers include, but are not limited to, polysorbate 20, propylene glycol, ethanol, isopropanol, diethylene glycol monoethyl ether, dipropylene glycol, diethyl phthalate, triethyl citrate, Ameroxol OE-2 (Amerchol Corp.), Brij 78 and Brij 98 (ICI Surfactants), Arlasolve 200 (ICI Surfactants), Calfax 16L-35 (Pilot Chemical Co.), Capmul POE-S (Abitec Corp.), Finsolv SUBSTANTIAL (Finetex), and the like. Desirably, the wetting composition contains less than about 2 weight percent of fragrance solubilizers based on the total weight of the wetting composition. More desirably, the wetting composition contains from about 0.01 weight percent to about 1 weight percent of fragrance solubilizers. Even more desirably, the wetting composition contains from about 0.01 weight percent to about 0.05 weight percent of fragrance solubilizers.

Opacifiers

Suitable opacifiers include, but are not limited to, titanium dioxide or other minerals or pigments, and synthetic opacifiers such as REACTOPAQUE® particles (available from Sequa Chemicals, Inc., Chester, S.C.). Desirably, the wetting composition contains less than about 2 weight percent of opacifiers based on the total weight of the wetting composition. More desirably, the wetting composition contains from about 0.01 weight percent to about 1 weight percent of opacifiers. Even more desirably, the wetting composition contains from about 0.01 weight percent to about 0.05 weight percent of opacifiers.

pH Control Agents

Suitable pH control agents for use in the wetting composition of the present invention include, but are not limited to, malic acid, citric acid, hydrochloric acid, acetic acid, sodium hydroxide, potassium hydroxide, and the like. An appropriate pH range minimizes the amount of skin irritation resulting from the wetting composition on the skin. Desirably, the pH range of the wetting composition is from about 3.5 to about 6.5. More desirably, the pH range of the wetting composition is from about 4 to about 6. Desirably, the wetting composition contains less than about 2 weight percent of a pH adjuster based on the total weight of the wetting composition. More desirably, the wetting composition contains from about 0.01 weight percent to about 1 weight percent of a pH adjuster. Even more desirably, the wetting composition contains from about 0.01 weight percent to about 0.05 weight percent of a pH adjuster.

Although a variety of wetting compositions, formed from one or more of the above-described components, may be used with the wet wipes of the present invention, in one embodiment, the wetting composition contains the following components, given in weight percent of the wetting composition, as shown in Table 2 below:

TABLE 2

Wetting Composition Components

| Wetting Composition Component: | Weight Percent: |
|---|---|
| Deionized Water | about 86 to about 98 |
| Activating compound | about 1 to about 6 |
| Preservative | Up to about 2 |
| Surfactant | Up to about 2 |
| Silicone Emulsion | Up to about 1 |
| Emollient | Up to about 1 |
| Fragrance | Up to about 0.3 |
| Fragrance solubilizer | Up to about 0.5 |
| pH adjuster | Up to about 0.2 |

In another embodiment of the present invention, the wetting composition comprises the following components, given in weight percent of the wetting composition, as shown in Table 3 below:

TABLE 3

Wetting Composition Components

| Class of Wetting Composition Component: | Specific Wetting Composition Component: | Component Name: | Weight Percent: |
|---|---|---|---|
| Vehicle | Deionized Water | | about 86 to about 98 |
| Activating compound | Sodium Chloride (Millport Ent., Milwaukee, WI) | | about 1 to about 6 |
| Preservative | Glycerin, IPBC and DMDM Hydantoin | Mackstat H-66 (McIntyre Group, Chicago, IL) | Up to about 2 |
| Surfactant | Acyl Glutamate | CS22 (Ajinomoto, Tokyo, Japan) | Up to about 2 |
| Silicone Emulsion (Detackifier/Skin Feel agent) | Dimethiconol and TEA Dodecylbenezene Sulfonate | DC1785 (Dow Corning, Midland, MI) | Up to about 1 |
| Emollient | PEG-75 Lanolin | Solulan L- 575 (Amerchol, Middlesex, NJ) | Up to about 1 |
| Fragrance | Fragrance | Dragoco 0/708768 (Dragoco, Roseville, MN) | Up to about 0.3 |
| Fragrance solubilizer | Polysorbate 20 | Glennsurf L20 (Glenn Corp., St. Paul, MN) | Up to about 0.5 |
| pH adjuster | Malic Acid to pH 5 (Haarman & Reimer, Tetrboro, NJ) | | Up to about 0.2 |

In another embodiment of the present invention, the wetting composition comprises the following components, given in weight percent of the wetting composition, as shown in Table 4 below:

TABLE 4

An Exemplary Wetting Composition

| Class of Wetting composition Component: | Specific Wetting composition Component: | Component Name: | Weight Percent: |
|---|---|---|---|
| Vehicle | Deionized Water | | about 93 |
| Activating compound | Sodium Chloride | | about 4 |
| Preservative | Glycerin, IPBC and DMDM Hydantoin | Mackstat H-66 | about 1 |
| Surfactant | Acyl Glutamate | CS22/ECS 22P DC 1784/ DC1785 | about 1 |
| Silicone Emulsion | Dimethiconol and TEA Dodecylbenezene Sulfonate | | about 0.5 |
| Emollient | PEG-75 Lanolin | Solulan L- 575 | about 0.25 |
| Fragrance | Fragrance | Dragoco Fragrance 0/708768 | about 0.05 |
| Fragrance solubilizer | Polysorbate 20 | Glennsurf L20 | about 0.25 |
| pH adjuster | Malic Acid to pH 5 | | about 0.07 |

It should be noted that the above-described wetting compositions of the present invention may be used with any one of the above-described ion-sensitive binder compositions of the present invention. Further, the above-described wetting compositions of the present invention may be used with any other binder composition, including conventional binder compositions, or with any known fibrous or absorbent substrate, whether dispersible or not.

Strength Properties

Unless otherwise specified, tensile testing is performed according to the following protocol. Testing of dry product should be conducted under Tappi conditions (50% relative humidity, 73° F.) with a procedure similar to ASTM-1117-80, section 7. Tensile tests are performed with a constant crosshead speed tensile tester such as the Thwing Albert 1256-100 tensile tester with an RSA-2 10-kg load cell. Specimens are cut to 3-inch widths and 6 inch lengths, and mounted between jaws with a 4-inch gauge length. The crosshead speed is 12 inches per minute. Peak load (for tensile strength) and elongation at peak load (for stretch) are measured. For cross direction (CD) tensile tests, the sample is cut in the cross direction. For machine direction (MD) tensile tests, the sample is cut in the cross direction.

Tensile tests in the dry state are reported for webs taken prior to application of the wetting composition. The machine direction dry tensile strength is abbreviated as "MDDT," and the cross direction dry tensile strength as "CDDT." The results can be reported as kg/3-in or converted to units of g/in or g/2.54 cm.

Based on the dry weight of the specimen cut to the appropriate size, an excess amount of wetting solution (4% saline solution with no other additives, unless otherwise specified) is applied to reach a solution add-on of 250–400%. The wetted specimens are then immediately passed through an Atlas Lab Wringer (Atlas Electric Devices Company, Chicago, Ill. No. 10404 LW-1, no load) to uniformly distribute the solution in the sample and gently remove the excess solution to achieve a final solution add-on of 200%. Several iterations or passes may be needed to reach the add-on target depending on the sample. The completed, pre-moistened samples are then bagged in plastic to prevent dry-out before testing.

Cross direction wet tensile tests (CDWT) or machine direction wet tensile strength (MDWT) are performed as described above using the pre-moistened sample as is, after the sample has equilibrated by sitting overnight in a sealed plastic bag.

For tests related to strength loss in a premoistened web occurring after exposure to a new solution, a container having dimensions of 200 mm by 120 mm and deep enough to hold 1000 ml is filled with 700 ml of the selected soak solution. No more than 108 square inches of sample are soaked in the 700 ml of soaking solution, depending on specimen size. The premoistened specimens, that have equilibrated overnight, are immersed in the soak solution and then allowed to soak undisturbed for a specified time period (typically 1 hour). At the completion of the soak period, samples are carefully retrieved from the soak solution, allowed to drain, and then tested immediately as described above (i.e., the sample is immediately mounted in the tensile tester and tested, without being passed through the wringer). In cases with highly dispersible materials, the samples often cannot be retrieved from the soaking solution without falling apart. The soaked tensile values for such samples are recorded as zero for the corresponding solution.

For the deionized soaked cross-direction wet tensile test, S-CDWT, the sample is immersed in deionized water for 1 hour and then tested. For the hard-water soaked cross-direction wet tensile test, S-CDWT-M (M indicating divalent metal ions), the sample is immersed in water containing 200 ppm of $Ca^{++}/Mg^{++}$ in a 2:1 ratio prepared from calcium chloride and magnesium chloride, soaked for one hour and then tested. For the medium hard water soaked cross-direction wet tensile test, MS-CDWT-M, the sample is immersed in water containing 50 ppm of $Ca^{++}/Mg^{++}$ in a 2:1 ratio, soaked for one hour and then tested. Testing done with other time increments or soaking solutions should be so indicated to prevent confusion with the S-CDWT or S-CDWT-M tests.

In one embodiment of the present invention, wet wipes are produced using the above-described wetting composition in Table 3 and an air-laid fibrous material comprising about 80 weight percent of bleached kraft fibers and 20 weight percent of any one of the above-described ion-sensitive binder compositions of the present invention, wherein the weight percentages are based on the total weight of the dry nonwoven fabric. In a further embodiment of the present invention, wet wipes are produced using the above-described wetting composition in Table 3 and an air-laid fibrous material comprising 90 weight percent of softwood fibers and 10 weight percent of an ion-sensitive binder compositions comprising acrylic acid terpolymers or a copolymer substantially free of acrylic acid monomers, wherein the weight percentages are based on the total weight of the dry nonwoven fabric. The amount of wetting composition added to the nonwoven fabric, relative to the weight of the dry nonwoven fabric in these embodiments, is desirably about 180 percent to about 240 weight percent.

Desirably, the wet wipes of the present invention possess an in-use wet tensile strength (CDWT) of at least 100 g/in, and a tensile strength of less than about 30 g/in after being soaked in water having a concentration of $Ca^{2+}$ and/or $Mg^{2+}$ ions of about 50 ppm for about one hour (MS-CDWT-M). More desirably, the wet wipes possess an in-use wet tensile strength of at least 300 g/in (CDWT), and a tensile strength of less than about 30 g/in after being soaked in water having a concentration of $Ca^{2+}$ and/or $Mg^{2+}$ ions of about 50 ppm for about one hour (MS-CDWT-M). In a further embodiment, the wet wipes desirably possess an in-use wet tensile strength of at least 200 g/in (CDWT), and a tensile strength of less than about 20 g/in after being soaked in water having a concentration of $Ca^{2+}$ and/or $Mg^{2+}$ ions of about 200 ppm for about one hour (S-CDWT-M). Even more desirably, the wet wipes possess an in-use wet tensile strength of at least 300 g/in, and a tensile strength of less than about 20 g/in after being soaked in water having a concentration of $Ca^{2+}$ and/or $Mg^{2+}$ ions of about 200 ppm for about one hour (S-CDWT-M).

Desirably, the wet wipes treated with the binder material of the present invention including the acrylic acid terpolymer possess an in-use wet tensile strength of at least 100 g/in for a 1 inch width sample in the cross machine direction when soaked with 10% to 400% by weight wet wipes solution containing more than 0.3% by weight monovalent ion (NaCl) concentration and a tensile strength of less than about 30 g/in after being soaked in deionized water for about one hour. More desirably, the wet wipes treated with the binder material of the present invention including the acrylic acid terpolymer possess an in-use tensile strength of at least 200 g/in for a 1 inch width sample in the cross machine direction when soaked with 10% to 400% by weight wet wipes solution containing more than 0.3% by weight monovalent ion (NaCl) concentration and a tensile strength of less than about 30 g/in after being soaked in deionized water for about one hour.

In a further embodiment, the wet wipes treated with the binder material of the present invention including the sulfonate anion modified acrylic acid terpolymer desirably possess an in-use tensile strength of at least 200 g/in for a 1 inch width sample in the cross machine direction when soaked with 10% to 400% by weight wet wipes solution containing more than 1% by weight monovalent ion (NaCl) concentration and a tensile strength of less than about 30 g/in after being soaked in water having a concentration of $Ca^{2+}$ and/or $Mg^{2+}$ ions of about 50 ppm for about one hour. Even more desirably, the wet wipes treated with the binder material of the present invention including the sulfonate anion modified acrylic acid terpolymer possess an in-use tensile strength of at least 200 g/in for a 1 inch width sample in the cross machine direction when soaked with 10% to 400% by weight wet wipes solution containing more than 1% by weight monovalent ion (NaCl) concentration and a tensile strength of less than about 30 g/in after being soaked in water having a concentration of $Ca^{2+}$ and/or $Mg^{2+}$ ions of about 200 ppm for about one hour.

Products with high basis weights or wet strengths than flushable wet wipes may have relatively higher wet tensile strength. For example, products such as pre-moistened towels or hard-surface cleaning wipes may have basis weights above 70 gsm, such as from 80 gsm to 150 gsm. Such products can have CDWT values of 500 g/in or greater, with S-CDWT values of about 150 g/in or less, more specifically about 100 g/in or less, and most specifically about 50 g/in or less, with similar ranges possible for S-CDWT-M.

Dispersibility

Prior efforts to measure dispersibility of webs, whether dry or premoistened, have commonly relied on systems in which the web was exposed to shear while in water, such as measuring the time for a web to break up while being agitated by a mechanical mixer. The constant exposure to shear offers an unrealistic and overly optimistic test for products designed to be flushed in a toilet, where the level of shear is weak and extremely brief. Once the product has passed through the neck of the toilet and entered a septic tank, shear rates may be negligible. Further, the product may not be fully wetted with water from the toilet bowl when it is flushed, or rather, there may not have been adequate time for the wetting composition of the product to have been replaced with the water of the toilet bowl when the momentary shear of flushing is applied. Thus, previous measurements of dispersibility could suggest that a product is dispersible when, in fact, it may be poorly suited for septic system.

For a realistic appraisal of dispersibility, it is believed that a relatively static measure is needed to better simulate the low shear that real products will experience once they have become fully wetted with water from the toilet. Thus, a test method for dispersibility has been developed which does not rely on shear and which provides an improved means of assessing suitability of a product for a septic system. In this method, the tensile strength of a product is measured in its original, wetted form (the CDWT measurement described above) and after the product has been soaked in a second solution for one hour (either the S-CDWT or S-CDWT-M test). The second solution can be either deionized water for determination of the "Deionized Dispersibility" value or hard water (according to the S-CDWT-M test) for determination of the "Hard Water Dispersibility" value. In either case, the Dispersibility is defined as (1 minus the ratio of the cross-direction wet tensile strength in the second solution divided by the original cross-direction wet tensile strength) * 100%. Thus, if a pre-moistened wipe loses 75% of its CD wet tensile strength after soaking in hard water for one hour, the Hard Water Dispersibility is (1−0.25)*100%=75%. The articles of the present invention can have a Deionized Dispersibility of 80% or greater, more specifically 90% or greater, specifically still 95% or greater, and can have a Deionized Dispersibility of about 100%. The articles of the present invention can have a Hard Water Dispersibility of 70% or greater, more specifically 80% or greater, specifically still about 90% or greater, and can have a Deionized Dispersibility of about 100%.

Method of Making Wet Wipes

The pre-moistened wipes of the present invention can be made in several ways. In one embodiment, the ion-sensitive polymer composition is applied to a fibrous substrate as part of an aqueous solution or suspension, wherein subsequent drying is needed to remove the water and promote binding of the fibers. In particular, during drying, the binder migrates to the crossover points of the fibers and becomes activated as a binder in those regions, thus providing acceptable strength to the substrate. For example, the following steps can be applied:

1. Providing an absorbent substrate that is not highly bonded (e.g., an unbonded airlaid, a tissue web, a carded web, fluff pulp, etc.).
2. Applying an ion-sensitive polymer composition to the substrate, typically in the form of a liquid, suspension, or foam.
3. Applying a co-binder polymer to the substrate.
4. Drying the substrate to promote bonding of the substrate. The substrate may be dried such that the peak substrate temperature does not exceed 160° C., or 140° C., or 120° C., 110° C., or 100° C. In one embodiment, the substrate temperature does not exceed 80° C. or 60° C.
5. Applying a wetting composition to the substrate.
6. Placing the wetted substrate in roll form or in a stack and packaging the product.

Application of the co-binder polymer can be done simultaneously with application of the binder composition by previously mixing the two, or the co-binder polymer can be added before or after the binder is applied. The other steps are desirably conducted in the order shown above.

Application of the ion-sensitive polymer composition to the substrate can be by means of spray; by foam application; by immersion in a bath; by curtain coating; by coating and metering with a wire-wound rod; by passage of the substrate through a flooded nip; by contact with a pre-metered wetted roll coated with the binder solution; by pressing the substrate against a deformable carrier containing the ion-sensitive polymer composition such as a sponge or felt to effect transfer into the substrate; by printing such as gravure, inkjet, or flexographic printing; and any other means known in the art.

In the use of foams to apply a binder or co-binder polymer, the mixture is frothed, typically with a foaming agent, and spread uniformly on the substrate, after which vacuum is applied to pull the froth through the substrate. Any known foam application method can be used, including that of U.S. Pat. No. 4,018,647, "Process for the Impregnation of a Wet Fiber Web with a Heat Sensitized Foamed Latex Binder," issued Apr. 19, 1977 to Wietsma, the entirety of which is herein incorporated by reference. Wietsma discloses a method wherein a foamed latex is heat-sensitized by the addition of a heat-sensitizer such as functional siloxane compounds including siloxane oxyalkylene block copolymers and organopolysiloxanes. Specific examples of applicable heat-sensitizers and their use thereof for the heat sensitization of latices are described in the U.S. Pat. Nos. 3,255,140; 3,255,141; 3,483,240 and 3,484,394, all of which are incorporated herein by reference. The use of a heat-sensitizer is said to result in a product having a very soft and textile-like hand compared to prior methods of applying foamed latex binders.

The amount of heat-sensitizer to be added is dependent on, inter alia, the type of latex used, the desired coagulation temperature, the machine speed and the temperatures in the drying section of the machine, and will generally be in the range of about 0.05 to about 3% by weight, calculated as dry matter on the dry weight of the latex; but also larger or smaller amounts may be used. The heat sensitizer can be added in such an amount that the latex will coagulate far below the boiling point of water, for instance at a temperature in the range of 35° C. to 95° C., or from about 35° C. to 65° C.

Without wishing to be bound by theory, it is believed that a drying step after application of the binder solution and before application of the wetting composition enhances bonding of a fibrous substrate by driving the binder to fiber crossover points as moisture is driven off, thus promoting efficient use of the binder. However, in an alternative method, the drying step listed above is skipped, and the ion-sensitive polymer composition is applied to the substrate followed by application of the wetting composition without significant intermediate drying. In one version of this method, the ion-sensitive polymer composition selectively adheres to the fibers, permitting excess water to be removed in an optional pressing step without a significant loss of the binder from the substrate. In another version, no significant water removal occurs prior to application of the wetting composition. In yet another alternative method, the ion-sensitive polymer composition and the wetting composition are applied simultaneously, optionally with subsequent addition of salt or other activating compounds to activate or further activate the binder.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

As used herein, the "thickness" of a web is measured with a 3-in acrylic plastic disk connected to the spindle of a Mitutoyo Digimatic Indicator (Mitutoyo Corporation, 31-19, Shiba 5-chome, Minato-ku, Tokyo 108, Japan) and which delivers a net load of 0.05 psi to the sample being measured. The Mitutoyo Digimatic Indicator is zeroed when the disk rests on a flat surface. When a sample having a size at least as great as the acrylic disk is placed under the disk, a thickness reading can be obtained from the digital readout of the indicator. Water-dispersible substrates of the present invention can have any suitable thickness, such as from about 0.1 mm to 5 mm. For wet wipes, thicknesses can be in the range of 0.2 mm to about 1 mm, more specifically from about 0.3 mm to about 0.7 mm. Thickness can be controlled, for example, by the application of compaction rolls during or after web formation, by pressing after binder or wetting composition has been applied, or by controlling the tension of winding when forming a roll good.

The use of the platen method to measure thickness gives an average thickness at the macroscopic level. Local thickness may vary, especially if the product has been embossed or has otherwise been given a three-dimensional texture.

EXAMPLE 1

Preparation of Sulfonate Anion Modified Acrylic Acid Terpolymer

Acrylic acid (43.3 g, 0.60 mol), AMPS (10.7 g, 0.052 mol), butyl acrylate (35.2 g, 0.27 mol), and 2-ethylhexyl acrylate (20 g, 0.11 mol) were dissolved in 55 g of acetone/water (70/30) mixture. An initiator, 2,2-azobisisobutyronitrile (AIBN) (0.51 g, $3.1 \times 10^{-3}$ mol), was dissolved in 20 ml of acetone. The monomer solution was deoxygenated by bubbling $N_2$ through the solution for 20 minutes. To a 1000 ml three-neck round bottom flask, equipped with a condenser, two addition funnels and a magnetic stirrer, was added 120 g of an acetone/water (70/30) mixture. The solvent was heated to gentle reflux under nitrogen. Monomers and initiator were added simultaneously from the addition funnels over a period of two hours. Polymerization was allowed to proceed for an additional two hours, at the end of which, the addition funnels and condenser were replaced with a distillation head and a mechanical stir rod to remove acetone. A steady stream of $N_2$ was kept during distillation while the temperature was increased gradually from about 65° C. to about 90° C. When the distillation was completed, 400 g of deionized water was added to reduce the viscosity of the polymer solution. A hazy, but uniform solution was obtained.

A total of nine polymers (Samples 1–9) were synthesized using the above-described procedure. NaOH (2.1 g, 0.052 mol) in 20 ml of water was added at room temperature to neutralize the AMPS component in the samples. The compositions of Samples 1–9 are summarized in Table 5 below. All percentages are given in mole percent.

TABLE 5

Sulfonate Anion Modified Acrylic Acid Terpolymers

| Sample | % AMPS | % NaAMPS | % AA | % BA | % EHA |
|---|---|---|---|---|---|
| 1 | 0.0 | 3.0 | 64.0 | 22.5 | 10.5 |
| 2 | 0.0 | 3.5 | 63.5 | 22.5 | 10.5 |
| 3 | 0.0 | 3.9 | 62.1 | 24.6 | 9.4 |
| 4 | 0.0 | 4.0 | 57.0 | 26.5 | 12.5 |
| 5 | 0.0 | 4.2 | 64.7 | 19.7 | 11.4 |
| 6 | 0.0 | 5.0 | 58.0 | 26.5 | 10.5 |
| 7 | 0.0 | 4.0 | 63.0 | 21.5 | 11.5 |
| 8 | 0.0 | 5.0 | 59.0 | 25.5 | 10.5 |
| 9 | 0.0 | 5.0 | 60.0 | 24.5 | 10.5 |

EXAMPLE 2

Preparation of an Acrylic Acid Terpolymer

An acrylic acid terpolymer was produced using the polymerization procedure outlined in Example 2 of U.S. Pat. No. 5,312,883. The following monomers were used: acrylic acid (50 g, 0.69 mol), butyl acrylate (25 g, 0.20 mol), and 2-ethylhexyl acrylate (25 g, 0.14 mol). The polymer was neutralized with 0.1 mole sodium hydroxide.

EXAMPLE 3

Preparation of Ion-sensitive Polymer Formulation

The polymers prepared in Table 5, Sample 9 and Example 2 above were combined with Dur-O-Set RB to form the ion-sensitive polymer formulations of the present invention. The polymer formulations were prepared as shown in Table 6 below.

TABLE 6

Ion-Sensitive Polymer Formulations

| Sample | % Terpolymer (Example 2) | % Modified Terpolymer (Table 5, Sample 9) | % EVA |
|---|---|---|---|
| 1 | 85.0 | 0.0 | 15.0 |
| 2 | 0.0 | 85.0 | 15.0 |
| 3 | 65.0 | 0.0 | 35.0 |
| 4 | 0.0 | 65.0 | 35.0 |
| 5 | 95.0 | 0.0 | 5.0 |
| 6 | 0.0 | 95.0 | 5.0 |
| 7 | 55.0 | 0.0 | 45.0 |
| 8 | 0.0 | 55.0 | 45.0 |
| 9 | 75.0 | 0.0 | 25.0 |
| 10 | 0.0 | 75.0 | 25.0 |

EXAMPLE 4

Solubility of Ion-sensitive Polymer Formulation

The sensitivity of the polymer formulations of Example 3 to divalent cations present in hard water were measured. Samples 1–10 of Example 3 are placed in a number of $CaCl_2$ solutions with a $Ca^{2+}$ concentration varying from <10 to 200 ppm. Following soaking for an hour, the solubility of each polymer is noted. The solubility results are given below in Table 7.

TABLE 7

Solubility Results

| | Solubility in $Ca^{2+}$ | | | |
|---|---|---|---|---|
| Sample | <10 ppm | 50 ppm | 100 ppm | 200 ppm |
| Sample 1 | 100 | 94 | 78 | 12 |
| Sample 2 | 100 | 100 | 98 | 91 |
| Sample 3 | 100 | 60 | 36 | 2 |
| Sample 4 | 99 | 100 | 97 | 90 |
| Sample 5 | 100 | 97 | 88 | 19 |
| Sample 6 | 100 | 100 | 99 | 90 |
| Sample 7 | 89 | 42 | 31 | 0 |
| Sample 8 | 100 | 96 | 96 | 90 |
| Sample 9 | 100 | 73 | 78 | 7 |
| Sample 10 | 100 | 100 | 100 | 90 |

In every case the film cast from the blend containing NaAMPS is more soluble than the film containing the acrylic acid terpolymer, especially as the calcium ion concentration increases.

EXAMPLE 5

Testing the Binding Strength of Polymer Formulations with and without Crosslinking For the pilot scale trials we used pulp based (CF 405 or NB 416 pulp form Weyerhaeuser) airlaid base-sheets bound together with 2–5% bico fibers. The bico fibers were either Type-255 (from KoSa Fibers of Salisbury, N.C.) with an activated polyethylene sheath and a polyester core or Danaklon fibers (from FiberVisions of Varde, Denmark) with a polyethylene sheath and a polypropylene core. Both kinds of bico fibers were 2–3 denier and cut to 6 mm length. The binder formulations were applied by spraying 12–15 weight percent solutions on to both sides of the above base-sheet. The strengths of the base-sheets under various conditions are reported after subtracting the base strength of the web due to the bico fibers. Table 8 reports the strengths of the base-sheets with different formulations in 0.4 weight percent NaCl (CDWT) as well as after a one hour soak in deionized water (S-CDWT):

TABLE 8

Tensile Strength

| Sample | % Terpolymer | % EVA | EVA Cross-linkable? | BW (gsm) | Binder Add-On (%) | Oven Temp (° C.) | CDWT (g/in) | S-CDWT (g/in) |
|---|---|---|---|---|---|---|---|---|
| 1 | 85 | 15 | Yes | 70 | 22 | 400 | 413 | 112 |
| 2 | 65 | 35 | Yes | 70 | 22 | 400 | 467 | 375 |
| 3 | 85 | 15 | Yes | 71 | 23 | 400 | 444 | 116 |
| 4 | 85 | 15 | Yes | 76 | 28 | 400 | 518 | 143 |
| 5 | 85 | 15 | No | 70 | 22 | 400 | 430 | 21 |
| 6 | 85 | 15 | Yes | 73 | 25 | 350 | 336 | 60 |
| 7 | 65 | 35 | Yes | 67 | 18 | 350 | 332 | 237 |
| 8 | 65 | 35 | Yes | 69 | 21 | 350 | 268 | 165 |
| 9 | 85 | 15 | Yes | 68 | 20 | 350 | 219 | 35 |
| 10 | 65 | 35 | Yes | 67 | 19 | 350 | 199 | 74 |
| 11 | 85 | 15 | No | 69 | 21 | 350 | 226 | 20 |
| 12 | 65 | 35 | No | 67 | 19 | 350 | 196 | 29 |

BW: Basis Weight
CDWT: Cross machine Direction Wet Tensile strength.
S-CDWT: CDWT after soaking for one hour in deionized water.

All the above codes would wet out better on first insult relative to a binder formulation containing 100% acrylic acid terpolymer. Also, the binder formulations which contain the EVA, spray much better than 100% acrylic acid terpolymer, leading to much improved binder distribution and penetration on the substrate. Significantly, those formulations that were not crosslinkable; i.e., Samples 5, 11 and 12, had S-CDWTs of less than 30 g/in.

EXAMPLE 6

Binder formulations are prepared having the compositions shown in Table 9 below. The binder formulations at 12 weight percent solids are sprayed on both sides of an airlaid web. The airlaid web is based on pulp (CF 405 from Weyerhaeuser). Table 9 shows the strength of the base-sheet in 0.9% NaCl solution (CDWT) and after a one hour soak in deionized water (S-CDWT). The effect on strength after aging the samples in salt solution over a period of up to 16 weeks is also shown. A preservative, such as Mackstat H66, is added to the samples to prevent mold growth on the basesheets as they age in the salt solution.

TABLE 9

Tensile Strength of Base-Sheet

| Sample | % Terpolymer | % EVA | BW (gsm) | Binder Add-On (%) | Oven Temp (° C.) | Aging Time (Weeks) | CDWT (g/in) | S-CDWT (g/in) |
|---|---|---|---|---|---|---|---|---|
| 1 | 85 | 15 | 73 | 25 | 440 | 0 | 488 | 14 |
| 2 | 85 | 15 | 73 | 25 | 440 | 16 | 393 | 11 |
| 3 | 65 | 35 | 64 | 25 | 440 | 0 | 358 | 16 |
| 4 | 65 | 35 | 64 | 25 | 440 | 12 | 369 | 21 |
| 5 | 55 | 45 | 64 | 25 | 440 | 0 | 364 | 28 |
| 6 | 55 | 45 | 64 | 25 | 440 | 12 | 354 | 32 |

The results in Table 9 indicate that the web does not lose initial properties even after extensive aging in the in-use salt solution when Dur-O-Set RB is used as the EVA. If a crosslinkable agent is present in the EVA, lower dispersibility results after aging the samples for a few weeks.

EXAMPLE 7

In FIG. 1 is shown the strength properties of the NaAMPS modified terpolymer, which is also dispersible in hard water (up to 200 ppm $Ca^{++}$/$Mg^{++}$ solution). A base-sheet based on 75 weight percent NaAMPS modified acrylic acid terpolymer (SSB) and 25 weight percent EVA (Dur-O-Set® RB) exhibits very good strength during use (in 1.5% or 4.0% NaCl solution) and disperses in very hard water. SSB-4 dispersed in hard water in 10 minutes. SSB-5 dispersed in hard water in 3 hours. NaAMPS-SSB is more viscous relative to Lion-SSB.

Tensile results for Examples 5 through 7 were obtained with an MTS tensile test device, the MTS 500/S unit (MTS Systems, Research Park, N.C.) using the Testworks™ 3.10 for Windows software. Instead of the normal 3-inch strip for testing, a 1-inch wide strip was used, cut to 6 inches in length. The gauge length between the rubber-coated jaws of the test device was 3 inches. Testing was operated at the specified crosshead speed of 12 in/min. The MTS device with the modified test procedure generally gives comparable results to the tensile test protocol previously described using 3-inch wide samples and the Thwing-Albert tester.

EXAMPLE 8

The addition of the co-binder polymer to the ion-sensitive polymer reduces the shear viscosity of the polymer blend compared to the shear viscosity of the ion-sensitive polymer alone. Table 10 illustrates the effect of the addition of various co-binder polymers to an acrylic acid terpolymer (SSB-2) in accordance with the present invention.

TABLE 10

Effect of the Addition of Various Co-Binder Polymers to SSB-2

| Polymer Blend | Viscosity @ 100 sec$^{-1}$ |
|---|---|
| 18 weight percent SSB-2 solids | Too high to measure: >100,000 cps |
| 15 weight percent sodium polyacrylate solids (MW = 250,000, 50% neutralization) | 10,000 cps |
| 12 weight percent neat SSB-2 | 80 cps |
| 12 weight percent blend of 80 parts by wt. SSB-2 and 20 parts by wt. Rhoplex NW 1715K | 25 cps |
| 12 weight percent blend of 80 parts by wt. SSB-2 and 20 parts by wt. Rovene | 28 cps |
| 12 weight percent blend of 80 parts by wt. SSB-2 and 20 parts by wt. Dur-O-Set RB | 20 cps |

Table 10 shows that the addition of Rhoplex® NW 1715K, Rovene® 4817 and Dur-O-Set® RB significantly reduce the shear viscosity of the SSB-2 acrylic acid terpolymer alone. The reduction in viscosity is not due to a mere dilution of the SSB-2, because the addition of sodium polyacrylate resulted in a significant increase in the shear viscosity of the SSB-2.

EXAMPLE 9

Dried solid bars were prepared from Rhoplex® NW 1715K, Rovene® 4817 and Dur-O-Set® RB. The bars were prepared by pouring a quantity of the polymer into a rectangular silicone mold an open rectangular silicone mold 1 cm wide, 4 cm long, and 3 mm deep. The polymer in the mold was then heated at 60° C. overnight. The dried polymer in the mold was then placed in a container with 30 ml of deionized water at about 23° C. and allowed to sit for one hour. None of the bars were dispersed in the deionized water.

Bar samples were then prepared from the sulfonate anion modified acrylic acid terpolymer (NaAMPS+SSB) blended separately with Rhoplex® NW 1715K, Rovene® 4817 and Dur-O-Set® RB. The polymer blends were made from 75% by weight sulfonate anion modified acrylic acid terpolymer and 25% by weight of the co-binder polymers. The bar samples were prepared in the same manner as described above. The bar samples were then added to deionized water. Each of the bar samples made from the following polymer blends; ie., NaAMPS+SSB/Rhoplex NW 1715K, NaAMPS+SSB/Rovene 4817 and NaAMPS+SSB/Dur-O-Set RB, dispersed in the deionized water within one hour.

EXAMPLE 10

A substrate in the form of an airlaid web was prepared on a commercial airlaid machine having a width of 66.5 inches. A DanWeb airlaid former with two forming heads was used to produce substrates having basis weights of about 60 gsm. Weyerhaeuser CF405 bleached softwood kraft fiber in pulp sheet form was used and fiberized in a hammermill, then formed into an airlaid web on a moving wire at a speed of 200 to 300 feet per minute. The newly formed web was densified by heated compaction rolls and transferred to a second wire, where the web was humidified with an atomized spray of water applying an estimated 5% moisture add on level immediately prior to a second heated compaction roll to further densify the web. The web was then transferred to an oven wire and sprayed on the top side with ion-sensitive polymer formulation mixture on the exposed surface of the web, applying 10% ion-sensitive polymer formulation solids relative to the dry fiber mass of the web.

The ion-sensitive polymer formulation mixture comprised water as the carrier with 12% binder solids, wherein the binder comprised 75% SSB4 as the ion-sensitive polymer formulation and 25% Rhoplex® NW-1715K latex emulsion (Rohm and Haas Corp.) as the co-binder polymer.

Spray was applied with a series of Quick Veejet® nozzles, Nozzle No. 730077, manufactured by Spraying Systems Co. (Wheaton, Ill.), operating at 95 psi. A spray boom over the web provided 13 such nozzles on 5.5-inch centers with a tip-to-wire distance of 8 inches. This arrangement yields 100% overlap of spray cones for the ion-sensitive polymer formulation solution of this trial.

After the web was sprayed, it was carried into an oven with through-flow of air at about 225° C. to dry the binder solution. The web then was transferred onto the underside of another oven wire, upon which it passed over another spray boom where more ion-sensitive polymer formulation solution was applied to the bottom side of the web to add another 10 weight percent solids relative to the dry fiber mass of the web. The web then passed through two successive dryer units where through-air drying with air at about 225° C. completed drying of the web. The pressure differential across the web was approximately 10 inches of water. The length of the three dryer sections, from first to third, respectively, was about 9, 10, and 6 feet.

The thickness of the web after drying was 1.14 mm (this number, like other physical properties reported here, can vary depending on the fibers, basis weight, and so forth). The machine direction dry tensile (MDDT) strength of the web was measured at 4.59 kg/3 in. The cross direction dry tensile (CDDT) strength of the web was measured at 3.82 kg/3 in with a CD stretch of 8.98%.

The dried and treated web was then trimmed to 60 inches width, reeled and later slit into 4-inch wide rolls, which were then treated with wetting composition and formed into coreless rolls suitable for use as a pre-moistened bath wipe. The wetting composition was sprayed uniformly on one side of the 4-inch wide web prior to reeling the web into rolls suitably sized for use. The wetting composition was 4 weight percent NaCl in deionized water.

The cross direction wet tensile (CDWT) at 4 weight percent saline was measured at 0.76 kg/3 in. The Soaked CDWT strength was effectively 0, as was the Soaked CD Stretch, meaning the sheet was fully dispersible.

EXAMPLE 11

The sheet formed was identical to that of Example 10 except that the fibers in the airlaid web were 75% softwood kraft and 25% PET fibers. The thickness of the web after drying was 1.35 mm. The machine direction dry tensile (MDDT) strength of the web was measured at 3.87 kg/3 in. The cross direction dry tensile (CDDT) strength of the web was measured at 2.84 kg/3 in with a CD stretch of 11.31%. The cross direction wet tensile (CDWT) at 4% saline was measured at 0.82 kg/3 in. The Soaked CDWT strength was effectively 0, as was the Soaked CD Stretch.

EXAMPLE 12

Additional examples were conducted according to Example 10, with the exception that Rovene latex emulsion was used as the co-binder polymer and the basis weight and fiber composition varied as shown in Table 11. The Soaked CDWT results were all 0, indicating a complete loss of tensile strength. Other results are shown in Table 11, where Pulp/PET designates the ratio of softwood to synthetic fibers in the substrate, BW is the basis weight in gsm, TH is the thickness in mm, and S-CDWT-M is the one-hour soak CD wet tensile test for a sample soaked in water containing 200 ppm of $Ca^{++}/Mg^{++}$ in a 2:1 ratio.

TABLE 11

Measurements for Examples 3A–3F.

| Run | Pulp/PET | BW | TH | MDDT | CDDT | CDWT | S-CDWT-M |
|---|---|---|---|---|---|---|---|
| 3A | 100/0 | 60.3 | 1.18 | 5.44 | 4.12 | 0.69 | 0 |
| 3B | 85/15 | 62.9 | 1.25 | 4.68 | 4.23 | 0.66 | 0 |
| 3C | 75/25 | 55.6 | 1.04 | 5.48 | 4.06 | 0.66 | 0 |
| 3D | 75/25 | 59.3 | 1.19 | 4.87 | 3.96 | 0.81 | 0.17 |
| 3E | 75/25 | 60.7 | 1.48 | 4.41 | 3.51 | 0.79 | 0.12 |
| 3F | 85/15 | 62.7 | 1.46 | 4.6 | 3.82 | 0.76 | 0 |

The non-zero S-CDWT-M values (soaked wet tensile in hard water) are non-zero for two trials with 25% PET fibers, suggesting that higher amounts of synthetic fibers can begin to compromise water dispersibility.

EXAMPLE 13

A pre-moistened wipe was made similar to that of Example 10, except that the co-binder polymer was a modified Elite® latex emulsion substantially free of crosslinking agents provided by National Starch. The basis weight of the web was 61.35, the thickness 1.21 mm, the MDDT 5.09 kg/3-in, the MD stretch 7.89%, the CDDT 3.90 kg/3-in, the CD stretch 9.50%, the CDWT in 4% saline 0.78 kg/3-in, the CDWT stretch 32.96%, and the residual strengths after one hour in both deionized water (S-CDWT) and hard water (S-CDWT-M) were 0 kg/3-in.

EXAMPLE 14

Particulate Addition

Pre-moistened wipes comprising the basesheet of Example 10 were prepared with a wetting composition comprising a slurry of particles. The particles were selected from the following products marketed by Presperse, Inc. (Piscataway, N.J.):

TABLE 12

Particles from Presperse, Inc. selected for use in pre-moistened wipes

| Name | Composition | Characteristics |
|---|---|---|
| MCP-45 | Mica and polymethyl methacrylate | Fine powder, platelets coated with microspheres, 13–17 microns |
| Sericite SL-012 | 98% mica, 2% methicone | Fine white powder, hydrophobic surface, 2–10 microns |
| Rose talc | Talc | White powder, 10–12 microns |
| Permethyl 104A | Iso-octahexacontane (polyisobutene) | |
| Cashmir K-II | Mica (97%), silica beads (3%), 0.3 microns | Fine white powder, platelets coated with microspheres, 10–14 microns |
| Synthecite FNK-100 | Synthetic fluorphogopite | Fine powder, 10–15 microns |
| Ganzpearl GMX-0610 | Methyl methacrylate crosspolymer | Spherical powder, 4.5–8.5 microns |
| Ganzpearl GS-0605 | Styrene/divinylbenzene copolymer | White powder, 4.5–8.5 microns |

TABLE 12-continued

Particles from Presperse, Inc. selected for use in pre-moistened wipes

| Name | Composition | Characteristics |
|---|---|---|
| Ganzpearl PS-8F | Styrene/divinylbenzene copolymer | 0.4 microns |
| Spheron N-2000 | Amorphous silica | White powder, 2–15 microns, low oil absorption |
| Spheron L-1500 | Amorphous silica | White powder, 3–15 microns, high oil absorption |

For each particle type in Table 12, five 1000-gram batches of wetting composition were prepared with particle concentrations of 0.5%, 1%, 2%, 5%, and 10% by weight. Each batch was prepared by adding the appropriate amount of deionized, filtered water to a 1.15-liter beaker (for the 5 batches, the water amounts were, respectively, 926.3 g, 921.3 g, 911 g, 881 g, and 831 g). A 2.5-inch magnetic stirring rod stirred the contents of the jar while residing on a Thermolyne Cimarec 2 stirrer, with stirring speed set to maximum to provide a strong central vortex in each of 5 jars. Each batch comprised 4 weight percent sodium chloride, added to the water as 40 g of salt; 1 weight percent (10 g) Amisoft ECS22-P acylglutamate surfactant (Ajinomoto, Tokyo, Japan); 0.5 weight percent (5 g) DC silicone emulsion (Dow Corning) added to the salt water and surfactant; 1 weight percent (10 g) Mackstat H 66 preservative (McIntyre Group, Chicago, Ill.); and 0.05 weight percent (0.5 g) of fragrance first mixed into 0.25 weight percent (2.5 g) of polysorbate 20, then mixed into the solution comprising the previous ingredients; and the respective amount of powder (from 0.5 to 10, weight percent or from 5 g to 100 g). The powder was added to the solution as it was being stirred and allowed to wet and become suspended over a period of about 30 minutes after addition of the powder. Some additional stirring by hand was needed for some of the powders to promote mixing. Once the powder was dispersed in the liquid, the pH was adjusted to 5.0 by adding malic acid, prepared at a strength of 50 weight percent in water. The pH was measured with a Cole Parmer Model 59002-00 pH/mV/° C. meter, with a Model 59002-72 KK8 electrode.

Each of the particle suspensions was then added to dried airlaid basesheets that had been treated with NaAMPS binder and a co-binder polymer according to Example 13. The add level was 200%, with application by spray on one side of the web. The moistened web was then sealed in plastic to sit overnight. Examination of the pre-moistened wipes treated with particulate suspensions as the wetting composition revealed that the particles generally remained in the wet wipe without the need for additional thickeners or polymeric retention aids. Squeezing the pre-moistened wipes, for example, yielded a mostly clear fluid apparently substantially devoid of particulates, in contrast to the milky suspensions used to wet the wipes. Generally, no visible residue appeared to be left of the hands after using the wipes. The particulates also generally improved opacity and appeared to slightly provide tactile property improvements (reduced tack, better rheological feel).

EXAMPLE 15

The role of ungelled starch particles in the wetting composition of the present invention was investigated as a means of reducing tackiness and improving surface feel for a pre-moistened wipe. Five wetting compositions containing tapioca starch were prepared according to the formulations in Table 13. Softwood airlaid webs according to Example 10 were wetted with the wetting composition with a 300% add-on level. (QS means "quantity sufficient" to achieve the desired pH).

TABLE 13

Formulations for five wetting compositions containing starch

| Water Phase | A | B | C | D | E |
|---|---|---|---|---|---|
| Water (Tap) | 76.9 | 71.9 | 68.9 | 66.9 | 96.45 |
| Laponite XLS | 2 | 2 | 2 | 2 | |
| Phospholipid CDM | | | | | 0.5 |
| Malic Acid (50% Solution) to pH 4 | 7 | 7 | 7 | 7 | |
| Tapioca 28-1810 | 10 | 15 | 18 | 20 | |
| DC 1784 | 1 | 1 | 1 | 1 | |
| Dragoco Fragrance 0/708768 | 0.1 | 0.1 | 0.1 | 0.1 | 0.05 |
| Mackstate H 66 | 0.5 | 0.5 | 0.5 | 0.5 | 0.5 |
| Sodium Chloride | 1.5 | 1.5 | 1.5 | 1.5 | 1.5 |
| Mackam 2C | 1 | 1 | 1 | 1 | 1 |
| Malic Acid (50% Solution) to pH 4 | QS | QS | QS | QS | QS |

The pre-moistened wipes comprising starch displayed reduced tackiness when handled with the human hand than did similar pre-moistened wipes without the starch. The wipes containing starch also felt smoother.

EXAMPLE 16

Additional pre-moistened wipes were prepared using the wetting compositions displayed in Table 14, one of which comprised starch as an additive and the other which comprised botanicals. The wetting composition was added to an airlaid fibrous substrate comprising an ion-sensitive binder. The wetting composition was added at add-on levels of 300 and 200 weight percent, respectively.

TABLE 14

Formulations for two wetting compositions

| Code | Starch | Botanical |
|---|---|---|
| formula # | 1 | 2 |
| Raw Materials | | |
| Water Phase | | |
| Water (Tap) | 61.4 | 95.45 |
| Laponite XLS | 2 | |
| Phospholipid CDM | | 0.5 |
| Malic Acid (50% Solution) to pH 4 | 7 | |
| Tapioca 28-1810 | 25 | |
| DC 1784 | 1 | 0.5 |
| Dragoco Fragrance 0/708768 | 0.1 | 0.05 |
| Mackstate H 66 | 1 | 0.5 |
| Sodium Chloride | 1.5 | 1.5 |
| Mackam 2C | 1 | |
| Malic Acid(50% Solution) to pH 4 | QS | QS |
| CS-22 | | 0.5 |
| Emulgin G | | 0.5 |
| Witch Hazel | | 0.5 |
| | 100 | 100 |
| pH-Final | | |
| Solution add-on | 300% | 200% |

EXAMPLE 17

Binder Specifications

A variety of ion-sensitive binders were prepared comprising acrylic acid (AA), butacrylic acid (BA), 2-ethylhexyl-acrylic acid, and AMPS, with the mole percents and molecular weights shown in Table 15:

TABLE 15

Ion-sensitive binders comprising AMPS

| SSB Code | $MW \times 10^{-6}$ | Mole percent of monomers: | | | |
|---|---|---|---|---|---|
| | | AA | BA | 2-EHA | AMPS |
| A | 1.54 | 60 | 24.5 | 10.5 | 5 |
| B | 1.32 | 60 | 24.5 | 10.5 | 5 |
| C | 0.604 | 60 | 24.5 | 10.5 | 5 |
| D | 0.548 | 60 | 24.5 | 10.5 | 5 |
| E | 0.609 | 60 | 24.5 | 10.5 | 5 |
| F | 0.545 | 60 | 24.5 | 10.5 | 5 |
| G | 1.21 | 62 | 24.5 | 8.5 | 5 |
| H | 0.79 | 60 | 24.5 | 10.5 | 5 |
| I | 0.916 | 60 | 24.5 | 10.5 | 5 |
| J | 0.71 | 60 | 24.5 | 10.5 | 5 |
| K | 0.786 | 60 | 24.5 | 10.5 | 5 |
| L | 0.845 | 60 | 24.5 | 10.5 | 5 |
| M | 0.640 | 60 | 24.5 | 10.5 | 5 |
| N | 0.800 | 60 | 24.5 | 10.5 | 5 |
| O | 0.635 | 60 | 24.5 | 10.5 | 5 |
| P | 0.610 | 60 | 24.5 | 10.5 | 5 |
| Q | 0.575 | 60 | 24.5 | 10.5 | 5 |
| R | 0.638 | 60 | 24.5 | 10.5 | 5 |
| S | 0.912 | 62 | 26.5 | 7.5 | 4 |
| T | 0.609 | 60 | 25.5 | 10.5 | 4 |
| U | 0.835 | 58 | 27 | 10 | 5 |
| V | 0.675 | 58 | 27 | 10 | 5 |
| W | 0.734 | 58 | 27 | 10 | 5 |
| X | 0.716 | 58 | 27 | 10 | 5 |
| Y | 0.650 | 58 | 27 | 10 | 5 |
| Z | 0.718 | 58 | 27 | 10 | 5 |
| AA | 0.518 | 58 | 27 | 10 | 5 |
| AB | 0.544 | 58 | 27 | 10 | 5 |

These binders were prepared according to the methods of Example 1, but scaled up as a batch process capable of producing several hundred gallons per batch.

EXAMPLE 18

Typical Wetting Solution

A wetting composition was prepared by combining the following ingredients according to the specific weight percent: 92.88 weight percent deionized water, 4 weight percent NaCl, 1 weight percent Mackstat H-66 preservative (McIntyre Group, Chicago, Ill.), 1 weight percent CS22 acyl glutamate anionic surfactant (Amisoft Corp., Tokyo, Japan), 0.5 weight percent DC 1785 silicone emulsion (Dow Corning), 0.25 weight percent Solulan L-575 (PEG-75 lanolin, available from Amerchol, a division of Union Carbide), 0.05 weight percent Dragoco fragrance 0/708768 (Dragoco S A, Cuautitlán Izcalli, D. F. Mexico, Mexico), 0.25 weight percent polysorbate 20, and about 0.07 weight percent of 50 percent by weight malic acid solution to bring the pH to 5.0.

EXAMPLE 19

A Treated Substrate

An airlaid substrate was made with the equipment described for Example 10. Basis weight was 65 gsm and the fibers were 100% Weyerhaeuser CF405 bleached softwood kraft pulp. The binder solution had 12.8 weight percent binder solids, 75 weight percent of which was SSB Code H of Table 15 and 25 weight percent Dur-O-Set RB latex co-binder (National Starch). The binder solution was sprayed onto the web as described in Example 1, with the dryer air temperature at 215° C. for all three oven sections.

EXAMPLE 20

A Treated Substrate

An airlaid substrate was made according to Example 10, except that the basis weight was 63 gsm and the oven temperature was 227° C. Reel speed was 197 fpm. Thickness of the dried web was 1.30 mm.

MDDT was 5.55 kg/3-in, CCDT was 4.83 kg/3-in, CDWT (in 4% NaCl solution) was 1.07 kg/3-in, and S-CDWT as well as S-CDWT-M (1 hour soak tests) gave 0 kg/3-in.

Some of the dried web was slit to a 4.25-inch width and treated with wetting composition at 225% add-on, comprising 4% NaCl in deionized water without surfactant. The moistened web was perforated with a perf-knife operating with a depth of 0.070 inches to perforate every 4.5 inches. The perforated web was rolled into a coreless roll with 100 perforated sheets per roll (approximately 37.5 feet per roll) and placed in a white plastic cartridge for subsequent use in a dispenser for pre-moistened wipes.

EXAMPLE 21

A portion of the dried, treated web of Example 20 was wetted with the wetting composition of Example 18 and converted into perforate roll form for use as pre-moistened wipes to be dispensed from a bathroom dispenser.

Comparative Example 22

A conventional, adhesively bonded airlaid substrate with a basis weight of 60.1 gsm was created using the methods described in Example 10. Dur-O-Set E-646 (National Starch) was used with wood pulp (CF405) The substrate was wetted with a 4% NaCl solution and tested using the methods described. The binder was entirely the self-crosslinking Dur-O-Set E-646 compound; no salt-sensitive binder was applied. The binder solids mass was 17% of the substrate mass. Dry thickness of the web was 1.4 mm, and the CDWT value was 1.3 kg/3-in, while S-CDWT was 1.2 kg and S_CDWT-M was 1.15 kg, indicating that the web maintained nearly all of its strength after soaking, and suggesting that the crosslinked latex provided the majority of the tensile strength of the web and that the latex bonds did not weaken substantially in water.

EXAMPLE 23

A variety of binder/co-binder combinations were prepared, as described below, using the salt-sensitive binders of Table 15 and co-binders as shown in Table 16 which are not self-crosslinkable.

TABLE 16

Latex co-binders that are not self-crosslinkable.

| Co-binder ID | Co-binder | Manufacturer |
| --- | --- | --- |
| 1 | Dur-O-Set RB | National Starch |
| 2 | Rhoplex NW-1715K | Rohm and Haas |
| 3 | Rovene 4817 | Mallard Creek |

Using the methods described in Example 10, airlaid substrates were made from bleached kraft fibers. The substrate was wetted with a 4% NaCl solution and tested using the methods described. All substrates were comprised of wood pulp (CF405) and binder. Results are shown in Table 17, where the binder mixture consistently comprised 75% of a salt-sensitive binder selected from Table 15 and 25% of a co-binder selected from Table 16. The binder/co-binder column refers to the binder and co-binders listed in Table 15 and 16, respectively. For example, "A/1" refers to a mixture of SSB Code A in Table 15 and co-binder 1 of Table 16.

TABLE 17

Tensile data for various binder systems.

| % Binder | Binder/ Cob. | SSB MW × $10^{-6}$ | BW (gsm) | Thick. (mm) | CDWT (kg/3") | S-CDWT (kg/3") | S-CDWT-M (kg/3") | S-CDWT-M3 3 hrs (kg/3") |
| --- | --- | --- | --- | --- | --- | --- | --- | --- |
| 16.7 | A/1 | 1.54 | 71.3 | 1.46 | 0.990 | 0 | 0.330 | 0.180 |
| 20 | B/1 | 1.32 | 63.3 | 1.25 | 1.242 | 0.163 | 0.470 | 0.310 |
| 20 | B/1 | 1.32 | 66.6 | 1.46 | 1.040 | 0 | 0.230 | 0.550 |
| 20 | G/1 | 1.21 | 62.2 | 1.20 | 1.002 | 0 | 0.270 | 0 |
| 20 | H/1 | 0.79 | 63.1 | 1.3 | 1.070 | 0 | 0 | 0 |
| 16.7 | C/1 | 0.604 | 73.6 | 1.59 | 0.750 | 0 | 0 | 0 |
| 20 | C/1 | 0.604 | 71.2 | 1.5 | 0.900 | 0 | 0 | 0 |
| 20 | C/1 | 0.604 | 61.1 | 1.28 | 1.140 | 0 | 0 | 0 |
| 20 | D/1 | 0.548 | 62.5 | 1.32 | 0.900 | 0 | 0 | 0 |

As seen in Table 17, nearly all of the substrates have lost more that 80% of their tensile strength after soaking in deionized water for 1 hour (S-CDWT). The substrates have lost more that 60% of their strength (S-CDWT-M) after soaking for 1 hour in a solution of 200 ppm of divalent cations (Ca++/Mg++ 2:1). In particular, for the runs shown in Table 17, the samples completely lost their strength in 1 hour in the 200 ppm solution when the molecular weight of the salt sensitive binder was less than 1,200,000. After 3 hours of soak time in the 200 ppm divalent cation solution, the SSBs with high molecular weight have generally lost more of their strength, but may still have non-zero tensile strength.

By comparison, the comparative Example 22 lost less than 15% of its strength after soaking for 1 hour in either deionized water or 200 ppm divalent ion solution. All of the substrates in Table 17 lost more tensile strength on soaking than the comparative Example 22.

EXAMPLE 24

Different co-binders from Table 16 were blended with the salt-sensitive binder Code F from Table 15. The binder blend was then applied using the methods described in Example 10 to create the airlaid substrates listed in Table 18. In each case, 20% binder solids were applied to the substrate in a blend of 75% SSB/25% co-binder

TABLE 18

Tensile data for various co-binder systems.

| Binder/Co-binder | Co-binder Used | BW (gsm) | Thick, (mm) | CDWT (kg/3") | S-CDWT (kg/3") | S-CDWT-M (kg/3") |
|---|---|---|---|---|---|---|
| F/1 | Dur-O-Set RB | 59.77 | 1.06 | 0.735 | 0 | 0 |
| F/2 | Rhoplex | 60.83 | 1.14 | 0.758 | 0 | 0 |
| F/3 | Rovene | 60.28 | 1.18 | 0.687 | 0 | 0 |

Under similar run conditions, all three co-binders perform comparably. All of the substrates have lost their tensile strength (S-CDWT-M) in the 200 ppm divalent cation solution independent of co-binder type.

EXAMPLE 25

Measurements were made of the peel force required to unroll the product from the outer layers of a coreless roll of pre-moistened wipes suitable for use as a moist toilet paper product. The product was made according to Example 10 with an add-on level of 200% wetting composition.

The dried web was slit to a 4.25-inch width and treated with wetting composition at 200% add-on, comprising 4% NaCl in deionized water with surfactants, silicone, and lanolin as listed in Table 19 for wetting composition Q, R, and S. The moistened web was perforated with a perf-knife operating to perforate every 4.5 inches. The perforated web was rolled into a coreless roll with 100 perforated sheets per roll (approximately 37.5 feet per roll) and sealed in a plastic cartridge for subsequent use in a dispenser for pre-moistened wipes.

TABLE 19

Other additives in three wetting compositions.

| Solution | Silicone emulsion | Lanolin | Acylglutamate surfactant |
|---|---|---|---|
| Q | 0.50% | 0.25% | CS22 |
| R | 1.00% | 0.25% | ECS 22P |
| S | 1.00% | 0% | ECS 22P |

The roll rested freely in a plastic tub with a rounded, ribbed bottom that held the roll in place with a minimum of friction when the roll was unwound by pulling vertically upwards on the tail end of the roll. Adjacent plies adhered to each other such that some force was required to separate the layers. The peel force needed was less than the weight of the roll and appeared to be substantially greater than the frictional resistance offered by the tub as the roll turned, evidenced in part by angle between the web and the roll at the point of separation. With no peel force, the angle between the web being pulled up and a line normal to the roll at the point of separation would be 90 degrees, but in unwinding the moist roll with the salt-sensitive binder, the angle was substantially less than 90 degrees, thus imparting peel force to separate the web.

The peel force was measured with an MTS Sintech 1/G test machine with TestWorks 3.10 software. All testing as done in a conditioned laboratory under Tappi Standard conditions. A 4.5-inch wide clamp with rubber surfaces gripped the tail of a roll, with the roll position directly underneath the clamp such the tail would remain vertical as it was unwound from the roll if there were no peel force causing the web to wrap a portion of the roll and deflect from the vertical. The clamp was attached to the crosshead, which pulled the tissue web upward at a speed of 100 cm/minute. Peel force was measured by a 50 N load cell. The average load to pull 18 sheets away from the roll was recorded by averaging two runs in which 4 sheets each were seperated and two runs in which 5 sheets each were separated. Only the first 18 sheets from the roll were used in the measurement. The average peel force for two rolls per condition (for an overall average taken over a total of 36 sheets) is reported in Table 20 below.

TABLE 20

Peel force in grams to remove a web from a wound moist roll.

| BW, gsm | Thickness, mm | Binder add-on | Solution | MDWT, g/in | Peel force, g |
|---|---|---|---|---|---|
| 65 | 1.1 | 22% | Q | 500 | 167 |
| 65 | 1.1 | 22% | R | 475 | 170 |
| 65 | 1.1 | 22% | S | 533 | 162 |
| 60 | 0.76 | 20% | Q | 438 | 131 |
| 55 | 0.76 | 20% | Q | 353 | 106 |
| 55 | 0.76 | 20% | R | 341 | 120 |
| 55 | 0.84 | 20% | R | 385 | 115 |

Peel forces for a roll having a width between 7 and 15 cm (the width of the rolls tested in Table 20 are 10.8 cm) are desirably are less than 500 g, more specifically less than 300 g, more specifically less than about 200 g, more specifically still less than about 160 g, most specifically less than about 120 g, with an exemplary range of from about 50 g to about 350 g, or from about 80 g to about 200 g. More generally, the peel force per 4-inch width of a moist roll can be any of the aforementioned values of ranges.

EXAMPLE 26

Additional samples were prepared according to Example 24 above, except that 15 weight % of the fiber blend consisted of 6-mm, crimped PET fibers (KoSa). Different co-binders from Table 16 were blended with the salt-sensitive binder Code F from Table 15. The binder blend was then applied using the methods described in Example 10 to create the airlaid substrates whose properties are listed in Table 21. In each case, 20% binder solids were applied to the substrate in a blend of 75% SSB/25% co-binder. The properties of these substrates were measured after wetting with a 4% NaCl solution. All three co-binders perform comparably. All of the substrates have lost their tensile strength in 200 ppm divalent cation solution independent of co-binder type. Compared to the parallel results in Example 24, incorporation of the synthetic fibers impart a slight to modest strength improvement (CDWT) and a modest increase in dry bulk.

TABLE 21

Data for substrates with PET fibers and various co-binders.

| Binder/Co-binder | Co-binder Used | BW (gsm) | Thick, (mm) | CDWT (kg/3") | S-CDWT (kg/3") | S-CDWT-M (kg/3") |
|---|---|---|---|---|---|---|
| F/1 | Dur-O-Set RB | 63.32 | 1.31 | 0.782 | 0 | 0 |
| F/2 | Rhoplex | 62.07 | 1.35 | 0.820 | 0 | 0 |
| F/3 | Rovene | 62.90 | 1.25 | 0.660 | 0 | 0 |

EXAMPLE 27

Additional examples were conducted according to Example 26 with increasing amounts of synthetic fiber being added to the fiber blend. Either a 6 mm crimped PET fiber (KoSa) or a 6 mm, crimped 2.4 dtex, Lyocell fiber was used as noted in Table 22 below. The binder blend was a constant blend of 75% SSB and 25% co-binder.

TABLE 22

Data for substrates with PET fibers and various co-binders.

| Pulp/Synth. | Synth. Type | Binder % | Binder/Co-binder | BW (gsm) | Thick. (mm) | CDWT (kg/3") | S-CDWT (kg/3") | S-CDWT-M (kg/3") |
|---|---|---|---|---|---|---|---|---|
| 100/0 | None | 20% | F/3 | 60.28 | 1.18 | 0.687 | 0 | 0 |
| 85/15 | PET 6 mm | 20% | F/3 | 62.90 | 1.25 | 0.660 | 0 | 0 |
| 75/25 | PET 6 mm | 20% | F/3 | 59.32 | 1.19 | 0.805 | 0 | 0.170 |
| 75/25 | PET 6 mm | 20% | F/3 | 60.65 | 1.48 | 0.790 | 0 | 0.120 |
| 85/15 | PET 6 mm | 20% | F/3 | 62.67 | 1.46 | 0.757 | 0 | 0 |
| 85/15 | Lyocell- 6 mm | 19% | E/2 | 58.3 | 1.08 | 0.969 | 0 | 0 |
| 75/25 | Lyocell- 6 mm | 19% | E/2 | 59.2 | 1.09 | 1.080 | 0 | 0.127 |

The non-zero soaked CDWT tensiles in 200 ppm of divalent cation are non-zero for those trial combinations with 25% synthetic fiber (PET or Lyocell), suggesting that higher amounts can begin to compromise water dispersibility.

EXAMPLE 28

The substrates shown in Table 23 were all made according to the methods of Example 10 and prepared according to the methods described in Example 23. All of the substrates in Table 23 were formed from airlaid pulp (CF405). All binder blends were 75% SSB and 25% co-binder. The dry thickness of the sheet was controlled by adjusting the level of web compaction by the two compaction rolls prior to the first spray application of binder. SSB Codes O and Q from Table 15 were used.

TABLE 23

Data for substrates with PET fibers and various co-binders.

| % Binder in sheet | Binder/Cob. | BW (gsm) | Thick. (mm) | CDWT (kg/3") | S-CDWT (kg/3") | S-CDWT-M (kg/3") |
|---|---|---|---|---|---|---|
| 20 | O/1 | 66.0 | 1.27 | 1.055 | 0 | 0 |
| 20 | O/1 | 68.2 | 0.77 | 1.550 | 0 | 0 |
| 20 | O/1 | 52.5 | 1.19 | 0.728 | 0 | 0 |
| 20 | Q/1 | 54.19 | 0.75 | 1.372 | 0 | 0 |
| 17 | Q/1 | 57.5 | 0.89 | 1.110 | 0 | 0 |
| 20 | Q/1 | 59.90 | 0.75 | 1.583 | 0 | 0 |
| 20 | Q/1 | 65.36 | 0.76 | 1.696 | 0 | 0 |
| 20 | Q/1 | 66.43 | 1.20 | 1.296 | 0 | 0 |

It appears that compaction of the dry web prior to binder application can significantly increase final sheet wet strength without sacrificing dispersibility. This unexpected level of strength increase can allow equivalent wet tensiles to be achieved in a variety of combinations including basis weight reduction and/or percent binder in sheet reductions.

EXAMPLE 29

All substrates were prepared according to the methods described in Example 27. All substrates were comprised of the fiber blend noted in Table 24 with 20% binder in the sheet and Dur-O-Set RB serving as the co-binder. Synthetic fibers were crimped and either 6 mm PET (KoSa) or 6 or 8 mm Lyocell with 1.7 or 2.4 dtex (Accordis).

TABLE 24

Data for substrates with various fibers and binders.

| Code | % Syn. Fiber | Syn. Fiber | Binder/ Cob. | SSB MW | BW (gsm) | Thick. (mm) | CDWT (kg/3") | S-CDWT (kg/3") | S-CDWT-M (kg/3") |
|---|---|---|---|---|---|---|---|---|---|
| 2701 | 0 | none | F/1 | 545000 | 59.8 | 1.06 | 0.735 | 0 | 0 |
| 2702 | 15 | PET | F/1 | 545000 | 63.3 | 1.31 | 0.782 | 0 | 0 |
| 2713 | 15 | L-2.4-6 | F/1 | 545000 | 62.0 | 1.39 | 0.840 | 0 | 0 |
| 2714 | 15 | L-1.7-6 | F/1 | 545000 | 61.8 | 1.33 | 0.768 | 0 | 0 |
| 2715 | 15 | L-1.7-8 | F/1 | 545000 | 63.7 | 1.47 | 0.842 | 0 | 0 |
| 2716 | 0 | none | J/1 | 710000 | 65.5 | 1.11 | 1.193 | 0 | 0 |
| 2717 | 15 | L-1.7-8 | J/1 | 710000 | 61.4 | 1.02 | 1.512 | 0 | 0.200 |
| 3010 | 0 | none | R/1 | 638000 | 61.10 | 0.80 | 1.710 | 0 | 0 |
| 3015 | 15 | PET | R/1 | 638000 | 62.23 | 0.86 | 1.769 | 0 | 0.070 |
| 3016 | 5 | L-1.7-8 | R/1 | 638000 | 60.63 | 0.79 | 2.620 | 0 | 0.170 |

The examples of Table 24 suggest that that synthetic fiber length, SSB molecular weight and web compaction in combination can affect the dispersibility of the product as indicated by its S-CDWT-M value. All substrates comprised of the 6 or 8 mm synthetic fibers were dispersible with the lower molecular weight SSB. As the molecular weight was increased, the 8 mm Lyocell substrate began to retain some of its strength after soaking for 1 hour in the divalent cation solution; this substrate, however, was dispersible in DI water. Densifying the dry web prior to binder application can also impact the dispersibility of a synthetic fiber containing substrate (Codes 3015 and 3016). Both Code 3015 and Code 3016 were fully dispersible in the DI water. Sheet dispersibility can be managed by choosing lower molecular weight SSBs in combination with synthetic fibers and dry web densification.

EXAMPLE 30

The substrates listed in Table 25 were prepared, wetted with 4% NaCl solution, and tested according to the methods described in Example 29. Each substrate was comprised of the fiber blend noted and 20% binder with the SSB/co-binder blend noted in Table 25. Dur-O-Set RB was the co-binder used in all of the samples listed in Table 25. All codes used 100% softwood fiber except the last one, Code 2813, which comprised 15% PET fiber (the 6 mm, crimped fiber obtained from KoSa). Basis weight was generally held constant to about 60 gsm. The thickness of the airlaid web was controlled by adjusting the level of web compaction by the two compaction rolls prior to the first spray application of binder. The dry CD stiffness of selected substrates in Table 25 were measured using a Handle-o-meter and reported as stiffness.

TABLE 25

Data for substrates with various binder blends.

| Code | Binder/ Cob. | Bind. Type | BW (gsm) | Thick. (mm) | CDWT (kg/3") | S-CDWT (kg/3") | S-CDWT-M (kg/3") | Stiffness g force |
|---|---|---|---|---|---|---|---|---|
| 3025 | 100/0 | R | 58.42 | 1.23 | 1.003 | 0 | 0 | 200 |
| 3026 | 100/0 | R | 58.68 | 0.76 | 1.953 | 0 | 0 | 214 |
| 3007 | 75/25 | R | 60.23 | 1.19 | 0.942 | 0 | 0 | 189 |
| 3008 | 75/25 | R | 59.38 | 1.03 | 1.161 | 0 | 0 | |
| 3009 | 75/25 | R | 59.73 | 0.92 | 1.243 | 0 | 0 | |
| 3010 | 75/25 | R | 61.10 | 0.80 | 1.713 | 0 | 0 | 181 |
| 3021 | 65/35 | R | 62.24 | 1.17 | 0.988 | 0 | 0.050 | 177 |
| 3022 | 65/35 | R | 62.07 | 0.81 | 1.800 | 0.030 | 0.200 | 167 |
| 3024 | 55/45 | R | 58.95 | 1.23 | 0.853 | 0 | 0.100 | 145 |
| 3023 | 55/45 | R | 59.01 | 0.78 | 1.608 | 0.150 | 0.230 | 141 |
| 2812 | 65/35 | P | 59.1 | 1.37 | 0.735 | 0 | 0 | |
| 2813 | 65/35 | P | 59.4 | 1.41 | 0.723 | 0 | 0 | |

As the percentage of the salt sensitive binder in the blend is decreased from 100% to 55% there is only to modest decrease in the CDWT at constant dry bulk. At compositions of 65% salt-sensitive binder in the binder blend, the substrate begins to retain a greater portion of its wet strength after soaking for 1 hour in 200 ppm of the divalent cation solution. As the web is densified prior to the first binder application and the percentage of salt sensitive binder in the blend is reduced to 65% or lower, a greater amount of strength is retained after soaking in DI water or the 200 ppm divalent cation solution for 1 hour compared to the same compositions at a higher dry bulk. These examples suggest that increasing the co-binder content with or without additional densification of the web can begin to compromise substrate dispersibility.

The results in Table 25 also show significant CDWT increases as the thickness of the dry web is compressed prior to the application of the binder. Codes 3007 to 3010 show that the CDWT is increasing as a function of decreasing dry bulk with no loss of substrate dispersibility at constant binder conditions.

Based on the Handle-O-Meter results (stiffness), it appears that as the percentage of salt sensitive binder in the blend is decreased, the CD stiffness of the substrate decreases.

EXAMPLE 31

The substrates listed in Table 26 were prepared according to the method described in Examples 10 and 23. Each substrate comprised pulp (CF405) and 20% binder. The binder had the SSB/co-binder blend given in Table 26. Dur-O-Set RB was the co-binder. The substrate was converted into roll form and wetted with solution Q of Table 19 (solution D). Measurements were made of the peel force required to unroll the product from the outer layers of the coreless roll of pre-moistened wipes according to the method described in Example 25. The results of these tests are recorded in Table 26 below.

TABLE 26

Peel force results for coreless rolls.

| Code | % Binder In sheet | Binder Blend | Binder/ Cob. | BW (gsm) | Thick. (mm) | Peel (g) |
|---|---|---|---|---|---|---|
| 3026 | 20 | 100/0 | R/1 | 58.68 | 0.76 | 142 |
| 3010 | 20 | 75/25 | R/1 | 61.10 | 0.80 | 139 |
| 3022 | 20 | 65/35 | R/1 | 62.07 | 0.81 | 116 |
| 3023 | 20 | 55/45 | R/1 | 59.01 | 0.78 | 111 |

In this case, decreasing the percentage of the salt-sensitive binder in the blend decreased the peel force.

EXAMPLE 32

Samples were made as in Example 10 using 75/25 blends of SSB binder (see Table 15) and Dur-O-Set RB co-binder (co-binder 1 of Table 16), according to the information in Table 27 below. Tensile results in Table 27 show good dispersibility over a range of product conditions.

TABLE 27

Tensile results for a range of binders and basesheet properties.

| % Binder | Binder/ Cob. | SSB MW | BW (gsm) | Thick. (mm) | CDWT (kg/3") | S-CDWT (kg/3") | S-CDWT-M (kg/3") |
|---|---|---|---|---|---|---|---|
| 20 | O/1 | 632000 | 52.5 | 1.19 | 0728 | 0 | 0 |
| 20 | Q/1 | 575000 | 54.19 | 0.75 | 1.372 | 0 | 0 |
| 15.2 | J/1 | 710000 | 55.2 | 1.47 | 0.320 | 0 | 0 |
| 24 | L/1 | 834000 | 60.4 | 0.92 | 1.070 | 0 | 0 |
| 20 | D/1 | 548000 | 62.5 | 1.32 | 0.900 | 0 | 0 |
| 20 | H/1 | 790000 | 63.1 | 1.3 | 1.070 | 0 | 0 |
| 22 | R/1 | 638000 | 66.47 | 0.76 | 2.273 | 0 | 0 |
| 20 | C/1 | 604,000 | 74.4 | 1.47 | 1.120 | 0 | 0 |

The samples reported in Table 27 demonstrate some of the ranges of binder content, basis weight, and web thickness over which dispersible substrates can be made.

EXAMPLE 33

Samples were made generally as in Example 10 using 75/25 blends of SSB binder (see Table 15) and co-binder (see Table 16) as noted in Table 28. All substrates contain 6 mm crimped, 2.4 dtex Lyocell (Accordis) as 15% of the fiber blend with 85% softwood pulp (CF405). All substrates are comprised of 19% binder and 81% of the binder blend.

TABLE 28

Tensile results for a range of binders and basesheet properties.

| Binder/ Cob. | SSB MW. | BW (gsm) | Thick. (mm) | CDWT (kg/3") | S-CDWT (kg/3") | S-CDWT-M (kg/3") |
|---|---|---|---|---|---|---|
| L/1 | 845,000 | 61.1 | 1.17 | 0.960 | 0 | 0 |
| W/1 | 734,000 | 60.2 | 1.17 | 0.960 | 0 | 0.198 |
| AB/1 | 544,000 | 56.2 | 0.95 | 1.060 | 0 | 0 |
| AB/2 | 544,000 | 58.6 | 1.06 | 0.990 | 0 | 0.205 |
| E/2 | 609,000 | 58.3 | 1.08 | 0.969 | 0 | 0 |

In Table 28, all samples lost at least 75% of their wet strength after soaking in the 200 ppm divalent cation solution for 1 hour (S-CDWT-M). The main differences in these samples is in the SSB composition, as depicted in Table 15. Salt-sensitive binders L and E have the same composition, but different molecular weights, than the salt sensitive binders W and AB (see Table 15). Salt sensitive binders W and AB have the same composition but different molecular weights. The W/1- and AB/2-treated substrates appear to be less dispersible than the L/1- and E/2-treated substrates independently of co-binder. Reducing the salt sensitive binder's molecular weight can be used to make the substrate more dispersible as is shown by substrate AB/1. Or, changing the salt sensitive binder's composition can be used to make the substrate more dispersible as demonstrated by L/1 and E/2. Thus, by modifying the salt sensitive binder's molecular composition or its molecular weight, fully dispersible blends can be made. Alternatively, by selecting a different co-binder chemistry to be more compatible with the salt sensitive binder, fully dispersible binder blends can be made as demonstrated by substrates AB/2 and AB/1.

EXAMPLE 34

A latex emulsion comprising about 6% NMA crosslinker, AirFlex 105 (Air Products, Allentown, Pa.), was combined with SSB Code H of Table 15 at a ratio of 75 parts SSB to 25 parts latex solids and cast into 8 bars with dimensions 1 cm×4 cm×3 mm as described in Example 9. Four bars were prepared by drying in air at 60° C. overnight, while the other four bars were dried at 167° C. for 3 hours. Two bars from each set were then each placed in 30 ml of 4% NaCl solution and allowed to sit for one hour, after which solubility was determined gravimetrically. Bars from both sets (the two drying conditions) were essentially completely insoluble in the saline solution. The remaining bars from each set were each placed in 30 ml of hard water containing 200 ppm calcium and magnesium ions at a 2:1 ratio at about 23° C. and allowed to sit for one hour. The two bars dried at 167° C. and placed in hard water were essentially completely insoluble (0% soluble). The two bars dried at 60° C. and placed in hard water were 54% and 53% soluble, respectively, which was unexpectedly low given that the latex should be substantially uncrosslinked for drying at this temperature. However, some coagulation occurred when the latex was mixed with the SSB, suggesting a possible compatibility problem between the two mixtures, and thus solubility may be impaired, or some coagulated particles may not have passed through the filter paper. It is also possible that some of the NMA crosslinker in the Airflex latex may have promoted crosslinking or gelling of the blend. While it is believed that a more compatible latex emulsion would have yielded higher solubility, it is also believed that co-binders that are relatively low in crosslinking agents (e.g., less than 6%, specifically less than 2%, more specifically less than 1%, and most specifically less than 0.3% crosslinker on a solids mass basis) can be helpful in maintaining high solubility of the dried polymer blend.

FIG. 1 shows the wet tensile results for treated airlaid basesheets, wherein the tests have been carried out in different saline solutions or hard water. The airlaid basesheets were prepared according to Example 10 and provided with 20% add-on of salt-sensitive binder compositions labeled as Code X, Code Y, and Code Z. Code X is a binder polymer comprising 60% acrylic acid, 10.5% 2-ethylhexyl acrylate, 24.5% butyl acrylate, and 5% NaAMPS, polymerized according to Example 1 with a molecular weight of 1.3 million, corresponding to Code B in Table 15. Code Y is similar but with a molecular weight of about 550,000, corresponding to Code D in Table 15. Code Z is similar but has 62% acrylic acid and 8.5% 2-ethylhexyl acrylate as monomers, with a molecular weight of about 1.2 million, corresponding to Code G in Table 15. All binders were blended with Dur-O-Set RB co-binder in a 75:25 ratio. The treated webs were dried, as in Example 10, and then wetted with either a 4% or 1.5% NaCl solution. Wet tensile testing was conducted according to the CDWT protocol with the exceptions described in Example 5 (e.g., a 1-inch wide strip and a MTS tensile tester were used).

Soaked CD tensile tests were conducted on samples prepared with the 4% solution. The four columns shown for each code (some of which are not visible due to zero values) correspond to the results from the four different tests. The first two columns are the CDWT values "as is" for the web in either the 4% or 1.5% NaCl solution. The third and fourth columns are the S-CDWT-M (hard water soak) results at 1 hour and 3 hours for each web that had been wetted with the 4% solution.

The results show good wet strength at both 1.5% NaCl and 4% NaCl, with excellent strength loss for webs treated with Code Y (Hard Water Dispersibility of 100%), good strength loss for Code Z, and residual strength still present for Code X. Comparison of Code X to Code Y suggests that a reduction in molecular weight can promote dispersibility of the salt-sensitive binder.

Figure 2:
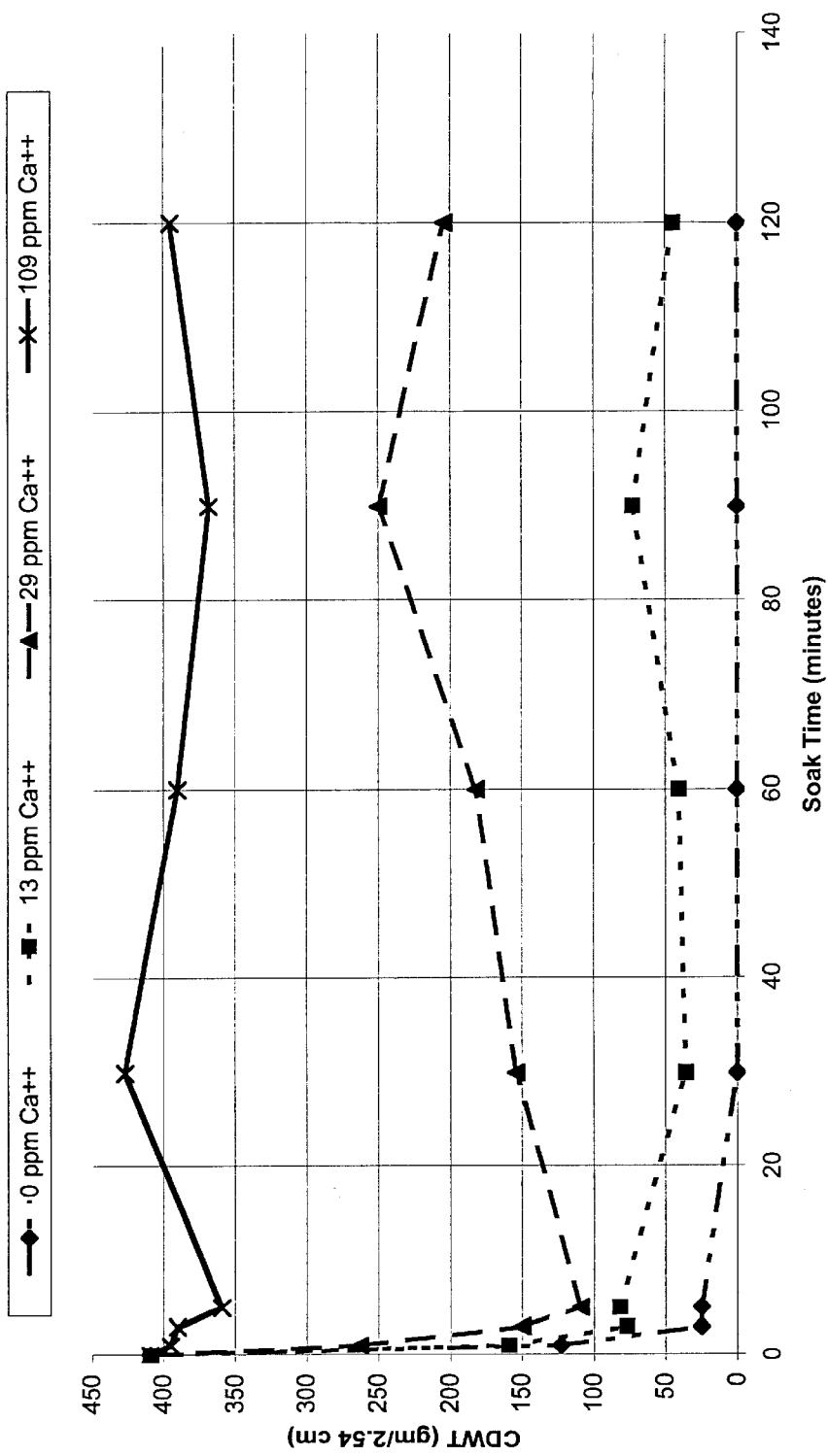
FIG. 2 is a chart showing how wet tensile strength (reported as CDWT in grams per 2.54 cm over a range of soak times) can change over time as a fabric, comprising 68 gsm softwood airlaid webs and ion-sensitive binders, are soaked in solutions comprising calcium ions.

FIG. 2 is a chart showing how wet tensile strength (reported as CDWT in grams per 2.54 cm over a range of soak times) can change over time as 68 gsm softwood airlaid webs comprising ion-sensitive binders are soaked in solutions comprising calcium ions. The moistened webs were prepared with 20% binder by weight comprising 85% Lion (Tokyo, Japan) SSB-3b acrylic-acid based terpolymer and 15% Dur-O-Set RB (National Starch) co-binder. After being dried, the webs were wetted with a solution containing 0.9% NaCl, 0.5% phospholipid CDM (Mona), and 0.5% Mackstat H-66 and displayed a wet strength of about 400 g/m (or g/2.54 cm). Solution add-on was 250% based on the dry weight of the web. The treated webs were then soaked in NaCl-free water containing calcium ions at levels of 0, 13, 29, and 109 ppm, yielding the four curves shown in FIG. 2 for wet tensile strength versus time. At 109 ppm calcium ions there is essentially no loss in strength. Strengths over 100 g/in are maintained in 29 ppm calcium ions. It appears that even a small amount of calcium ions in the water will interfere with a dispersibility of a web treated with the Lion SSB-3b product.

Figure 3:
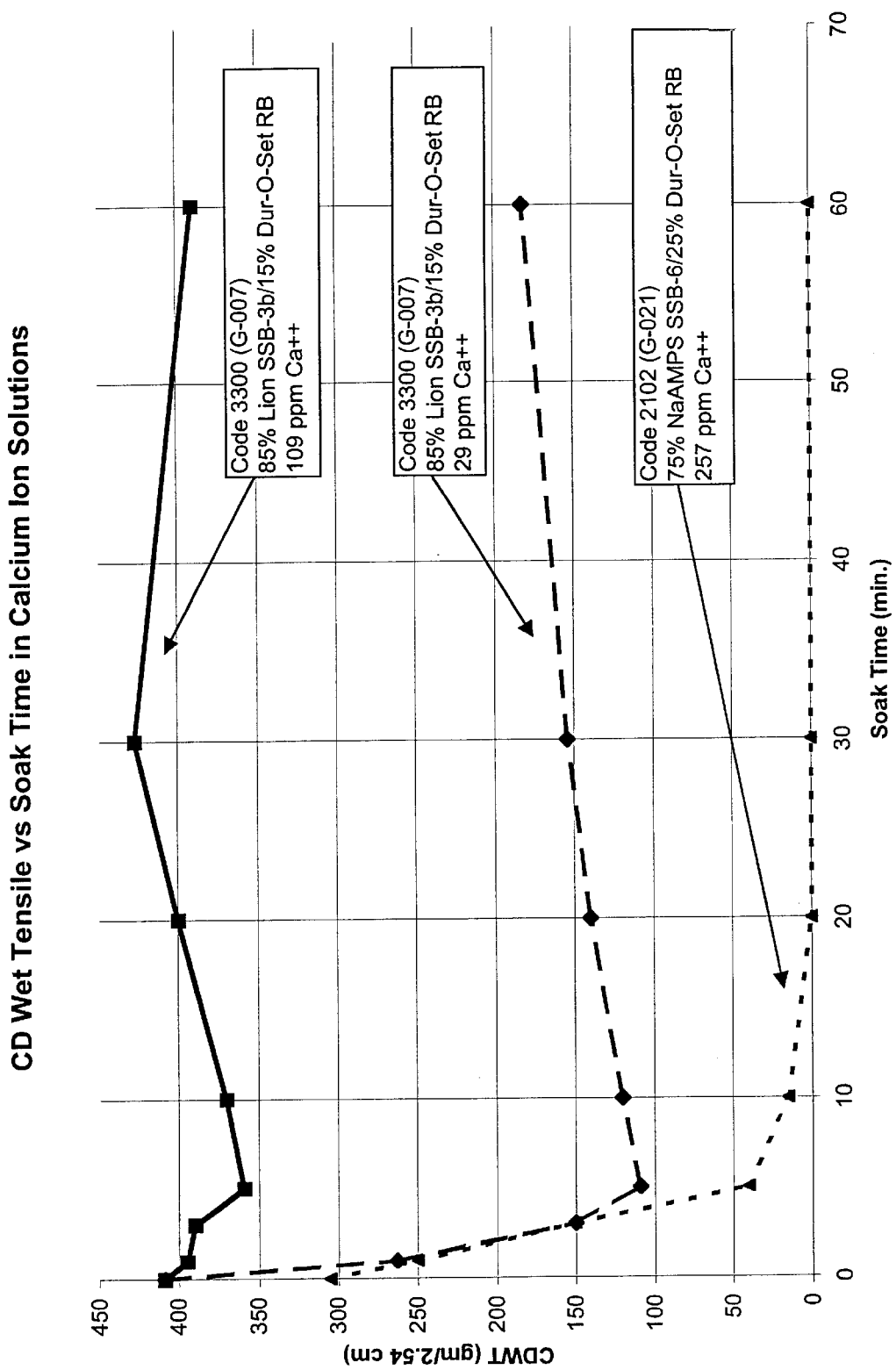
FIG. 3 compares two data sets with Lion SSB-3b product taken from FIG. 2 (labeled as Code 3300) with a sulfonated salt-sensitive binder blended with Dur-O-Set® RB polymer in a 75/25 ratio.

FIG. 3 compares two data sets with Lion SSB-3b product taken from FIG. 2 (labeled as Code 3300) with a sulfonated salt-sensitive binder blended with Dur-O-Set RB polymer in a 75/25 ratio. The data set labeled as Code 2102 refers to a 65-gsm web containing the sulfonated salt-sensitive binder, which corresponds to SSB Code H in Table 15. This web was wetted with the solution described in Table 4. Solution add-on was 225% based on the dry weight of the web. This binder formulation displayed a rapid drop in tensile strength—hence good triggerability—when immersed in hard water, even at a calcium ion concentration of 257 ppm. Thus, the sulfonated salt-sensitive binders of the present invention show a dramatic improvement in their ability to be dispersible in hard water relative to prior acrylic-acid based terpolymers.

Tensile results for data in FIG. 2 and FIG. 3 were obtained with an MTS tensile test devices, the MTS 500/S unit (MTS Systems, Research Park, N.C.) using the Testworks™ 3.10 for Windows software. Instead of the normal 3-inch strip for testing, a 1-inch wide strip was used, cut to 6 inches in length. The gauge length between the rubber-coated jaws of the test device was 3 inches. Testing was operated at the specified crosshead speed of 12 in/min.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A polymer formulation comprising a triggerable copolymer comprising acrylic acid, NaAMPS, butyl acrylate and 2-ethylhexyl acrylate and a non-crosslinkable co-binder polymer comprising poly(ethylene-vinyl acetate), wherein the polymer formulation is insoluble in a neutral salt solution containing at least about 1 weight percent salt, said salt comprising one or more monovalent ions; and wherein the triggerable copolymer is soluble in water containing up to about 200 ppm of one or more multivalent ions.

2. The polymer formulation of claim 1, wherein said acrylic acid comprises about 35 to less than 80 mole percent of said triggerable polymer.

3. The polymer formulation of claim 1, wherein said NaAMPS comprise greater than 0 to about 20 mole percent of said triggerable polymer.

4. The polymer formulation of claim 1, wherein said butyl acrylate comprise greater than 0 to about 65 mole percent of said triggerable polymer.

5. The polymer formulation of claim 1, wherein said 2-ethylhexyl acrylate comprises greater than 0 to about 45 mole percent of said triggerable polymer.

6. The polymer formulation of claim 1, wherein said acrylic acid comprises about 50 to about 67 mole percent of said triggerable polymer.

7. The polymer formulation of claim 1, wherein said NaAMPS comprise greater than 0 to about 10 mole percent of said triggerable polymer.

8. The polymer formulation of claim 1, wherein said butyl acrylate comprise about 15 to 28 mole percent of said triggerable polymer.

9. The polymer formulation of claim 1, wherein said 2-ethylhexyl acrylate comprises about 7 to 15 mole percent of said triggerable polymer.

10. The polymer formulation of claim 1, wherein said acrylic acid comprises about 57 to about 66 mole percent of said triggerable polymer.

11. The polymer formulation of claim 1, wherein said NaAMPS comprise about 1 to about 6 mole percent of said triggerable polymer.

12. The polymer formulation of claim 1, wherein said 2-ethylhexyl acrylate comprises about 7 to about 13 mole percent of said triggerable polymer.

13. The polymer formulation of claim 1, wherein said acrylic acid comprises about 60 mole percent of said triggerable polymer.

14. The polymer formulation of claim 1, wherein said NaAMPS comprise about 5 mole percent of said triggerable polymer.

15. The polymer formulation of claim 1, wherein said butyl acrylate comprise about 24.5 mole percent of said triggerable polymer.

16. The polymer formulation of claim 1, wherein said 2-ethylhexyl acrylate comprises about 10.5 mole percent of said triggerable polymer.

17. The polymer formulation of claim 1, wherein acrylic acid comprises about 35 to less than 80 mole percent, said NaAMPS comprises greater than 0 to about 20 mole percent, said butyl acrylate comprises greater than 0 to about 65 mole percent; and 2-ethylhexyl acrylate comprises greater than 0 to about 45 mole percent of said triggerable polymer.

18. The polymer formulation of claim 1, wherein acrylic acid comprises about 50 to 67 mole percent, said NaAMPS comprises greater than 0 to about 10 mole percent, said butyl acrylate comprises about 15 to 28 mole percent; and 2-ethylhexyl acrylate comprises about 7 to about 15 mole percent of said triggerable polymer.

19. The polymer formulation of claim 1, wherein acrylic acid comprises about 57 to 66 mole percent, said NaAMPS comprises about 1 to 6 mole percent, said butyl acrylate comprises about 15 to 28 mole percent; and 2-ethylhexyl acrylate comprises about 7 to about 13 mole percent of said triggerable polymer.

20. The polymer formulation of claim 1, wherein acrylic acid comprises about 60 mole percent, said NaAMPS comprises about 5 mole percent, said butyl acrylate comprises about 24.5 mole percent; and 2-ethylhexyl acrylate comprises about 10.5 mole percent of said triggerable polymer.

21. The polymer formulation of claim 1, wherein said triggerable polymer has a weight average molecular weight from about 10,000 to about 5,000,000.

22. The polymer formulation of claim 1, wherein said triggerable polymer has a weight average molecular weight from about 25,000 to about 2,000,000.

23. The polymer formulation of claim 1, wherein said triggerable polymer has a weight average molecular weight from about 200,000 to about 1,000,000.

24. The polymer formulation of claim 1, wherein said poly(ethylene-vinyl acetate) comprises about 5 to about 45 weight percent of said polymer formulation.

* * * * *